United States Patent
Shi et al.

(10) Patent No.: US 11,730,801 B2
(45) Date of Patent: Aug. 22, 2023

(54) LIVE ATTENUATED ZIKA VIRUS WITH 3'UTR DELETION, VACCINE CONTAINING AND USE THEREOF

(71) Applicant: THE BOARD OF REGENTS OF THE UNIVERSITY OF TEXAS SYSTEM, Austin, TX (US)

(72) Inventors: Pei-Yong Shi, Galveston, TX (US); Xuping Xie, Galveston, TX (US); Chao Shan, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/485,818

(22) PCT Filed: Feb. 14, 2018

(86) PCT No.: PCT/US2018/018114
§ 371 (c)(1),
(2) Date: Aug. 14, 2019

(87) PCT Pub. No.: WO2018/152158
PCT Pub. Date: Aug. 23, 2018

(65) Prior Publication Data
US 2020/0197505 A1   Jun. 25, 2020

Related U.S. Application Data

(60) Provisional application No. 62/458,839, filed on Feb. 14, 2017.

(51) Int. Cl.
*A61K 39/00* (2006.01)
*A61K 39/12* (2006.01)
*A61P 31/14* (2006.01)

(52) U.S. Cl.
CPC ............. *A61K 39/12* (2013.01); *A61P 31/14* (2018.01); *A61K 2039/53* (2013.01); *A61K 2039/555* (2013.01); *A61K 2039/57* (2013.01)

(58) Field of Classification Search
None
See application file for complete search history.

(56) References Cited

U.S. PATENT DOCUMENTS

| 2010/0104598 | A1* | 4/2010 | Whitehead | ............. C12N 7/045 424/218.1 |
| 2017/0296646 | A1* | 10/2017 | Hernandez | ............. A61P 31/14 |

FOREIGN PATENT DOCUMENTS

| WO | WO 2017/009873 | 1/2017 |
| WO | WO 2018/129160 | 7/2018 |

OTHER PUBLICATIONS

Xie et al., "Understanding Zika Virus Stability and Developing a Chimeric Vaccine through Functional Analysis," mBio 8:e02134-16 (Year: 2017).*

(Continued)

*Primary Examiner* — M Franco G Salvoza

(57) ABSTRACT

The present invention discloses a live attenuated strain of Zika virus (ZIKV) having a deletion in the 3' untranslated region (3'UTR) of the viral genome, which may affect viral RNA synthesis and sensitivity to type I interferon inhibition, but may not affect viral RNA translation. The present invention also discloses the use of these live attenuated ZIKV strains in the preparation of ZIKV vaccines and for providing immunoprotection against ZIKV infection and congenital ZIKV syndrome, particularly in pregnant females.

16 Claims, 24 Drawing Sheets

Specification includes a Sequence Listing.

(56) References Cited

OTHER PUBLICATIONS

Ladner et al., "Complete Genome Sequences of Five Zika Virus Isolates," Genome Announc 4(3):e00377 (Year: 2016).*
Haddow et al., "Genetic Characterization of Zika Virus Strains: Geographic Expansion of the Asian Lineage," PLoS, Negl Trop Dis 6(2): e1477 (Year: 2012).*
Marrs et al., "Zika Virus and Pregnancy: A Review of the Literature and Clinical Considerations," Am J Perinatol. 33(7): 625-639 (Year: 2016).*
Malone et al., "Zika Virus: Medical Countermeasure Development Challenges," PLoS Negl Trop Dis 10(3): e0004530 (Year: 2016).*
Morrison et al., "Animal Models of Zika Virus Infection, Pathogenesis, and Immunity," Journal of Virology, vol. 91, Issue 8: e00009-17 (Year: 2017).*
International Search Report and Written Opinion issued in corresponding International Application No. PCT/US18/18114 dated May 24, 2018.
Manzano et al., "Identification of Cis-Acting Elements in the 3'Untranslated Region of the Dengue Virus Type 2 RNA That Modulate Translation and Replication." *J Biol Chem*, vol. 286, No. 25, pp. 22521-22534, 2011.
Men et al., "Dengue type 4 virus mutants containing deletions in the 3' noncoding region of the RNA genome: Analysis of growth restriction in cell culture and altered viremia pattern and immunogenicity in Rhesus monkeys." *J. Virol*, 70(6): 3930-3937, 1996.
Shan et al., "A live-attenuated Zika virus vaccine candidate induces sterilizing immunity in mouse models." *Nat Med.*, 23(6):763-767, 2017.
Supplementary European Search Report from the European Patent Office issued in corresponding Patent Application EP 18 75 4135 dated Sep. 8, 2020.
Xie et al., Understanding Zika Virus Stability and Developing a Chimeric Vaccine through Functional Analysis, *mBio*, vol. 8 No. 1 article e02134-16, pp. 1-14, 2017.

\* cited by examiner

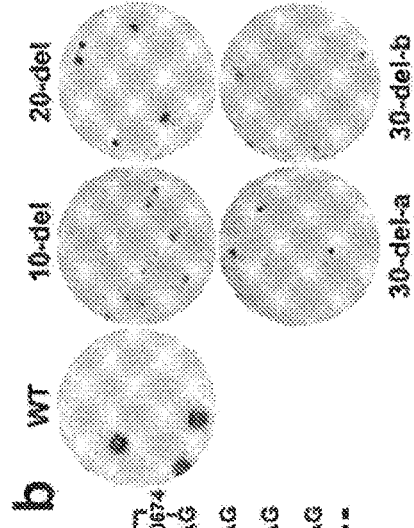
FIGURE 1A
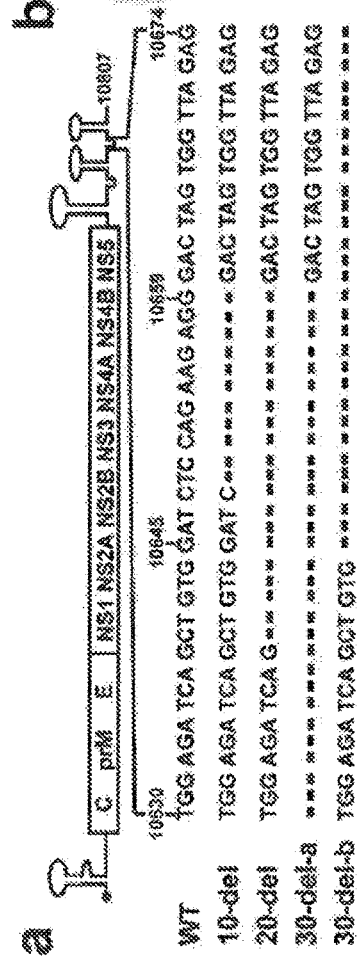
FIGURE 1B
FIGURE 1C
FIGURE 1D
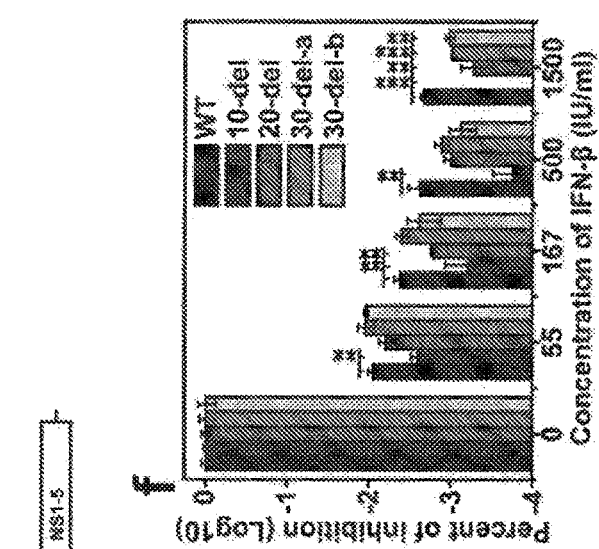
FIGURE 1E
FIGURE 1F

FIGURE 2B

```
                              10-del
                           ──────────────
                      TGG AGA TCA GCT GTG GAT CTC CAG AAG AGG GAC TAG TGG TTA GAG
FSS13025/KU955593     ... ... ... ... ... ... ... ... ... ... ... ... ... ... ...
H/PF2013/KJ776791     ... ... ... ... ... ... ... ... ... ... ... ... ... ... ...
PRVABC 59/KU501215    ... ... ... ... ... ... ... ... ... ... ... ... ... ... ...
Natal RGN/KU527068    ... ... ... ... ... ... ... ... ... ... ... ... ... ... ...
ZKV2015/KU497555      ... ... ... ... ... ... ... ... ... ..G ... ... ... ... ...
P6-740/KX377336       ... ... ..CT ... ..A ... ... ... ... ..C ... ..C ... ... ...
MR 766/ AY632535      ... ..T ... ..A ... ..G ... ..G ..C ..A ... ... ... ... ...
DAK-41525/KU955591    ... ... ... ... ... ... ... ... ... ... ... ... ... ... ...
```

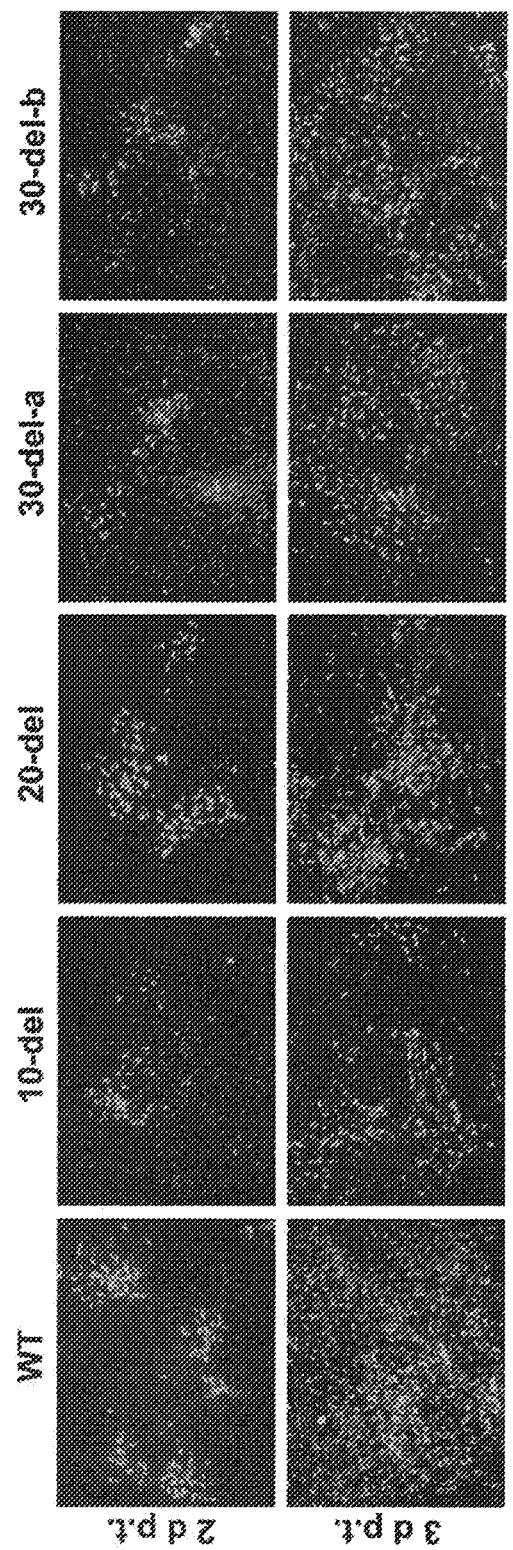

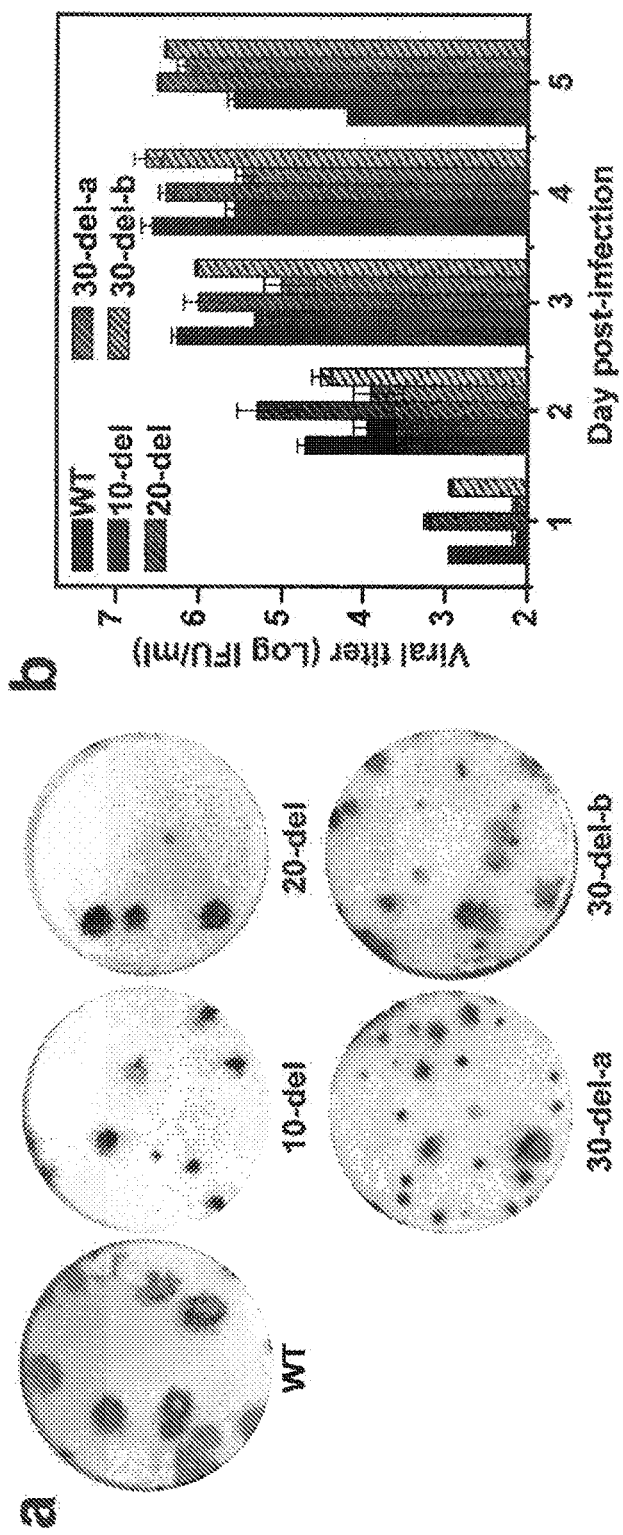
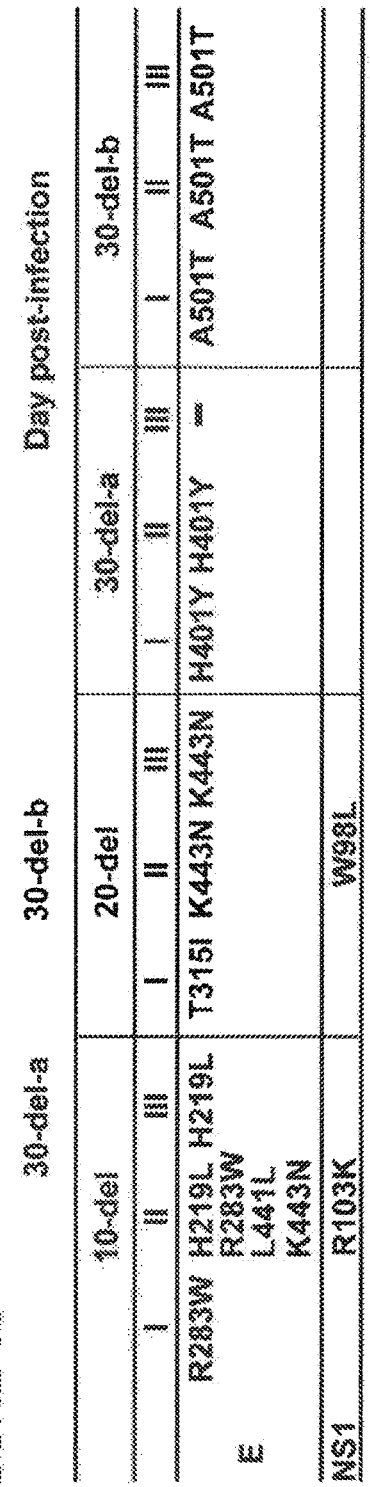
FIGURE 4A
FIGURE 4B
FIGURE 4C

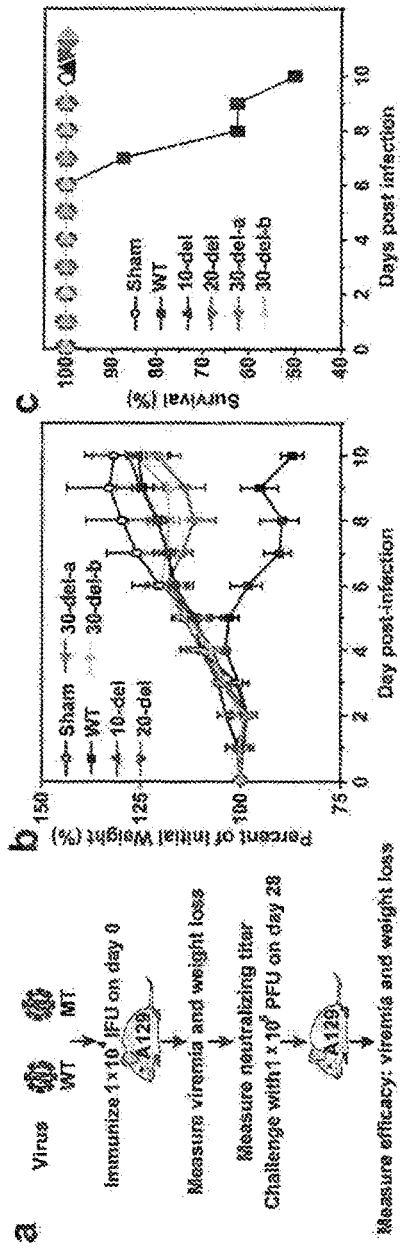
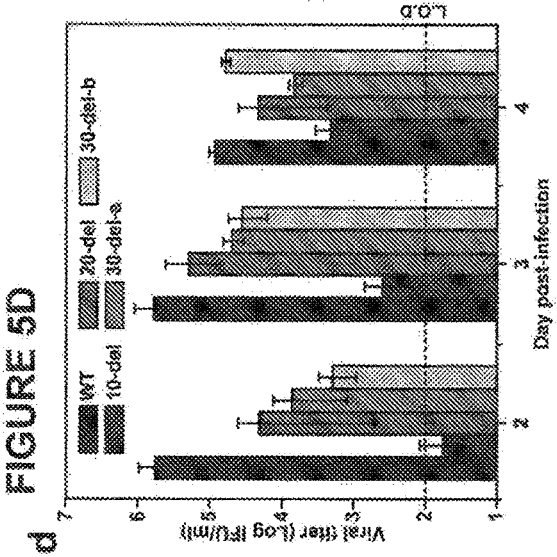
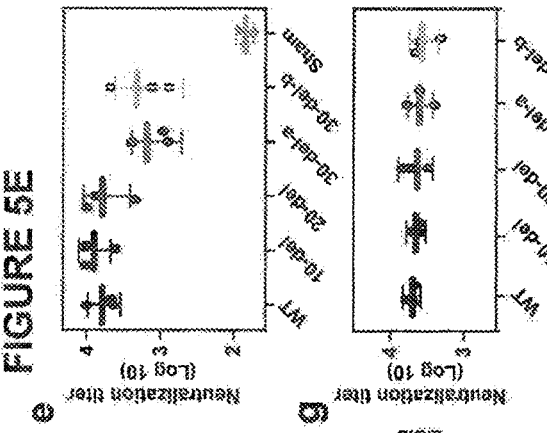
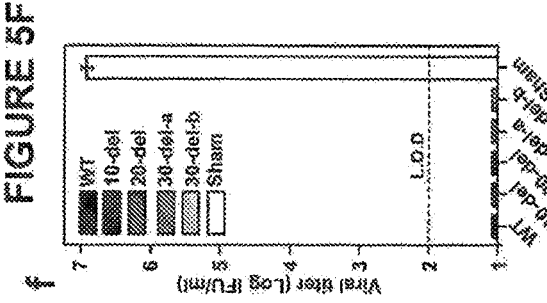

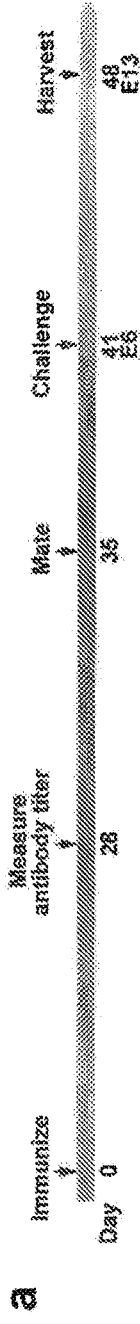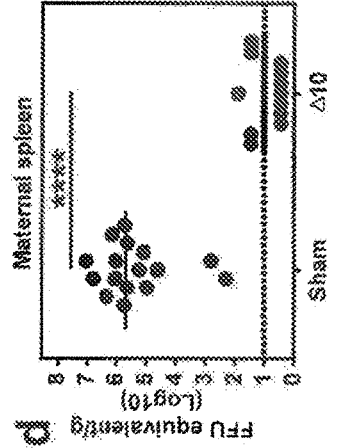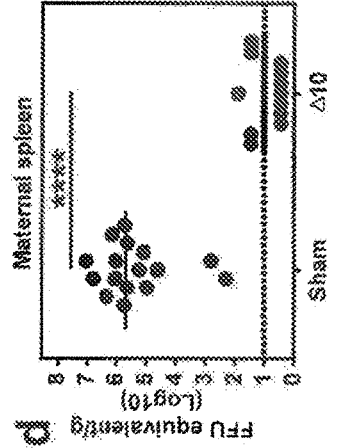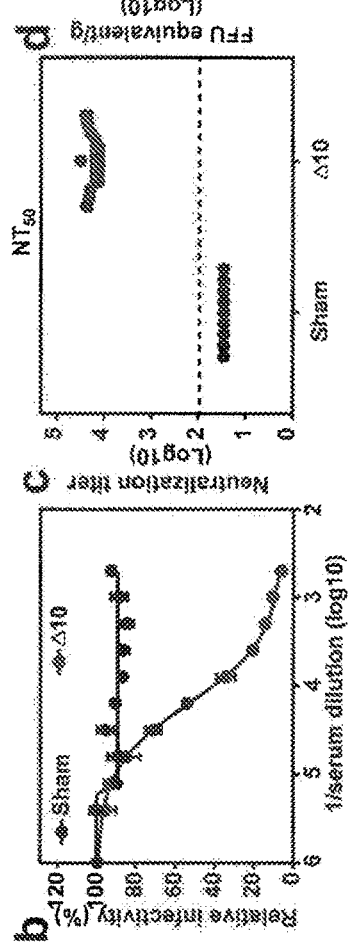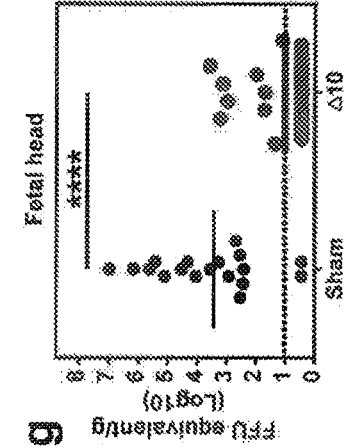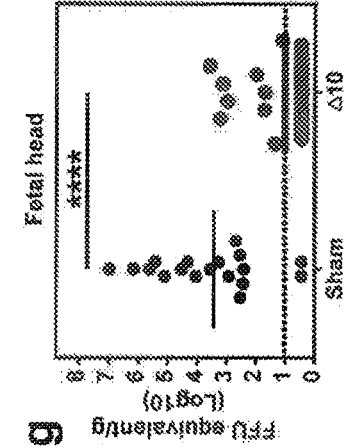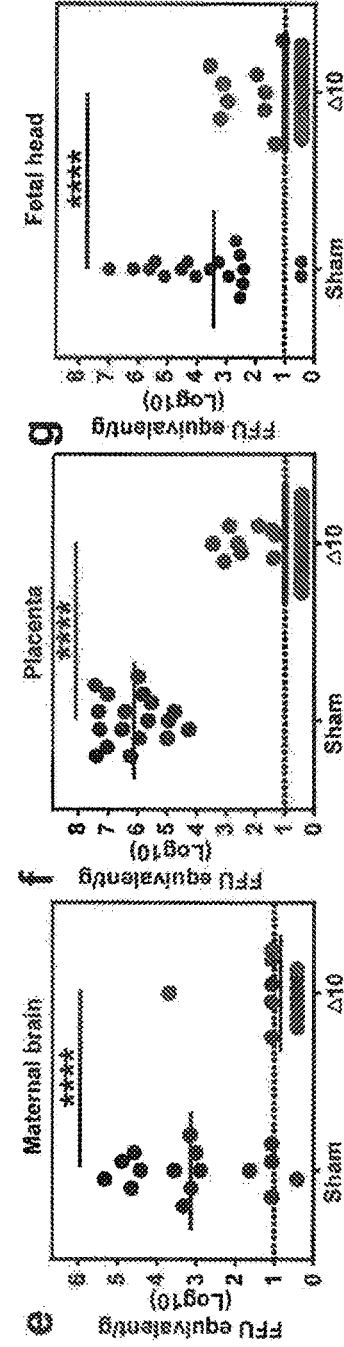

FIGURE 14A
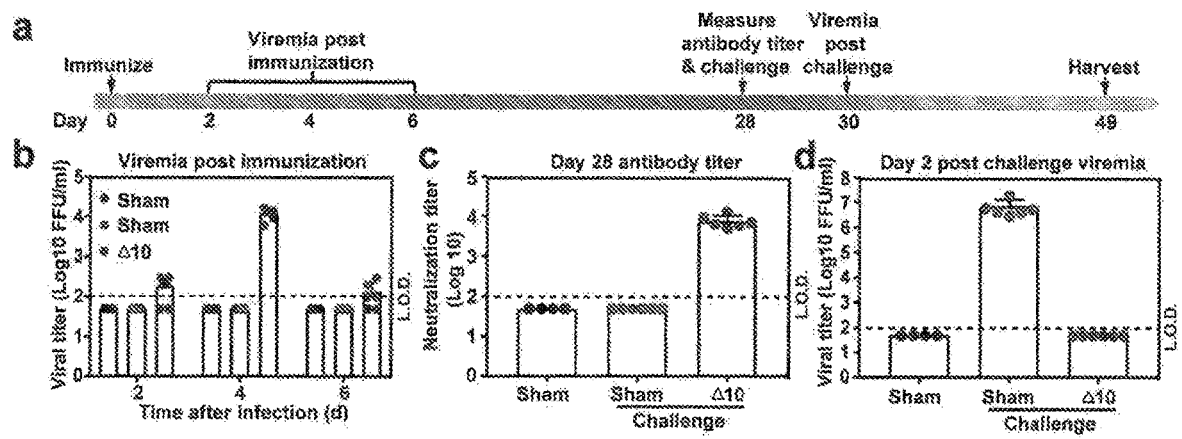
FIGURE 14B    FIGURE 14C    FIGURE 14D
FIGURE 14E    FIGURE 14F    FIGURE 14G
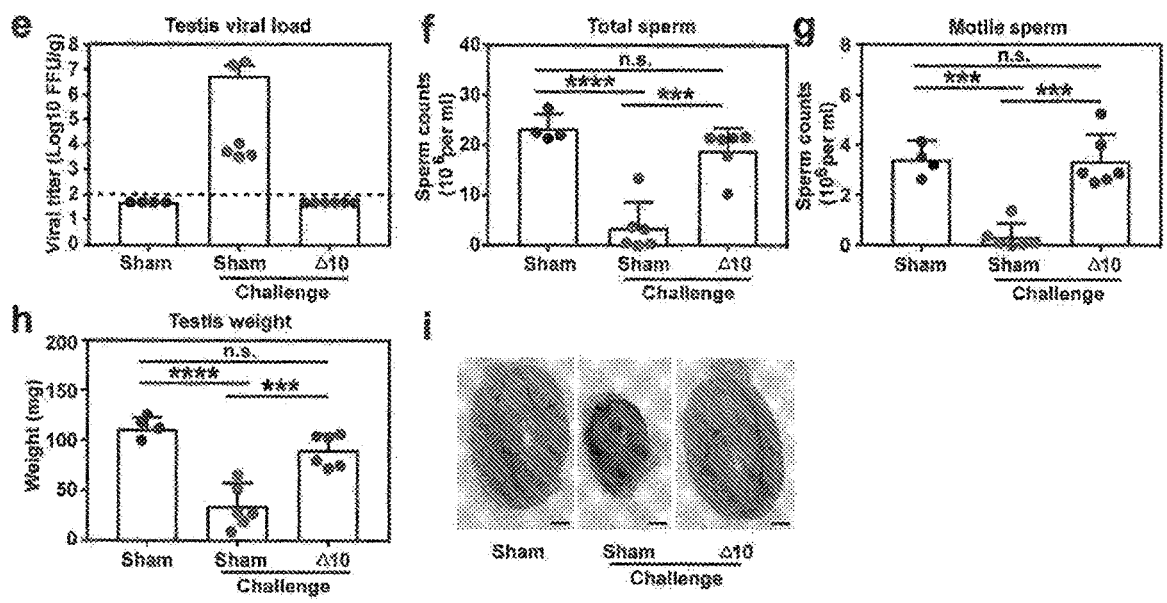
FIGURE 14H    FIGURE 14I

FIGURE 15A
FIGURE 15B
FIGURE 15C
FIGURE 15D

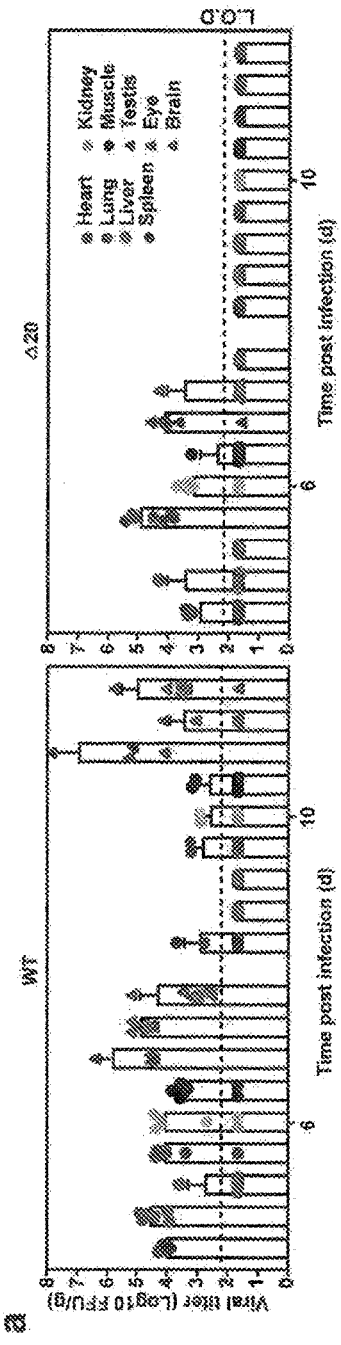
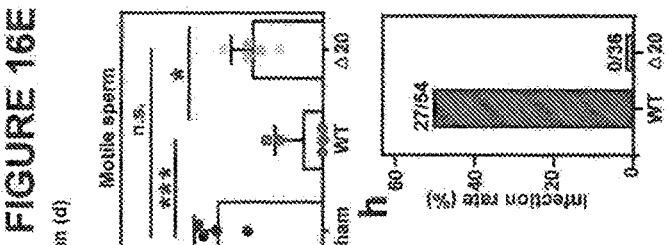
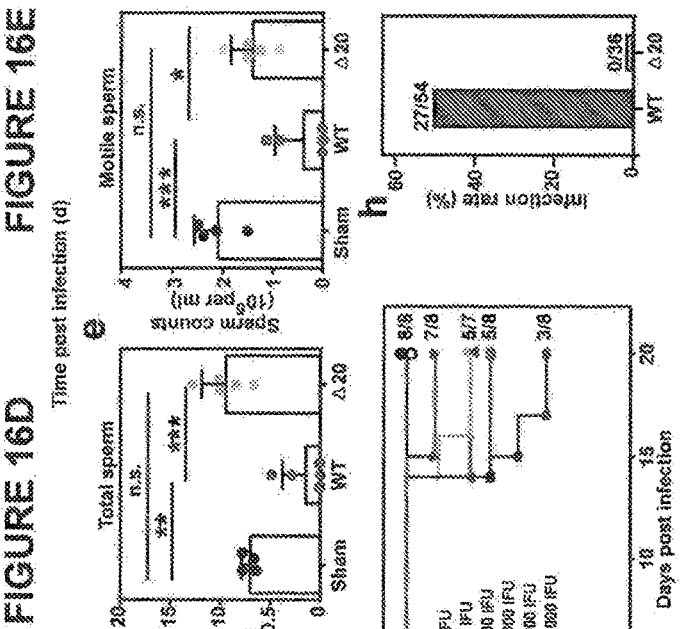
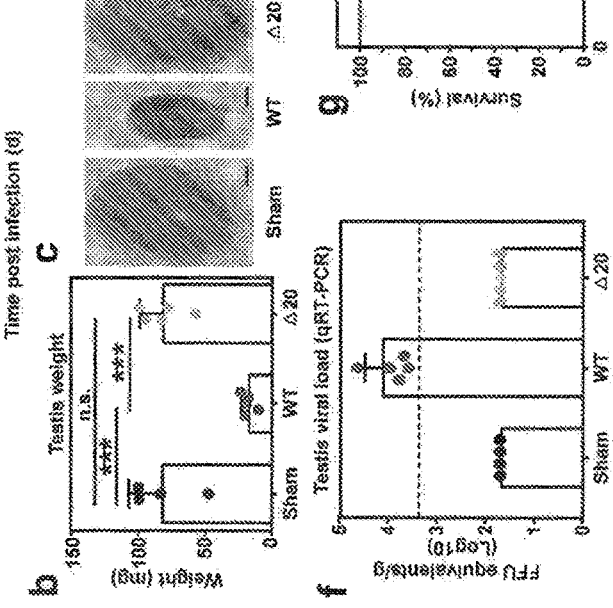
FIGURE 16A FIGURE 16B FIGURE 16C FIGURE 16D FIGURE 16E FIGURE 16F FIGURE 16G FIGURE 16H

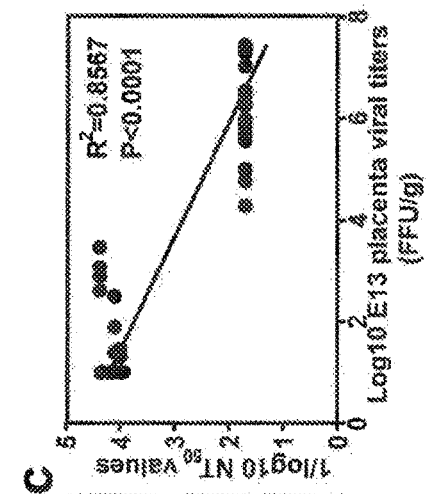
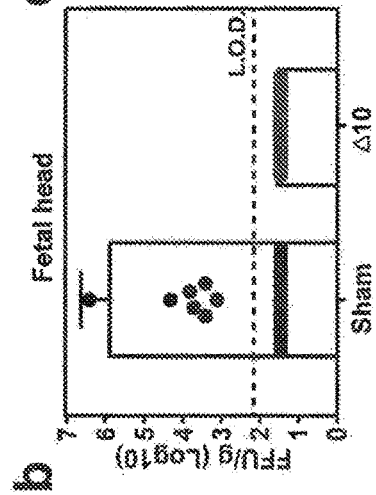
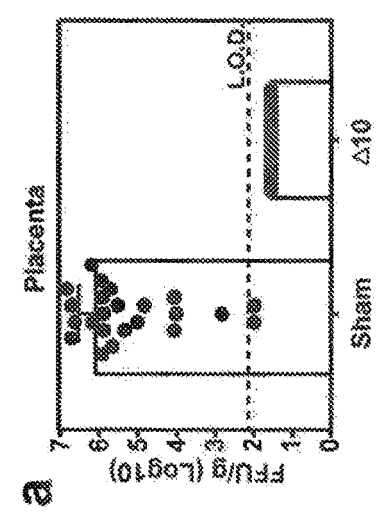
Figures 17A-C. Infectious ZIKV burden in placentas and fetal heads from FIGURE 18A
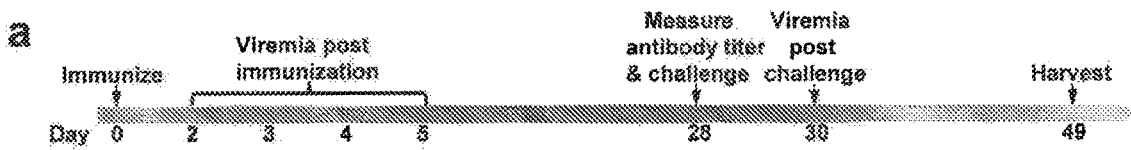
FIGURE 18B
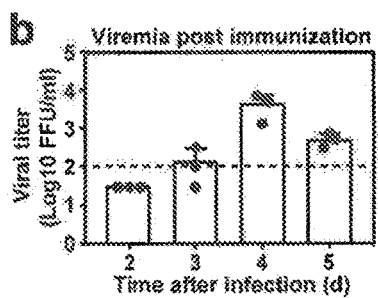
FIGURE 18C
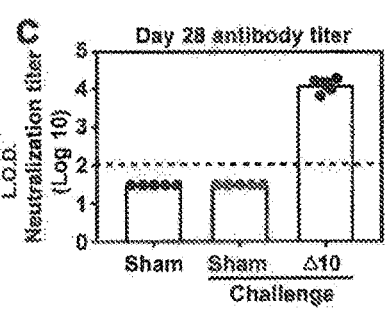
FIGURE 18D
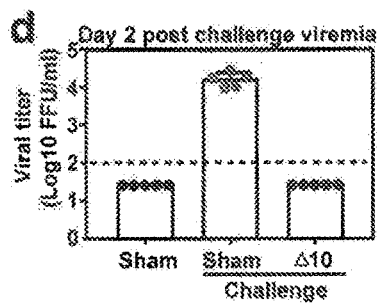
FIGURE 18E
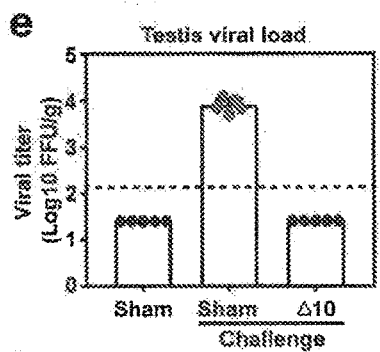
FIGURE 18F
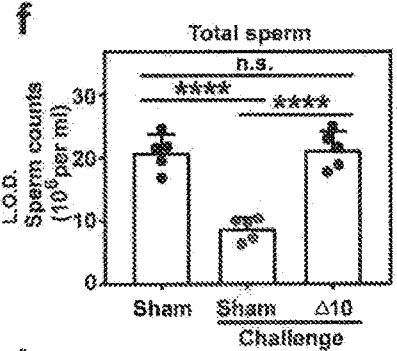
FIGURE 18G
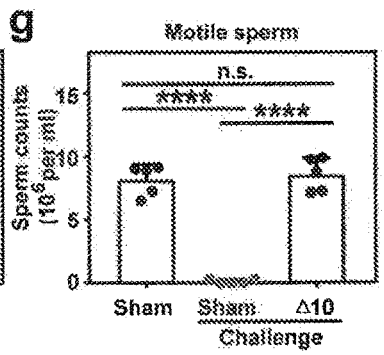
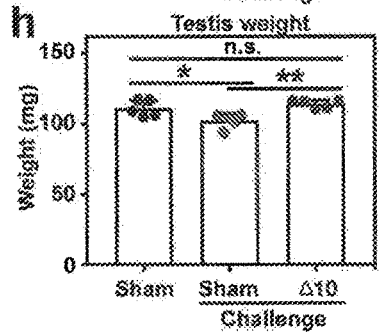
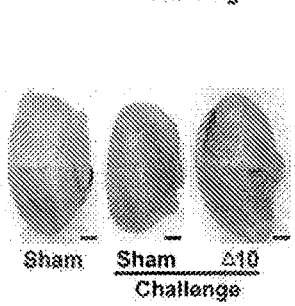
FIGURE 18H          FIGURE 18I
Figures 18A-I. ZIKV-3'UTR-Δ10-LAV protects adult A129 male mice against testis infection and injury.

Figures 19A-B. Infectious virus in serum of challenged rhesus macaque.

Figures 20A-I. ZIKV-3'-UTR-Δ20-LAV protects young A129 male mice against testis infection and injury.

FIGURE 21

Sequencing results for ZIKV-3'UTR-Δ20-LAV P5 viruses

|  | E | NS1 |
|---|---|---|
| Selection I | T315I | - |
| Selection II | K443N | W98L |
| Selection III | K443N | - |

Figure 21. Stability analysis of ZIKV-3'UTR-Δ20-LAV in cell culture.

FIGURE 22

FIGURE 22: Yield of ZIKV on VERO cells.

FIGURE 23

Figure 23. Yield of ZIKV DNA vaccine candidates on Vero cells.

SEQUENCE LISTING

```
<160> NUMBER OF SEQ ID NOS: 32

<210> SEQ ID NO 1
<211> LENGTH: 429
<212> TYPE: DNA
<213> ORGANISM: Artificial Sequence
<220> FEATURE:
<223> OTHER INFORMATION: 3'UTR-WT

<400> SEQUENCE: 1
gcaccaatct tagtgttgtc aggcctgcta gtcagccaca gcttggggaa agctgtgcag       60
cctgtgaccc ccccaggaga agctgggaaa ccaagcccat agtcaggccg agaacgccat      120
ggcacggaag aagccatgct gcctgtgagc ccctcagagg acactgagtc aaaaaacccc      180
acgcgcttgg aggcgcagga tgggaaaaga aggtggcgac cttccccacc ctttaatctg      240
gggcctgaac tggagatcag ctgtggatct ccagaagagg gactagtggt tagaggagac      300
cccccggaaa acgcaaaaca gcatattgac gctgggaaag accagagact ccatgagttt      360
ccaccacgct ggccgccagg cacagatcgc cgaatagcgg cggccggtgt ggggaaatcc      420
atggtttct                                                             429

<210> SEQ ID NO 2
<211> LENGTH: 419
<212> TYPE: DNA
<213> ORGANISM: Artificial Sequence
<220> FEATURE:
<223> OTHER INFORMATION: 3'UTR-10-del

<400> SEQUENCE: 2
gcaccaatct tagtgttgtc aggcctgcta gtcagccaca gcttggggaa agctgtgcag       60
cctgtgaccc ccccaggaga agctgggaaa ccaagcccat agtcaggccg agaacgccat      120
```

| | |
|---|---|
| ggcacggaag aagccatgct gcctgtgagc ccctcagagg acactgagtc aaaaaacccc | 180 |
| acgcgcttgg aggcgcagga tgggaaaaga aggtggcgac cttccccacc ctttaatctg | 240 |
| gggcctgaac tggagatcag ctgtggatct gactagtggt tagaggagac ccccggaaa | 300 |
| acgcaaaaca gcatattgac gctgggaaag accagagact ccatgagttt ccaccacgct | 360 |
| ggccgccagg cacagatcgc cgaatagcgg cggccggtgt ggggaaatcc atggtttct | 419 |

```
<210> SEQ ID NO 3
<211> LENGTH: 409
<212> TYPE: DNA
<213> ORGANISM: Artificial Sequence
<220> FEATURE:
<223> OTHER INFORMATION: 3'UTR-20-del

<400> SEQUENCE: 3
```

| | |
|---|---|
| gcaccaatct tagtgttgtc aggcctgcta gtcagccaca gcttggggaa agctgtgcag | 60 |
| cctgtgaccc ccccaggaga agctgggaaa ccaagcccat agtcaggccg agaacgccat | 120 |
| ggcacggaag aagccatgct gcctgtgagc ccctcagagg acactgagtc aaaaaacccc | 180 |
| acgcgcttgg aggcgcagga tgggaaaaga aggtggcgac cttccccacc ctttaatctg | 240 |
| gggcctgaac tggagatcag gactagtggt tagaggagac ccccggaaa acgcaaaaca | 300 |
| gcatattgac gctgggaaag accagagact ccatgagttt ccaccacgct ggccgccagg | 360 |
| cacagatcgc cgaatagcgg cggccggtgt ggggaaatcc atggtttct | 409 |

```
<210> SEQ ID NO 4
<211> LENGTH: 399
<212> TYPE: DNA
<213> ORGANISM: Artificial Sequence
<220> FEATURE:
<223> OTHER INFORMATION: 3'UTR-30-del-a

<400> SEQUENCE: 4
```

| | |
|---|---|
| gcaccaatct tagtgttgtc aggcctgcta gtcagccaca gcttggggaa agctgtgcag | 60 |
| cctgtgaccc ccccaggaga agctgggaaa ccaagcccat agtcaggccg agaacgccat | 120 |
| ggcacggaag aagccatgct gcctgtgagc ccctcagagg acactgagtc aaaaaacccc | 180 |
| acgcgcttgg aggcgcagga tgggaaaaga aggtggcgac cttccccacc ctttaatctg | 240 |
| gggcctgaac gactagtggt tagaggagac ccccggaaa acgcaaaaca gcatattgac | 300 |
| gctgggaaag accagagact ccatgagttt ccaccacgct ggccgccagg cacagatcgc | 360 |
| cgaatagcgg cggccggtgt ggggaaatcc atggtttct | 399 |

```
<210> SEQ ID NO 5
<211> LENGTH: 399
<212> TYPE: DNA
<213> ORGANISM: Artificial Sequence
<220> FEATURE:
<223> OTHER INFORMATION: 3'UTR-30-del-b

<400> SEQUENCE: 5
```

| | |
|---|---|
| gcaccaatct tagtgttgtc aggcctgcta gtcagccaca gcttggggaa agctgtgcag | 60 |
| cctgtgaccc ccccaggaga agctgggaaa ccaagcccat agtcaggccg agaacgccat | 120 |
| ggcacggaag aagccatgct gcctgtgagc ccctcagagg acactgagtc aaaaaacccc | 180 |
| acgcgcttgg aggcgcagga tgggaaaaga aggtggcgac cttccccacc ctttaatctg | 240 |
| gggcctgaac tggagatcag ctgtggagac ccccggaaa acgcaaaaca gcatattgac | 300 |
| gctgggaaag accagagact ccatgagttt ccaccacgct ggccgccagg cacagatcgc | 360 |

```
cgaatagcgg cggccggtgt ggggaaatcc atggtttct                          399
```

<210> SEQ ID NO 6
<211> LENGTH: 18611
<212> TYPE: DNA
<213> ORGANISM: Artificial Sequence
<220> FEATURE:
<223> OTHER INFORMATION: CMV ZIKV FL sequence

<400> SEQUENCE: 6

```
agttgttgat ctgtgtgaat cagactgcga cagttcgagt ttgaagcgaa agctagcaac    60
agtatcaaca ggttttattt tggatttgga aacgagagtt tctggtcatg aaaaacccaa   120
agaagaaatc cggaggattc cggattgtca atatgctaaa acgcggagta gcccgtgtga   180
gccccttggg gggcttgaag aggctgccag ccggacttct gctgggtcat gggcccatca   240
ggatggtctt ggcgattcta gccttttga gattcacggc aatcaagcca tcactgggtc    300
tcatcaatag atggggttca gtggggaaaa aagaggctat ggaataata agaagttta     360
agaaagatct ggctgccatg ctgagaataa tcaatgctag gaaggagaag aagagacgag   420
gcacagatac tagtgtcgga attgttggcc tcctgctgac cacagccatg gcagtggagg   480
tcactagacg tgggaatgca tactatatgt acttggacag aagcgatgct ggggaggcca   540
tatcttttcc aaccacaatg gggatgaata agtgttatat acagatcatg gatcttggac   600
acatgtgtga tgccaccatg agctatgaat gccctatgct ggatgagggg gtagaaccag   660
atgacgtcga ttgttggtgc aacacgacgt caacttgggt tgtgtacgga acctgccacc   720
acaaaaaagg tgaagcacgg agatctagaa gagctgtgac gctcccctcc cattccacta   780
ggaagctgca aacgcggtcg cagacctggt tggaatcaag agaatacaca agcacctga    840
ttagagtcga aaattggata ttcaggaacc ctggcttcgc gttagcagca gctgccatcg   900
cttggctttt gggaagctca acgagccaaa aagtcatata cttggtcatg atactgctga   960
ttgccccggc atacagcatc aggtgcatag gagtcagcaa tagggacttt gtggaaggta  1020
tgtcaggtgg gacttgggtt gatgttgtct tggaacatgg aggttgtgtt accgtaatgg  1080
cacaggacaa accgactgtc gacatagagc tggttacaac aacagtcagc aacatggcgg  1140
aggtaagatc ctactgctat gaggcatcaa tatcggacat ggcttcggac agccgctgcc  1200
caacacaagg tgaagcctac cttgacaagc aatcagacac tcaatatgtc tgcaaaagaa  1260
cgttagtgga cagaggctgg ggaaatggat gtggactttt tggcaaaggg agcctggtga  1320
catgcgctaa gtttgcttgc tctaagaaaa tgaccgggaa gagcatccag ccagagaatc  1380
tggagtaccg gataatgctg tcagttcatg gctcccagca cagtgggatg atcgttaatg  1440
atacaggaca tgaaactgat gagaatagag cgaaggttga gataacgccc aattcaccaa  1500
gagccgaagc caccctgggg ggttttggaa gcctaggact tgattgtgaa ccgaggacag  1560
gccttgactt tcagatttg tattacttga ctatgaataa caagcactgg ttggttcaca   1620
aggagtggtt ccacgacatt ccattacctt ggcacgctgg ggcagacacc ggaactccac  1680
actggaacaa caaagaagca ctggtagagt tcaaggacgc acatgccaaa aggcagactg  1740
tcgtggttct agggagtcaa gaaggagcag ttcacacggc ccttgctgga gctctggagg  1800
ctgagatgga tggtgcaaag ggaaggctgt cctctggcca cttgaaatgt cgcctgaaaa  1860
tggacaaact agattgaag gcgtgtcat actccttgtg taccgcagcg ttcacattca    1920
ctaagatccc ggctgaaaca ctgcacggga cagtcacagt ggaggtacag tacgcaggga  1980
```

```
cagatggacc ttgcaaggtt ccagctcaga tggcggtgga catgcaaact ctgaccccag      2040
ttgggaggtt gataaccgct aaccctgtaa tcactgaaag cactgagaac tccaagatga      2100
tgctggaact ggatccacca tttggggact cttacattgt cataggagtc ggggaaaaga      2160
agatcaccca ccactggcac aggagtggca gcaccattgg aaaagcattt gaagccactg      2220
tgagaggtgc caagagaatg gcagtcttgg gagacacagc ctgggacttt ggatcagttg      2280
ggggtgctct caactcactg gcaagggca tccatcaaat ttttggagca gctttcaaat       2340
cattgtttgg aggaatgtcc tggttctcac aaattctcat tggaacgttg ctggtgtggt      2400
tgggtctgaa tacaaagaat ggatctattt cccttatgtg cttggcctta ggggagtgt       2460 tgatcttctt atccacagcc gtctctgctg atgtggggtg ctcggtggac ttctcaaaga      2520
aggaaacgag atgcggtaca ggggtgttcg tctataacga cgttgaagct tggagggaca      2580
ggtacaagta ccatcctgac tcccctcgta gattggcagc agcagtcaag caagcctggg      2640
aagatgggat ctgtgggatc tcctctgttt caagaatgga aaacatcatg tggagatcag      2700
tagaagggga gctcaacgca atcctggaag agaatggagt tcaactgacg gtcgttgtgg      2760
gatctgtaaa aaaccccatg tggagaggtc cacagagatt gcccgtgcct gtgaacgagc      2820
tgccccatgg ctggaaggct tgggggaaat cgtacttcgt cagggcagca agacaaata      2880 acagctttgt cgtggatggt gacacactga aggaatgccc actcaaacat agagcatgga      2940
acagctttct tgtggaggat catgggttcg gggtatttca cactagtgtc tggctcaagg      3000
ttagagaaga ttattcactc gagtgtgatc cagccgtcat tggaacagcc gctaagggaa      3060
aggaggctgt gcacagtgat ctaggctact ggattgagag tgagaagaac gacacatgga      3120
ggctgaagag ggcccaccctg atcgagatga aaacatgtga atggccaaag tcccacacat      3180 tgtgacaga tggaatagaa gaagtgatc tgatcatacc caagtcttta gctgggccac       3240
tcagccatca aacaccaga gagggctaca ggacccaaat gaaagggcca tggcatagtg      3300
aagagcttga aattcggttt gaggaatgcc caggcactaa ggtccacgtg gaggaaacat      3360
gtggaacaag aggaccatct ctgagatcaa ccactgcaag cggaagggtg atcgaggaat      3420
ggtgctgcag ggagtgcaca atgccccac tgtcgttccg ggctaaagat ggttgttggt      3480
atggaatgga gataaggccc aggaaagaac cagaaagtaa cttagtaagg tcaatggtga      3540
ctgcaggatc aactgatcac atggatcact tctcccttgg agtgcttgtg attctgctca      3600
tggtacagga agggctaaag aagagaatga ccacaaagat catcataagc acatcaatgg      3660
cagtgctggt agctatgatc ctgggaggat tttcaatgag tgacctggct aagcttgcaa      3720
ttttgatggg tgccaccttc gcggaaatga acactggagg agatgttgct catctggcgc      3780
tgatagcggc attcaaagtc agacctgcgt tgctggtatc tttcattttc agagctaatt      3840
ggacaccccg tgagagcatg ctgctggcct tggcctcgtg tcttctgcaa actgcgatct      3900
ccgccttgga aggcgacctg atggttccca tcaatggttt tgctttggcc tggttggcaa      3960
tacgagcgat ggttgttcca cgcactgaca acatcacctt ggcaatcctg ctgctctgat       4020
caccactggc ccggggcaca ctgcttgtgg cgtggagagc aggccttgct acttgcgggg      4080
ggttcatgct cctttctctg aaggggaaag gcagtgtgaa gaagaactta ccatttgtca      4140 tggcccctggg actaaccgct gtgaggctgg tcgacccat caacgtggtg ggactgctgt       4200
tgctcacaag gagtgggaag cggagctggc cccctagtga agtactcaca gctgttggcc      4260
tgatatgcgc attggctgga gggttcgcca aggcggatat agagatggct gggcccatgg      4320
ccgcggtcgg tctgctaatt gtcagttacg tggtctcagg aaagagtgtg gacatgtaca      4380
```

```
ttgaaagagc aggtgacatc acatgggaaa aagatgcgga agtcactgga aacagtcccc    4440
ggctcgatgt ggcactagat gagagtggtg atttctccct agtggaggat gatggtcccc    4500
ccatgagaga gatcatactc aaagtggtcc tgatggccat ctgtggcatg aacccaatag    4560
ccataccctt tgcagctgga gcgtggtacg tgtatgtgaa gactggaaaa aggagtggtg    4620
ctctatggga tgtgcctgct cccaaggaag taaaaaggg ggagaccaca gatggagtgt     4680
acagagtaat gactcgtaga ctgctaggtt caacacaagt tggagtggga gtcatgcaag    4740
aggggtctt ccacactatg tggcacgtca caaaggatc cgcgctgaga agcggtgaag       4800
ggagacttga tccatactgg ggagatgtca agcaggatct ggtgtcatac tgtggtccat    4860
ggaagctaga tgccgcctgg gacgggcaca gcgaggtgca gctcttggcc gtgccccccg    4920
gagagagagc gaggaacatc cagactctgc ccggaatatt taagacaaag gatgggggaca   4980
ttggagcagt tgcgctggac tacccagcag gtacctcagg atctccaatc ctagataagt    5040
gtgggagagt gataggactc tatggtaatg ggtcgtgat caaaaatggg agttacgtta     5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
gagttcttcc tgaaatagtc cgtgaagcca taaaaacaag actccgcact gtgatcttag    5280
ctccaaccag ggttgtcgct gctgaaatgg aggaagccct tagagggctt ccagtgcgtt    5340
atatgacaac agcagtcaat gtcacccatt ctgggacaga aatcgttgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac tgccacgcca ccaggaaccc    5580
gtgacgcatt cccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaatggc aatgagatcg cagcttgtct gacaaaggct ggaaaacggg    5760
tcatacagct cagcagaaag acttttgaga cagagttcca gaaaacaaaa catcaagagt    5820
gggacttcgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggcgc ataggcagga    6000
accccaacaa acctggagat gagtatctgt atggaggtgg gtgcgcagag actgatgaag    6060
accatgcaca ctggcttgaa gcaagaatgc ttcttgacaa catttacctc caagatggcc    6120
tcatagcctc gctctatcga cctgaggccg acaaagtagc agctattgag ggagagttca    6180
agcttaggac ggagcaaagg aagaccttg tggaactcat gaaaagagga atcttcctg      6240
tttggctggc ctatcaggtt gcatctgccg gaataaccta cacagataga agatggtgct    6300
ttgatggcac gaccaacaac accataatgg aagacagtgt gccggcagag gtgtggacca    6360
gatacggaga gaaaagagtg ctcaaaccga ggtggatgga cgccagagtt tgttcagatc    6420
atgcggccct gaagtcattc aaagagtttg ccgctgggaa aagaggagcg ccttttggag    6480
tgatggaagc cctgggaaca ctgccaggac atatgacaga gagattccag gaggccattg    6540
acaacctcgc tgtgctcatg cgggcagaga ctggaagcag gcctacaaa gccgcggcgg     6600
cccaattacc ggagacccta gagactatca tgctttgggg gttgctggga acagtctcgc    6660
tgggaatctt tttcgtcttg atgcggaaca agggcatagg gaagatgggc tttggaatgg    6720
```

```
tgactcttgg ggccagcgca tggcttatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagtg ggtcttctgg    6900
gcttgattac cgccaatgaa ctcggatggt tggagagaac aaagagtgac ctaagccatc    6960
taatgggaag gagagaggag ggggcaacta taggattctc aatggacatt gacctgcggc    7020
cagcctcagc ttgggctatc tatgctgctc tgacaacttt cattacccca gccgtccaac    7080
atgcagtgac cacttcatac aacaactact ccttaatggc gatggccacg caagctggag    7140
tgttgttcgg tatgggtaaa gggatgccat tctatgcatg ggactttgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc tgtctccagc gccatactgt cgcggaccgc ctgggggtgg ggtgaggctg    7500
gggccctgat cacagctgca acttccactt tgtgggaggg ctctccgaac aagtactgga    7560
actcctccac agccacctca ctgtgtaaca ttttagggg aagctacttg gctggagctt    7620
ctctaatcta cacagtaaca agaaacgctg gcttggtcaa gagacgtggg ggtgaacgg    7680 gagagaccct gggagagaaa tggaaggccc gcctgaacca gatgtcggcc ctggagttct    7740
actcctacaa aaagtcaggc atcaccgagg tgtgcagaga agaggcccgc cgcgccctca    7800
aggacggtgt ggcaacggga ggccacgctg tgtcccgagg aagtgcaaag ctgagatggt    7860
tggtggagag gggatacctg cagccctatg gaaaggtcat tgatcttgga tgtggcagag    7920
ggggctggag ttactatgcc gccaccatcc gcaaagttca agaagtgaaa ggatacacaa    7980
aaggaggccc tggtcatgaa gaacccatgt tggtgcaaag ctatgggtgg aacatagtcc    8040
gtcttaagag tgggggtgac gtcttttcata tggcggctga gccgtgtgac acgttgctgt    8100
gtgatatagg tgagtcatca tctagtcctg aagtggaaga agcacggacg ctcagagtcc    8160
tctccatggt gggggattgg cttgaaaaaa gaccaggagc cttttgtata aaagtgttgt    8220
gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctccttttg gggcgcatgg    8400
acgggcccag gaggccagtg aaatatgaag aggatgtgaa tctcggctct ggcacgcggg    8460
ctgtggtaag ctgcgctgaa gctcccaaca tgaagatcat tggtaaccgc attgagagga    8520
tccgcagtga gcacgcggaa acgtggttct ttgacgagaa ccacccatat aggacatggg    8580
cttaccatgg aagctacgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760
cagaccccca agaaggcact cgtcaggtta tgagcatggt ctcttcctgg ttgtggaaag    8820
agttaggcaa acacaaacgg ccacgagtct gtaccaaaga agagttcatc aacaaggttc    8880
gtagcaacgc agcattaggg gcaatatttg aagaggaaaa agagtggaag actgcagtgg    8940
aagctgtgaa cgatccaagg ttctgggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtacat gtggctaggg gctagatttc    9120
```

```
tagagttcga agcccttgga ttcttgaacg aggatcactg gatggggaga gagaattcag    9180
gaggtggtgt tgaagggcta ggattacaaa gactcggata tgtcttagaa gagatgagtc    9240
gcataccagg aggaaggatg tatgcagatg atactgctgg ctgggacacc cgcatcagca    9300
ggtttgatct ggagaatgaa gctctaatca ccaaccaaat ggagaaaggg cacagggcct    9360
tggcattggc cataatcaag tacacatacc aaaacaaagt ggtaaaggtc cttagaccag    9420
ctgaaaaagg gaagacagtt atggacatta tttcaagaca agaccaaagg gggagcggac    9480
aagttgtcac ttacgctctt aatacattta ccaacctagt ggtgcagctc attcggaata    9540
tggaggctga ggaagttcta gagatgcaag acttgtggct gctgcggagg tcagagaaag    9600
tgaccaactg gttgcagagc aatggatggg ataggctcaa acgaatggca gtcagtggag    9660
atgattgcgt tgtgaaacca attgatgata ggttttgcaca tgctctcagg ttcttgaatg    9720
atatgggaaa agttaggaag gacacacaag agtggaagcc ctcaactgga tgggacaact    9780
gggaagaagt tccgttttgc tcccaccact tcaacaagct ccatctcaag gacgggaggt    9840
ccattgtggt tccctgccgc caccaagatg aactgattgg ccgagctcgc gtctcaccgg    9900
gggcgggatg gagcatccgg gagactgctt gcctagcaaa atcatatgcg caaatgtggc    9960
agctccttta tttccacaga agggacctcc gactgatggc caatgccatt tgttcatctg   10020
tgccagttga ctgggttcca actgggagaa ctacctggtc aatccatgga aagggagaat   10080
ggatgaccac tgaagacatg cttgtggtgt ggaacagagt gtggattgag agaacgacc    10140 acatggaaga caagaccccca gttacgaaat ggacagacat tccctatttg ggaaaaaggg   10200
aagacttgtg gtgtgggtct ctcataggcc acagaccgcg caccacctgg gctgagaaca   10260
ttaaaaacac agtcaacatg atgcgtagga tcataggtga tgaagaaaag tacgtggact   10320
acctatccac ccaagttcgc tacttgggcg aagaagggtc cacacctgga gtgctataag   10380
caccaatctt agtgttgtca ggcctgctag tcagccacag cttggggaaa gctgtgcagc   10440
ctgtgacccc cccaggagaa gctgggaaac caagcccata gtcaggccga aacgccatg    10500 gcacggaaga agccatgctg cctgtgagcc cctcagagga cactgagtca aaaaccccca   10560
cgcgcttgga ggcgcaggat gggaaaagaa ggtggcgacc ttccccaccc tttaatctgg   10620
ggcctgaact ggagatcagc tgtggatctc cagaagaggg actagtggtt agaggagacc   10680 cccccggaaaa cgcaaaacag catattgacg ctggaaagaa ccagagactc catgagtttc   10740
caccacgctg gccgccaggc acagatcgcc gaatagcggc ggccggtgtg gggaaatcca   10800
tgggtctggg tcgcatggc atctccacct cctcgcggtc cgacctgggc tacttcggta    10860
ggctaaggga gaagaatcga tgctgtgcct tctagttgcc agccatctgt gtttgccccc    10920 tccccgtgc cttccttgac cctggaaggt gccactccca ctgtcctttc ctaataaaat    10980
gaggaaattg catcgcattg tctgagtagg tgtcattcta ttctgggggg tggggtgggg   11040
caggacagca agggggagga ttgggaagac aatagcaggc atgctgggga tgcggtgggc   11100
tctatgggcc cgggccgtcg accaattctc atgtttgaca gcttatcatc gaatttctgc   11160
cattcatccg cttattatca cttattcagg cgtagcaacc aggcgtttaa gggcaccaat   11220
aactgcctta aaaaaattac gccccgcccct gccactcatc gcagtactgt tgtaattcat   11280
taagcattct gccgacatgg aagccatcac aaacggcatg atgaacctga atcgccagcg   11340
gcatcagcac cttgtcgcct tgcgtataat atttgcccat ggtgaaaacg ggggcgaaga   11400
agttgtccat attggccacg tttaaatcaa aactggtgaa actcacccag ggattggctg   11460
```

```
agacgaaaaa catattctca ataaaccctt tagggaaata ggccaggttt tcaccgtaac   11520
acgccacatc ttgcgaatat atgtgtagaa actgccggaa atcgtcgtgg tattcactcc   11580
agagcgatga aaacgtttca gtttgctcat ggaaaacggt gtaacaaggg tgaacactat   11640
cccatatcac cagctcaccg tctttcattg ccatacgaaa ttccggatga gcattcatca   11700
ggcgggcaag aatgtgaata aaggccggat aaaacttgtg cttattttc tttacggtct    11760 ttaaaaaggc cgtaatatcc agctgaacgg tctggttata ggtacattga gcaactgact   11820
gaaatgcctc aaaatgttct ttacgatgcc attgggatat atcaacggtg gtatatccag   11880
tgattttttt ctccatttta gcttccttag ctcctgaaaa tctcgataac tcaaaaaata   11940
cgcccggtag tgatcttatt tcattatggt gaaagttgga acctcttacg tgccgatcaa   12000
cgtctcattt tcgccaaaag ttgggccagg gcttcccggt atcaacaggg acaccaggat   12060
ttatttattc tgcgaagtga tcttccgtca caggtattta ttcgcgataa gctcatggag   12120
cggcgtaacc gtcgcacagg aaggacagag aaagcgcgga tctgggaagt gacggacaga   12180
acggtcagga cctggattgg ggaggcggtt gccgccgctg ctgctgacgg tgtgacgttc   12240
tctgttccgg tcacaccaca tacgttccgc cattcctatg cgatgcacat gctgtatgcc   12300
ggtataccgc tgaaagttct gcaaagcctg atgggacata agtccatcag ttcaacggaa   12360
gtctacacga aggttttgc gctggatgtg gctgcccggc accgggtgca gtttgcgatg    12420
ccggagtctg atgcggttgc gatgctgaaa caattatcct gagaataaat gccttggcct   12480
ttatatggaa atgtggaact gagtggatat gctgttttg tctgttaaac agagaagctg    12540
gctgttatcc actgagaagc gaacgaaaca gtcgggaaaa tctcccatta tcgtagagat   12600
ccgcattatt aatctcagga gcctgtgtag cgtttatagg aagtagtgtt ctgtcatgat   12660
gcctgcaagc ggtaacgaaa acgatttgaa tatgccttca ggaacaatag aaatcttcgt   12720
gcggtgttac gttgaagtgg agcggattat gtcagcaatg gacagaacaa cctaatgaac   12780
acagaaccat gatgtggtct gtcctttac agccagtagt gctcgccgca gtcgagcgac    12840
agggcgaagc cctcggctgg ttgccctcgc cgctgggctg gcggccgtct atggccctgc   12900
aaacgcgcca gaaacgccgt cgaagccgtg tgcgagacac cgcggccggc cgccggcgtt   12960
gtggatacct cgcggaaaac ttggccctca ctgacagatg aggggcggac gttgacactt   13020
gaggggccga ctcacccggc gcggcgttga cagatgaggg gcaggctcga tttcggccgg   13080
cgacgtggag ctgccagcc tcgcaaatcg gcgaaaacgc ctgattttac gcgagtttcc     13140
cacagatgat gtgacaagc ctgggataa gtgccctgcg gtattgacac ttgaggggcg     13200
cgactactga cagatgaggg gcgcgatcct tgacacttga ggggcagagt gctgacagat   13260
gaggggcgca cctattgaca tttgagggg tgtccacagg cagaaaatcc agcatttgca    13320
agggtttccg cccgtttttc ggccaccgct aacctgtctt ttaacctgct tttaaaccaa   13380
tatttataaa ccttgttttt aaccagggct gcgccctgtg cgcgtgaccg cgcacgccga   13440 agggggtgc cccccttct cgaaccctcc cggtcgagtg agcgaggaag caccagggaa     13500
cagcacttat atattctgct tacacacgat gcctgaaaaa acttcccttg gggttatcca   13560
cttatccacg gggatatttt tataattatt ttttttatag ttttttagatc ttcttttta   13620 gagcgccttg taggcctta tccatgctgg ttctagagaa ggtgttgtga caaattgccc    13680
tttcagtgtg acaaatcacc ctcaaatgac agtcctgtct gtgacaaatt gcccttaacc   13740
ctgtgacaaa ttgccctcag aagaagctgt ttttcacaa agttatccct gcttattgac    13800
tcttttttat ttagtgtgac aatctaaaaa cttgtcacac ttcacatgga tctgtcatgg   13860
```

```
cggaaacagc ggttatcaat cacaagaaac gtaaaaatag cccgcgaatc gtccagtcaa   13920
acgacctcac tgaggcggca tatagtctct cccgggatca aaaacgtatg ctgtatctgt   13980
tcgttgacca gatcagaaaa tctgatggca ccctacagga acatgacggt atctgcgaga   14040
tccatgttgc taaatatgct gaaatattcg gattgacctc tgcggaagcc agtaaggata   14100
tacggcaggc attgaagagt ttcgcgggga aggaagtggt tttttatcgc cctgaagagg   14160
atgccggcga tgaaaaaggc tatgaatctt ttccttggtt tatcaaacgt gcgcacagtc   14220
catccagagg gctttacagt gtacatatca acccatatct cattcccttc tttatcgggt   14280
tacagaaccg gtttacgcag tttcggctta gtgaaacaaa agaaatcacc aatccgtatg   14340
ccatgcgttt atacgaatcc ctgtgtcagt atcgtaagcc ggatggctca ggcatcgtct   14400
ctctgaaaat cgactggatc atagagcgtt accagctgcc tcaaagttac cagcgtatgc   14460
ctgacttccg ccgccgcttc ctgcaggtct gtgttaatga gatcaacagc agaactccaa   14520
tgcgcctctc atacattgag aaaagaaag gccgccagac gactcatatc gtattttcct   14580
tccgcgatat cacttccatg acgacaggat agtctgaggg ttatctgtca cagatttgag   14640
ggtggttcgt cacatttgtt ctgacctact gagggtaatt tgtcacagtt ttgctgtttc   14700
cttcagcctg catggatttt ctcatacttt ttgaactgta attttaagg aagccaaatt   14760 tgagggcagt ttgtcacagt tgatttcctt ctctttccct tcgtcatgtg acctgatatc   14820
gggggttagt tcgtcatcat tgatgagggt tgattatcac agtttattac tctgaattgg   14880
ctatccgcgt gtgtacctct acctggagtt ttttcccacgg tggatatttc ttcttgcgct   14940
gagcgtaaga gctatctgac agaacagttc ttctttgctt cctcgccagt tcgctcgcta   15000
tgctcggtta cacggctgcg gcgagcgcta gtgataataa gtgactgagg tatgtgctct   15060
tcttatctcc ttttgtagtg ttgctcttat tttaaacaac tttgcggttt tttgatgact   15120
ttgcgatttt gttgttgctt tgcagtaaat tgcaagattt aataaaaaaa cgcaaagcaa   15180
tgattaaagg atgttcagaa tgaaactcat ggaaacactt aaccagtgca taaacgctgg   15240
tcatgaaatg acgaaggcta tcgccattgc acagtttaat gatgacagcc cggaagcgag   15300
gaaaataacc cggcgctgga gaataggtga agcagcggat ttagttgggg tttcttctca   15360
ggctatcaga gatgccgaga aagcagggcg actaccgcac ccggatatgg aaattcgagg   15420
acgggttgag caacgtgttg gttatacaat tgaacaaatt aatcatatgc gtgatgtgtt   15480
tggtacgcga ttgcgacgtg ctgaagacgt atttccaccg gtgatcgggg ttgctgccca   15540
taaaggtggc gtttacaaaa cctcagtttc tgttcatctt gctcaggatc tggctctgaa   15600
ggggctacgt gttttgctcg tggaaggtaa cgaccccag ggaacagcct caatgtatca   15660
cggatgggta ccagatcttc atattcatgc agaagacact ctcctgcctt tctatcttgg   15720
ggaaaaggac gatgtcactt atgcaataaa gcccacttgc tggccggggc ttgacattat   15780
tccttcctgt ctggctctgc accgtattga aactgagtta atgggcaaat tgatgaagg   15840 taaactgccc accgatccac acctgatgct ccgactggcc attgaaactg ttgctcatga   15900
ctatgatgtc atagttattg acagcgcgcc taacctgggt atcggcacga ttaatgtcgt   15960
atgtgctgct gatgtgctga ttgttccac gcctgctgag ttgtttgact acacctccgc   16020
actgcagttt ttcgatatgc ttcgtgatct gctcaagaac gttgatctta aagggttcga   16080
gcctgatgta cgtattttgc ttaccaaata cagcaatagt aatggctctc agtccccgtg   16140
gatggaggag caaattcggg atgcctgggg aagcatggtt ctaaaaaatg ttgtacgtga   16200
```

```
aacggatgaa gttggtaaag gtcagatccg gatgagaact gttttttgaac aggccattga    16260
tcaacgctct tcaactggtg cctggagaaa tgctctttct atttgggaac ctgtctgcaa    16320
tgaaattttc gatcgtctga ttaaaccacg ctgggagatt agataatgaa gcgtgcgcct    16380
gttattccaa aacatacgct caatactcaa ccggttgaag atacttcgtt atcgacacca    16440
gctgccccga tggtggattc gttaattgcg cgcgtaggag taatggctcg cggtaatgcc    16500
attactttgc ctgtatgtgg tcgggatgtg aagtttactc ttgaagtgct ccggggtgat    16560
agtgttgaga agacctctcg ggtatggtca ggtaatgaac gtgaccagga gctgcttact    16620
gaggacgcac tggatgatct catcccttct tttctactga ctggtcaaca gacaccggcg    16680
ttcggtcgaa gagtatctgg tgtcatagaa attgccgatg ggagtcgccg tcgtaaagct    16740
gctgcactta ccgaaagtga ttatcgtgtt ctggttggcg agctggatga tgagcagatg    16800
gctgcattat ccagattggg taacgattat cgcccaacaa gtgcttatga acgtggtcag    16860
cgttatgcaa gccgattgca gaatgaattt gctggaaata tttctgcgct ggctgatgcg    16920
gaaaatattt cacgtaagat tattacccgc tgtatcaaca ccgccaaatt gcctaaatca    16980
gttgttgctc ttttttctca ccccggtgaa ctatctgccc ggtcaggtga tgcacttcaa    17040
aaagccttta cagataaaga ggaattactt aagcagcagg catctaacct tcatgagcag    17100
aaaaaagctg gggtgatatt tgaagctgaa gaagttatca ctcttttaac ttctgtgctt    17160
aaaacgtcat ctgcatcaag aactagttta agctcacgac atcagtttgc tcctggagcg    17220
acagtattgt ataagggcga taaaatggtg cttaacctgg acaggtctcg tgttccaact    17280
gagtgtatag agaaaattga ggccattctt aaggaacttg aaaagccagc accctgatgc    17340
gaccacgttt tagtctacgt ttatctgtct ttacttaatg tcctttgtta caggccagaa    17400
agcataactg gcctgaatat tctctctggg cccactgttc cacttgtatc gtcggtctga    17460
taatcagact gggaccacgg tcccactcgt atcgtcggtc tgattattag tctgggacca    17520
cggtcccact cgtatcgtcg gtctgattat tagtctggga ccacggtccc actcgtatcg    17580
tcggtctgat aatcagactg gaccacggt cccactcgta tcgtcggtct gattattagt    17640
ctgggaccat ggtcccactc gtatcgtcgg tctgattatt agtctgggac cacggtccca    17700
ctcgtatcgt cggtctgatt attagtctgg aaccacggtc ccactcgtat cgtcggtctg    17760
attattagtc tgggaccacg gtcccactcg tatcgtcggt ctgattatta gtctgggacc    17820
acgatcccac tcgtgttgtc ggtctgatta tcggtctggg accacggtcc cacttgtatt    17880
gtcgatcaga ctatcagcgt gagactacga ttccatcaat gcctgtcaag ggcaagtatt    17940
gacatgtcgt cgtaacctgt agaacggagt aacctcggtg tgcggttgta tgcctgctgt    18000
ggattgctgc tgtgtcctgc ttatccacaa cattttgcgc acggttatgt ggacaaaata    18060
cctggttacc caggccgtgc cggcacgtta accgttacat aacttacggt aaatggcccg    18120
cctggctgac cgcccaacga cccccgccca ttgacgtcaa taatgacgta tgttcccata    18180
gtaacgccaa tagggacttt ccattgacgt caatgggtgg agtatttacg gtaaactgcc    18240
cacttggcag tacatcaagt gtatcatatg ccaagtacgc cccctattga cgtcaatgac    18300
ggtaaatggc ccgcctggca ttatgcccag tacatgacct tatgggactt tcctacttgg    18360
cagtacatct acgtattagt catcgctatt accatggtga tgcggttttg gcagtacatc    18420
aatgggcgtg gatagcggtt tgactcacgg ggatttccaa gtctccaccc cattgacgtc    18480
aatgggagtt tgttttggca ccaaaatcaa cgggactttc caaaatgtcg taacaactcc    18540
gccccattga cgcaaatggg cggtaggcgt gtacggtggg aggtctatat aagcagagct    18600
```
ctctggctaa c                                                  18611

<210> SEQ ID NO 7
<211> LENGTH: 18258
<212> TYPE: DNA
<213> ORGANISM: Artificial Sequence
<220> FEATURE:
<223> OTHER INFORMATION: SV40 ZIKV FL sequence

<400> SEQUENCE: 7

```
agttgttgat ctgtgtgaat cagactgcga cagttcgagt ttgaagcgaa agctagcaac     60
agtatcaaca ggttttattt tggatttgga acgagagtt tctggtcatg aaaaacccaa    120
agaagaaatc cggaggattc cggattgtca atatgctaaa acgcggagta gcccgtgtga    180
gccccttggg gggcttgaag aggctgccag ccggacttct gctgggtcat gggcccatca    240
ggatggtctt ggcgattcta gccttttga gattcacggc aatcaagcca tcactgggtc    300
tcatcaatag atggggttca gtggggaaaa aagaggctat ggaataata agaagttta    360
agaaagatct ggctgccatg ctgagaataa tcaatgctag gaaggagaag aagagacgag    420
gcacagatac tagtgtcgga attgttggcc tcctgctgac cacagccatg gcagtggagg    480
tcactagacg tgggaatgca tactatatgt acttggacag aagcgatgct ggggaggcca    540
tatcttttcc aaccacaatg gggatgaata agtgttatat acagatcatg gatcttggac    600
acatgtgtga tgccaccatg agctatgaat gccctatgct ggatgagggg gtagaaccag    660
atgacgtcga ttgttggtgc aacacgacgt caacttgggt tgtgtacgga acctgccacc    720
acaaaaaagg tgaagcacgg agatctagaa gagctgtgac gctcccctcc cattccacta    780
ggaagctgca acgcggtcg cagacctggt tggaatcaag agaatacaca agcacctga    840
ttagagtcga aaattggata tcaggaacc ctggcttcgc gttagcagca gctgccatcg    900
cttggcttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtt accgtaatgg   1080
cacaggacaa accgactgtc gacatagagc tggttacaac aacagtcagc aacatggcgg   1140
aggtaagatc ctactgctat gaggcatcaa tatcggacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcttgc tctaagaaaa tgaccgggaa gagcatccag ccagagaatc   1380
tggagtaccg gataatgctg tcagttcatg gctcccagca cagtgggatg atcgttaatg   1440
atacaggaca tgaaactgat gagaatagag cgaaggttga gataacgccc aattcaccaa   1500
gagccgaagc caccctgggg ggttttgaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcagactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggacaaact tagattgaag ggcgtgtcat actccttgtg taccgcagcg ttcacattca   1920
ctaagatccc ggctgaaaca ctgcacggga cagtcacagt ggaggtacag tacgcaggga   1980
```

```
cagatggacc ttgcaaggtt ccagctcaga tggcggtgga catgcaaact ctgaccccag    2040
ttgggaggtt gataaccgct aaccctgtaa tcactgaaag cactgagaac tccaagatga    2100
tgctggaact ggatccacca tttggggact cttacattgt cataggagtc ggggaaaaga    2160
agatcaccca ccactggcac aggagtggca gcaccattgg aaaagcattt gaagccactg    2220
tgagaggtgc caagagaatg gcagtcttgg agacacagc ctgggacttt ggatcagttg     2280
ggggtgctct caactcactg gcaagggca tccatcaaat ttttggagca gctttcaaat     2340
cattgtttgg aggaatgtcc tggttctcac aaattctcat tggaacgttg ctggtgtggt    2400
tgggtctgaa tacaaagaat ggatctattt cccttatgtg cttggcctta ggggagtgt     2460 tgatcttctt atccacagcc gtctctgctg atgtggggtg ctcggtggac ttctcaaaga    2520
aggaaacgag atgcgtaca ggggtgttcg tctataacga cgttgaagct ggagggaca      2580 ggtacaagta ccatcctgac tcccctcgta gattggcagc agcagtcaag caagcctggg    2640
aagatgggat ctgtgggatc tcctctgttt caagaatgga aaacatcatg tggagatcag    2700
tagaagggga gctcaacgca atcctggaag agaatggagt tcaactgacg gtcgttgtgg    2760
gatctgtaaa aaaccccatg tggagaggtc cacagagatt gcccgtgcct gtgaacgagc    2820
tgccccatgg ctggaaggct tgggggaaat cgtacttcgt cagggcagca agacaaata    2880 acagctttgt cgtggatggt gacacactga aggaatgccc actcaaacat agagcatgga    2940
acagcttcct tgtggaggat catgggttcg gggtatttca cactagtgtc tggctcaagg    3000
ttagagaaga ttattcactc gagtgtgatc cagccgtcat tggaacagcc gctaagggaa    3060
aggaggctgt gcacagtgat ctaggctact ggattgagag tgagaagaac gacacatgga    3120
ggctgaagag ggcccacctg atcgagatga aaacatgtga atggccaaag tcccacacat    3180 tgtgacaga tggaatagaa gaagtgatc tgatcatacc caagtctta gctgggccac       3240 tcagccatca aacaccaga gagggctaca ggacccaaat gaaagggcca tggcatagtg     3300
aagagcttga aattcggttt gaggaatgcc caggcactaa ggtccacgtg gaggaaacat    3360
gtggaacaag aggaccatct ctgagatcaa ccactgcaag cggaagggtg atcgaggaat    3420
ggtgctgcag ggagtgcaca atgcccccac tgtcgttccg ggctaaagat ggttgttggt    3480
atggaatgga gataaggccc aggaaagaac cagaaagtaa cttagtaagg tcaatggtga    3540
ctgcaggatc aactgatcac atggatcact tctcccttgg agtgcttgtg attctgctca    3600
tggtacagga agggctaaag aagagaatga ccacaaagat catcataagc acatcaatgg    3660
cagtgctggt agctatgatc ctgggaggat tttcaatgag tgacctggct aagcttgcaa    3720
ttttgatggg tgccaccttc gcggaaatga acactggagg agatgttgct catctggcgc    3780
tgatagcggc attcaaagtc agacctgcgt tgctggtatc tttcattttc agagctaatt    3840
ggacaccccg tgagagcatg ctgctggcct tggcctcgtg tcttctgcaa actgcgatct    3900
ccgccttgga aggcgacctg atggttccca tcaatggttt tgctttggcc tggttggcaa    3960
tacgagcgat ggttgttcca cgcactgaca acatcacctt ggcaatcctg ctgctctga    4020 caccactggc ccggggcaca ctgcttgtgg cgtggagagc aggccttgct acttgcgggg    4080
ggttcatgct cctttctctg aaggggaaag gcagtgtgaa gaagaactta ccatttgtca    4140
tggccctggg actaaccgct gtgaggctgg tcgacccca t caacgtggtg ggactgctgt    4200
tgctcacaag gagtgggaag cggagctggc cccctagtga agtactcaca gctgttggcc    4260
tgatatgcgc attggctgga gggttcgcca aggcggatat agagatggct gggcccatgg    4320
ccgcggtcgg tctgctaatt gtcagttacg tggtctcagg aaagagtgtg gacatgtaca    4380
```

```
ttgaaagagc aggtgacatc acatgggaaa aagatgcgga agtcactgga aacagtcccc    4440
ggctcgatgt ggcactagat gagagtggtg atttctccct agtggaggat gatggtcccc    4500
ccatgagaga gatcatactc aaagtggtcc tgatggccat ctgtggcatg aacccaatag    4560
ccataccctt tgcagctgga gcgtggtacg tgtatgtgaa gactggaaaa aggagtggtg    4620
ctctatggga tgtgcctgct cccaaggaag taaaaaggg ggagaccaca gatggagtgt    4680
acagagtaat gactcgtaga ctgctaggtt caacacaagt tggagtggga gtcatgcaag    4740
agggggtctt ccacactatg tggcacgtca caaaaggatc cgcgctgaga agcggtgaag    4800
ggagacttga tccatactgg ggagatgtca agcaggatct ggtgtcatac tgtggtccat    4860
ggaagctaga tgccgcctgg gacgggcaca gcgaggtgca gctcttggcc gtgccccccg    4920
gagagagagc gaggaacatc cagactctgc ccggaatatt taagacaaag gatgggggaca    4980 ttggagcagt tgcgctggac tacccagcag gtacctcagg atctccaatc ctagataagt    5040
gtgggagagt gataggactc tatggtaatg ggtcgtgat caaaaatggg agttacgtta    5100
gtgccatcac ccaagggagg agggaggaag agactcctgt tgagtgcttc gagccttcga    5160
tgctgaagaa gaagcagcta actgtcttag acttgcatcc tggagctggg aaaaccagga    5220
gagttcttcc tgaaatagtc cgtgaagcca taaaaacaag actccgcact gtgatcttag    5280
ctccaaccag ggttgtcgct gctgaaatgg aggaagccct tagagggctt ccagtgcgtt    5340
atatgacaac agcagtcaat gtcacccatt ctgggacaga aatcgttgac ttaatgtgcc    5400
atgccacctt cacttcacgt ctactacagc caatcagagt ccccaactat aatctgtata    5460
ttatggatga ggcccacttc acagatccct caagtatagc agcaagagga tacatttcaa    5520
caagggttga gatgggcgag gcggctgcca tcttcatgac tgccacgcca ccaggaaccc    5580
gtgacgcatt cccggactcc aactcaccaa ttatggacac cgaagtggaa gtcccagaga    5640
gagcctggag ctcaggcttt gattgggtga cggatcattc tggaaaaaca gtttggtttg    5700
ttccaagcgt gaggaatggc aatgagatcg cagcttgtct gacaaaggct ggaaaacggg    5760
tcatacagct cagcagaaag actttttgaga cagagttcca gaaaacaaaa catcaagagt    5820
gggacttcgt cgtgacaact gacatttcag agatgggcgc caactttaaa gctgaccgtg    5880
tcatagattc caggagatgc ctaaagccgg tcatacttga tggcgagaga gtcattctgg    5940
ctggacccat gcctgtcaca catgccagcg ctgcccagag gaggggggcgc ataggcagga    6000 accccaacaa acctggagat gagtatctgt atggaggtgg gtgcgcagag actgatgaag    6060
accatgcaca ctggcttgaa gcaagaatgc ttcttgacaa catttacctc caagatggcc    6120
tcatagcctc gctctatcga cctgaggccg acaaagtagc agctattgag ggagagttca    6180
agcttaggac ggagcaaagg aagaccttg tggaactcat gaaaagagga gatcttcctg    6240
tttggctggc ctatcaggtt gcatctgccg gaataaccta cacagataga agatggtgct    6300
ttgatggcac gaccaacaac accataatgg aagacagtgt gccggcagag gtgtggacca    6360
gatacggaga gaaaagagtg ctcaaaccga ggtggatgga cgccagagtt tgttcagatc    6420
atgcggccct gaagtcattc aaagagtttg ccgctgggaa aagaggagcg cctttggag    6480 tgatggaagc cctgggaaca ctgccaggac atatgacaga gagattccag gaggccattg    6540
acaacctcgc tgtgctcatg cgggcagaga ctggaagcag ccctacaaa gccgcggcgg    6600 cccaattacc ggagacccta gagactatca tgcttttggg gttgctggga acagtctcgc    6660
tgggaatctt tttcgtcttg atgcggaaca agggcatagg gaagatgggc tttggaatgg    6720
```

```
tgactcttgg ggccagcgca tggcttatgt ggctctcgga aattgagcca gccagaattg    6780
catgtgtcct cattgttgtg ttcctattgc tggtggtgct catacctgag ccagaaaagc    6840
aaagatctcc ccaggacaac caaatggcaa tcatcatcat ggtagcagtg ggtcttctgg    6900
gcttgattac cgccaatgaa ctcggatggt tggagagaac aaagagtgac ctaagccatc    6960
taatgggaag gagagaggag ggggcaacta taggattctc aatggacatt gacctgcggc    7020
cagcctcagc ttgggctatc tatgctgctc tgacaacttt cattacccca gccgtccaac    7080
atgcagtgac cacttcatac aacaactact ccttaatggc gatggccacg caagctggag    7140
tgttgttcgg tatgggtaaa gggatgccat tctatgcatg ggactttgga gtcccgctgc    7200
taatgatagg ttgctactca caattaacac ccctgaccct aatagtggcc atcattttgc    7260
tcgtggcgca ctacatgtac ttgatcccag ggctgcaggc agcagctgcg cgtgctgccc    7320
agaagagaac ggcagctggc atcatgaaga accctgttgt ggatggaata gtggtgactg    7380
acattgacac aatgacaatt gacccccaag tggagaaaaa gatgggacag gtgctactca    7440
tagcagtagc tgtctccagc gccatactgt cgcggaccgc ctgggggtgg ggtgaggctg    7500
gggccctgat cacagctgca acttccactt tgtgggaggg ctctccgaac aagtactgga    7560
actcctccac agccacctca ctgtgtaaca ttttttagggg aagctacttg gctggagctt    7620
ctctaatcta cacagtaaca agaaacgctg gcttggtcaa gagacgtggg ggtgaacgg    7680 gagagaccct gggagagaaa tggaaggccc gcctgaacca gatgtcggcc ctggagttct    7740
actcctacaa aaagtcaggc atcaccgagg tgtgcagaga agaggcccgc cgcgccctca    7800
aggacggtgt ggcaacggga ggccacgctg tgtcccgagg aagtgcaaag ctgagatggt    7860
tggtggagag gggataccctg cagccctatg gaaaggtcat tgatcttgga tgtggcagag    7920
ggggctggag ttactatgcc gccaccatcc gcaaagttca agaagtgaaa ggatacacaa    7980
aaggaggccc tggtcatgaa gaacccatgt tggtgcaaag ctatgggtgg aacatagtcc    8040
gtcttaagag tggggtggac gtcttttcata tggcggctga gccgtgtgac acgttgctgt    8100
gtgatatagg tgagtcatca tctagtcctg aagtggaaga agcacggacg ctcagagtcc    8160
tctccatggt gggggattgg cttgaaaaaa gaccaggagc ctttttgtata aaagtgttgt    8220 gcccatacac cagcactatg atggaaaccc tggagcgact gcagcgtagg tatgggggag    8280
gactggtcag agtgccactc tcccgcaact ctacacatga gatgtactgg gtctctggag    8340
cgaaaagcaa caccataaaa agtgtgtcca ccacgagcca gctccttttg gggcgcatgg    8400
acgggcccag gaggccagtg aaatatgaag gaggatgtgaa tctcggctct ggcacgcggg    8460
ctgtggtaag ctgcgctgaa gctcccaaca tgaagatcat tggtaaccgc attgagagga    8520
tccgcagtga gcacgcggaa acgtggttct tgacgagaa ccacccatat aggacatggg    8580
cttaccatgg aagctacgag gcccccacac aagggtcagc gtcctctcta ataaacgggg    8640
ttgtcaggct cctgtcaaaa ccctgggatg tggtgactgg agtcacagga atagccatga    8700
ccgacaccac accgtatggt cagcaaagag ttttcaagga aaaagtggac actagggtgc    8760 cagacccca agaaggcact cgtcaggtta tgagcatggt ctcttcctgg ttgtggaaag    8820
agttaggcaa acacaaacgg ccacgagtct gtaccaaaga agagttcatc aacaaggttc    8880
gtagcaacgc agcattaggg gcaatatttg aagaggaaaa gagtggaag actgcagtgg    8940 aagctgtgaa cgatccaagg ttctggggctc tagtggacaa ggaaagagag caccacctga    9000
gaggagagtg ccagagctgt gtgtacaaca tgatgggaaa aagagaaaag aaacaagggg    9060
aatttggaaa ggccaagggc agccgcgcca tctggtacat gtggctaggg gctagatttc    9120
```

```
tagagttcga agcccttgga ttcttgaacg aggatcactg gatggggaga gagaattcag   9180
gaggtggtgt tgaagggcta ggattacaaa gactcggata tgtcttagaa gagatgagtc   9240
gcataccagg aggaaggatg tatgcagatg atactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcaagaca agaccaaagg gggagcggac   9480
aagttgtcac ttacgctctt aatacattta ccaacctagt ggtgcagctc attcggaata   9540
tggaggctga ggaagttcta gagatgcaag acttgtggct gctgcggagg tcagagaaag   9600
tgaccaactg gttgcagagc aatggatggg ataggctcaa acgaatggca gtcagtggag   9660
atgattgcgt tgtgaaacca attgatgata ggtttgcaca tgctctcagg ttcttgaatg   9720
atatgggaaa agttaggaag gacacacaag agtggaagcc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgagctcgc gtctcaccgg   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag agaacgacc   10140 acatggaaga caagccccca gttacgaaat ggacagacat tccctatttg ggaaaaaggg  10200
aagacttgtg gtgtgggtct ctcataggg cacagaccgcg caccacctgg gctgagaaca  10260
ttaaaaacac agtcaacatg atgcgtagga tcataggtga tgaagaaaag tacgtggact  10320
acctatccac ccaagttcgc tacttgggcg aagaagggtc cacacctgga gtgctataag  10380
caccaatctt agtgttgtca ggcctgctag tcagccacag cttggggaaa gctgtgcagc  10440
ctgtgacccc cccaggagaa gctgggaaac caagcccata gtcaggccga aacgccatg   10500 gcacggaaga agccatgctg cctgtgagcc cctcagagga cactgagtca aaaaccccca  10560
cgcgcttgga ggcgcaggat gggaaaagaa ggtggcgacc ttccccaccc tttaatctgg  10620
ggcctgaact ggagatcagc tgtggatctc cagaagaggg actagtggtt agaggagacc  10680
ccccggaaaa cgcaaaacag catattgacg ctgggaaaga ccagagactc catgagtttc  10740
caccacgctg gccgccaggc acagatcgcc gaatagcggc ggccggtgtg gggaaatcca  10800
tgggtctggg tcggcatggc atctccacct cctcgcggtc cgacctgggc tacttcggta  10860
ggctaaggga gaagaatcga tgaacttgtt tattgcagct tataatggtt acaaataaag  10920
caatagcatc acaaatttca caaataaagc atttttttca ctgcattcta gttgtggttt  10980
gtccaaactc atcaatgtat cttatgcccg ggccgtcgac caattctcat gtttgacagc  11040
ttatcatcga atttctgcca ttcatccgct tattatcact tattcaggcg tagcaaccag  11100
gcgtttaagg gcaccaataa ctgccttaaa aaaattacgc cccgccctgc cactcatcgc  11160
agtactgttg taattcatta agcattctgc cgacatggaa gccatcacaa acggcatgat  11220
gaacctgaat cgccagcggc atcagcacct tgtcgccttg cgtataatat ttgcccatgg  11280
tgaaaacggg ggcgaagaag ttgtccatat tggccacgtt taaatcaaaa ctggtgaaac  11340
tcacccaggg attggctgag acgaaaaaca tattctcaat aaaccccttta gggaaatagg  11400 ccaggttttc accgtaacac gccacatctt gcgaatatat gtgtagaaac tgccggaaat  11460
```

```
cgtcgtggta ttcactccag agcgatgaaa acgtttcagt ttgctcatgg aaaacggtgt    11520
aacaagggtg aacactatcc catatccacca gctcaccgtc tttcattgcc atacgaaatt    11580
ccggatgagc attcatcagg cgggcaagaa tgtgaataaa ggccggataa aacttgtgct    11640
tattttcctt tacggtcttt aaaaaggccg taatatccag ctgaacggtc tggttatagg    11700
tacattgagc aactgactga aatgcctcaa aatgttcttt acgatgccat tgggatatat    11760
caacggtggt atatccagtg attttttct ccattttagc ttccttagct cctgaaaatc    11820
tcgataactc aaaaaatacg cccggtagtg atcttatttc attatggtga agttggaac    11880 ctcttacgtg ccgatcaacg tctcattttc gccaaaagtt ggcccagggc ttcccggtat    11940
caacagggac accaggattt atttattctg cgaagtgatc ttccgtcaca ggtatttatt    12000
cgcgataagc tcatggagcg gcgtaaccgt cgcacaggaa ggacagagaa agcgcggatc    12060
tgggaagtga cggacagaac ggtcaggacc tggattgggg aggcggttgc cgccgctgct    12120
gctgacggtg tgacgttctc tgttccggtc acaccacata cgttccgcca ttcctatgcg    12180
atgcacatgc tgtatgccgg tataccgctg aaagttctgc aaagcctgat gggacataag    12240
tccatcagtt caacggaagt ctacacgaag ttttttgcgc tggatgtggc tgcccggcac    12300
cgggtgcagt ttgcgatgcc ggagtctgat gcggttgcga tgctgaaaca attatcctga    12360
gaataaatgc cttggccttt atatggaaat gtggaactga gtggatatgc tgttttgtc    12420 tgttaaacag agaagctggc tgttatccac tgagaagcga acgaaacagt cgggaaaatc    12480
tcccattatc gtagagatcc gcattattaa tctcaggagc ctgtgtagcg tttataggaa    12540
gtagtgttct gtcatgatgc ctgcaagcgg taacgaaaac gatttgaata tgccttcagg    12600
aacaatagaa atcttcgtgc ggtgttacgt tgaagtggag cggattatgt cagcaatgga    12660
cagaacaacc taatgaacac agaaccatga tgtggtctgt ccttttacag ccagtagtgc    12720
tcgccgcagt cgagcgacag ggcgaagccc tcggctggtt gccctcgccg ctgggctggc    12780
ggccgtctat ggccctgcaa acgcgccaga acgccgtcg aagccgtgtg cgagacaccg    12840
cggccggccg ccggcgttgt ggatacctcg cggaaaactt ggccctcact gacagatgag    12900
gggcggacgt tgacacttga ggggccgact caccgcgc ggcgttgaca gatgaggggc    12960
aggctcgatt tcggccggcg acgtggagct ggccagcctc gcaaatcggc gaaaacgcct    13020
gattttacgc gagtttccca cagatgatgt ggacaagcct ggggataagt gccctgcggt    13080
attgacactt gaggggcgcg actactgaca gatgaggggc gcgatccttg acacttgagg    13140
ggcagagtgc tgacagatga ggggcgcacc tattgacatt tgaggggctg tccacaggca    13200
gaaaatccag catttgcaag ggtttccgcc cgttttcgg ccaccgctaa cctgtctttt    13260
aacctgcttt taaccaata tttataaacc ttgtttttaa ccaggctgc gcctgtgcg    13320 cgtgaccgcg cacgccgaag gggggtgccc ccccttctcg aaccctcccg gtcgagtgag    13380
cgaggaagca ccaggaaca gcacttatat attctgctta cacgatgc ctgaaaaac    13440 ttcccttggg gttatccact tatccacggg gatatttta taattatttt ttttatagtt    13500
tttagatctt ctttttaga gcgccttgta ggcctttatc catgctggtt ctagagaagg    13560
tgttgtgaca aattgccctt tcagtgtgac aaatcaccct caaatgacag tcctgtctgt    13620
gacaaattgc ccttaaccct gtgacaaatt gccctcagaa gaagctgttt tttcacaaag    13680
ttatccctgc ttattgactc tttttttattt agtgtgacaa tctaaaaact tgtcacactt    13740
cacatggatc tgtcatggcg gaaacagcgg ttatcaatca aagaaacgt aaaaatagcc    13800 cgcgaatcgt ccagtcaaac gacctcactg aggcggcata tagtctctcc cgggatcaaa    13860
```

```
aacgtatgct gtatctgttc gttgaccaga tcagaaaatc tgatggcacc ctacaggaac   13920
atgacggtat ctgcgagatc catgttgcta aatatgctga aatattcgga ttgacctctg   13980
cggaagccag taaggatata cggcaggcat tgaagagttt cgcggggaag gaagtggttt   14040
tttatcgccc tgaagaggat gccggcgatg aaaaaggcta tgaatctttt ccttggttta   14100
tcaaacgtgc gcacagtcca tccagagggc tttacagtgt acatatcaac ccatatctca   14160
ttcccttctt tatcgggtta cagaaccggt ttacgcagtt tcggcttagt gaaacaaaag   14220
aaatcaccaa tccgtatgcc atgcgtttat acgaatccct gtgtcagtat cgtaagccgg   14280
atggctcagg catcgtctct ctgaaaatcg actggatcat agagcgttac cagctgcctc   14340
aaagttacca gcgtatgcct gacttccgcc gccgcttcct gcaggtctgt gttaatgaga   14400
tcaacagcag aactccaatg cgcctctcat acattgagaa aaagaaaggc cgccagacga   14460
ctcatatcgt attttccttc cgcgatatca cttccatgac gacaggatag tctgagggtt   14520
atctgtcaca gatttgaggg tggttcgtca catttgttct gacctactga gggtaatttg   14580
tcacagtttt gctgtttcct tcagcctgca tggattttct catactttt gaactgtaat   14640 ttttaaggaa gccaaatttg agggcagttt gtcacagttg atttccttct ctttcccttc   14700
gtcatgtgac ctgatatcgg gggttagttc gtcatcattg atgagggttg attatcacag   14760
tttattactc tgaattggct atccgcgtgt gtacctctac ctggagtttt tcccacggtg   14820
gatatttctt cttgcgctga gcgtaagagc tatctgacag aacagttctt ctttgcttcc   14880
tcgccagttc gctcgctatg ctcggttaca cggctgcggc gagcgctagt gataataagt   14940
gactgaggta tgtgctcttc ttatctcctt ttgtagtgtt gctcttattt taaacaactt   15000
tgcggttttt tgatgacttt gcgattttgt tgttgctttg cagtaaattg caagatttaa   15060
taaaaaaacg caaagcaatg attaaaggat gttcagaatg aaactcatgg aaacacttaa   15120
ccagtgcata aacgctggtc atgaaatgac gaaggctatc gccattgcac agtttaatga   15180
tgacagcccg gaagcgagga aaataacccg gcgctggaga ataggtgaag cagcggattt   15240 agttgggggtt tcttctcagg ctatcagaga tgccgagaaa gcagggcgac taccgcaccc   15300
ggatatggaa attcgaggac gggttgagca acgtgttggt tatacaattg aacaaattaa   15360
tcatatgcgt gatgtgtttg gtacgcgatt gcgacgtgct gaagacgtat ttccaccggt   15420 gatcgggggtt gctgcccata aaggtggcgt ttacaaaacc tcagtttctg ttcatcttgc   15480
tcaggatctg gctctgaagg ggctacgtgt tttgctcgtg gaaggtaacg accccagggg   15540
aacagcctca atgtatcacg gatgggtacc agatcttcat attcatgcag aagacactct   15600
cctgcctttc tatcttgggg aaaaggacga tgtcacttat gcaataaagc ccacttgctg   15660 gccgggggctt gacattattc cttcctgtct ggctctgcac cgtattgaaa ctgagttaat   15720
gggcaaattt gatgaaggta aactgcccac cgatccacac ctgatgctcc gactggccat   15780
tgaaactgtt gctcatgact atgatgtcat agttattgac agcgcgccta acctgggtat   15840
cggcacgatt aatgtcgtat gtgctgctga tgtgctgatt gttcccacgc ctgctgagtt   15900
gtttgactac acctccgcac tgcagttttt cgatatgctt cgtgatctgc tcaagaacgt   15960
tgatcttaaa gggttcgagc ctgatgtacg tattttgctt accaaataca gcaatagtaa   16020
tggctctcag tccccgtgga tggaggagca aattcgggat gcctggggaa gcatggttct   16080
aaaaaatgtt gtacgtgaaa cggatgaagt tggtaaaggt cagatccgga tgagaactgt   16140
ttttgaacag gccattgatc aacgctcttc aactggtgcc tggagaaatg ctctttctat   16200
```

| | | | | | |
|---|---|---|---|---|---|
| ttgggaacct | gtctgcaatg | aaattttcga | tcgtctgatt | aaaccacgct | gggagattag | 16260 |
| ataatgaagc | gtgcgcctgt | tattccaaaa | catacgctca | atactcaacc | ggttgaagat | 16320 |
| acttcgttat | cgacaccagc | tgccccgatg | gtggattcgt | taattgcgcg | cgtaggagta | 16380 |
| atggctcgcg | gtaatgccat | tactttgcct | gtatgtggtc | gggatgtgaa | gtttactctt | 16440 |
| gaagtgctcc | ggggtgatag | tgttgagaag | acctctcggg | tatggtcagg | taatgaacgt | 16500 |
| gaccaggagc | tgcttactga | ggacgcactg | gatgatctca | tcccttcttt | tctactgact | 16560 |
| ggtcaacaga | caccggcgtt | cggtcgaaga | gtatctggtg | tcatagaaat | tgccgatggg | 16620 |
| agtcgccgtc | gtaaagctgc | tgcacttacc | gaaagtgatt | atcgtgttct | ggttggcgag | 16680 |
| ctggatgatg | agcagatggc | tgcattatcc | agattgggta | acgattatcg | cccaacaagt | 16740 |
| gcttatgaac | gtggtcagcg | ttatgcaagc | cgattgcaga | atgaatttgc | tggaaatatt | 16800 |
| tctgcgctgg | ctgatgcgga | aaatatttca | cgtaagatta | ttacccgctg | tatcaacacc | 16860 |
| gccaaattgc | ctaaatcagt | tgttgctctt | ttttctcacc | ccggtgaact | atctgcccgg | 16920 |
| tcaggtgatg | cacttcaaaa | agcctttaca | gataaagagg | aattacttaa | gcagcaggca | 16980 |
| tctaaccttc | atgagcagaa | aaaagctggg | gtgatatttg | aagctgaaga | agttatcact | 17040 |
| cttttaactt | ctgtgcttaa | aacgtcatct | gcatcaagaa | ctagtttaag | ctcacgacat | 17100 |
| cagtttgctc | ctggagcgac | agtattgtat | aagggcgata | aaatggtgct | taacctggac | 17160 |
| aggtctcgtg | ttccaactga | gtgtatagag | aaaattgagg | ccattcttaa | ggaacttgaa | 17220 |
| aagccagcac | cctgatgcga | ccacgtttta | gtctacgttt | atctgtcttt | acttaatgtc | 17280 |
| ctttgttaca | ggccagaaag | cataactggc | ctgaatattc | tctctgggcc | cactgttcca | 17340 |
| cttgtatcgt | cggtctgata | atcagactgg | gaccacggtc | ccactcgtat | cgtcggtctg | 17400 |
| attattagtc | tgggaccacg | gtcccactcg | tatcgtcggt | ctgattatta | gtctgggacc | 17460 |
| acggtcccac | tcgtatcgtc | ggtctgataa | tcagactggg | accacggtcc | cactcgtatc | 17520 |
| gtcggtctga | ttattagtct | gggaccatgg | tcccactcgt | atcgtcggtc | tgattattag | 17580 |
| tctgggacca | cggtcccact | cgtatcgtcg | gtctgattat | tagtctggaa | ccacggtccc | 17640 |
| actcgtatcg | tcggtctgat | tattagtctg | gaccacggt | cccactcgta | tcgtcggtct | 17700 |
| gattattagt | ctgggaccac | gatcccactc | gtgttgtcgg | tctgattatc | ggtctgggac | 17760 |
| cacggtccca | cttgtattgt | cgatcagact | atcagcgtga | gactacgatt | ccatcaatgc | 17820 |
| ctgtcaaggg | caagtattga | catgtcgtcg | taacctgtag | aacggagtaa | cctcggtgtg | 17880 |
| cggttgtatg | cctgctgtgg | attgctgctg | tgtcctgctt | atccacaaca | ttttgcgcac | 17940 |
| ggttatgtgg | acaaaatacc | tggttaccca | ggccgtgccg | gcacgttaac | tgtgtcagtt | 18000 |
| agggtgtgga | aagtccccag | gctccccagc | aggcagaagt | atgcaaagca | tgcatctcaa | 18060 |
| ttagtcagca | accaggtgtg | gaaagtcccc | aggctcccca | gcaggcagaa | gtatgcaaag | 18120 |
| catgcatctc | aattagtcag | caaccatagt | cccgccccta | actccgccca | tcccgcccct | 18180 |
| aactccgccc | agttccgccc | attctccgcc | ccatggctga | ctaattttttt | ttatttatgc | 18240 |
| agaggccgag | gccgcctc | | | | | 18258 |

<210> SEQ ID NO 8
<211> LENGTH: 10
<212> TYPE: DNA
<213> ORGANISM: Artificial Sequence
<220> FEATURE:
<223> OTHER INFORMATION: 3' UTR Zika 10 Nucleotide Deletion

<400> SEQUENCE: 8

```
ccagaagagg                                                        10

<210> SEQ ID NO 9
<211> LENGTH: 20
<212> TYPE: DNA
<213> ORGANISM: Artificial Sequence
<220> FEATURE:
<223> OTHER INFORMATION: 3' UTR Zika 20 Nucleotide Deletion

<400> SEQUENCE: 9
ctgtggatct ccagaagagg                                             20

<210> SEQ ID NO 10
<211> LENGTH: 17
<212> TYPE: DNA
<213> ORGANISM: Artificial Sequence
<220> FEATURE:
<223> OTHER INFORMATION: forward primer - 1193F

<400> SEQUENCE: 10
ccgctgccca acacaag                                                17

<210> SEQ ID NO 11
<211> LENGTH: 24
<212> TYPE: DNA
<213> ORGANISM: Artificial Sequence
<220> FEATURE:
<223> OTHER INFORMATION: reverse primer - 1269R

<400> SEQUENCE: 11
ccactaacgt tcttttgcag acat                                        24

<210> SEQ ID NO 12
<211> LENGTH: 31
<212> TYPE: DNA
<213> ORGANISM: Artificial Sequence
<220> FEATURE:
<223> OTHER INFORMATION: probe
<220> FEATURE:
<221> NAME/KEY: MOD_RES
<222> LOCATION: (1)..(1)
<223> OTHER INFORMATION: linked to FAM
<220> FEATURE:
<221> NAME/KEY: MOD_RES
<222> LOCATION: (10)..(10)
<223> OTHER INFORMATION: linked to Zen

<400> SEQUENCE: 12
agcctacctt gacaagcaat cagacactca a                                31

<210> SEQ ID NO 13
<211> LENGTH: 28
<212> TYPE: DNA
<213> ORGANISM: Artificial Sequence
<220> FEATURE:
<223> OTHER INFORMATION: forward primer - 1183F

<400> SEQUENCE: 13
ccaccaatgt tctcttgcag acatattg                                    28

<210> SEQ ID NO 14
<211> LENGTH: 26
<212> TYPE: DNA
<213> ORGANISM: Artificial Sequence
<220> FEATURE:
<223> OTHER INFORMATION: reverse primer - 1268R
```

```
<400> SEQUENCE: 14
ttcggacagc cgttgtccaa cacaag                                              26

<210> SEQ ID NO 15
<211> LENGTH: 21
<212> TYPE: DNA
<213> ORGANISM: Artificial Sequence
<220> FEATURE:
<223> OTHER INFORMATION: probe
<220> FEATURE:
<221> NAME/KEY: MOD_RES
<222> LOCATION: (1)..(1)
<223> OTHER INFORMATION: linked to FAM
<220> FEATURE:
<221> NAME/KEY: MOD_RES
<222> LOCATION: (10)..(10)
<223> OTHER INFORMATION: linked to Zen

<400> SEQUENCE: 15
agcctacctt gacaagcagt c                                                   21

<210> SEQ ID NO 16
<211> LENGTH: 17
<212> TYPE: DNA
<213> ORGANISM: Artificial Sequence
<220> FEATURE:
<223> OTHER INFORMATION: forward primer - 1193F

<400> SEQUENCE: 16
ccgctgccca acacaag                                                        17

<210> SEQ ID NO 17
<211> LENGTH: 24
<212> TYPE: DNA
<213> ORGANISM: Artificial Sequence
<220> FEATURE:
<223> OTHER INFORMATION: reverse primer - 1269R

<400> SEQUENCE: 17
ccactaacgt tcttttgcag acat                                                24

<210> SEQ ID NO 18
<211> LENGTH: 31
<212> TYPE: DNA
<213> ORGANISM: Artificial Sequence
<220> FEATURE:
<223> OTHER INFORMATION: probe
<220> FEATURE:
<221> NAME/KEY: MOD_RES
<222> LOCATION: (1)..(1)
<223> OTHER INFORMATION: linked to FAM
<220> FEATURE:
<221> NAME/KEY: MOD_RES
<222> LOCATION: (10)..(10)
<223> OTHER INFORMATION: linked to Zen

<400> SEQUENCE: 18
agcctacctt gacaagcaat cagacactca a                                        31

<210> SEQ ID NO 19
<211> LENGTH: 22
<212> TYPE: DNA
<213> ORGANISM: Artificial Sequence
<220> FEATURE:
<223> OTHER INFORMATION: probe - 3IABkFQ-3'

<400> SEQUENCE: 19
tgacaagcaa tcagacactc aa                                                  22
```

<210> SEQ ID NO 20
<211> LENGTH: 45
<212> TYPE: DNA
<213> ORGANISM: Artificial Sequence
<220> FEATURE:
<223> OTHER INFORMATION: WT

<400> SEQUENCE: 20
tggagatcag ctgtggatct ccagaagagg gactagtggt tagag          45

<210> SEQ ID NO 21
<211> LENGTH: 34
<212> TYPE: DNA
<213> ORGANISM: Artificial Sequence
<220> FEATURE:
<223> OTHER INFORMATION: 10-del

<400> SEQUENCE: 21
tggagatcag ctgtggatcg actagtggtt agag          34

<210> SEQ ID NO 22
<211> LENGTH: 25
<212> TYPE: DNA
<213> ORGANISM: Artificial Sequence
<220> FEATURE:
<223> OTHER INFORMATION: 20-del

<400> SEQUENCE: 22
tggagatcag gactagtggt tagag          25

<210> SEQ ID NO 23
<211> LENGTH: 15
<212> TYPE: DNA
<213> ORGANISM: Artificial Sequence
<220> FEATURE:
<223> OTHER INFORMATION: 30-del-a

<400> SEQUENCE: 23
gactagtggt tagag          15

<210> SEQ ID NO 24
<211> LENGTH: 15
<212> TYPE: DNA
<213> ORGANISM: Artificial Sequence
<220> FEATURE:
<223> OTHER INFORMATION: 30-del-b

<400> SEQUENCE: 24
tggagatcag ctgtg          15

<210> SEQ ID NO 25
<211> LENGTH: 45
<212> TYPE: DNA
<213> ORGANISM: Artificial Sequence
<220> FEATURE:
<223> OTHER INFORMATION: FSS13025/KU955593

<400> SEQUENCE: 25
tggagatcag ctgtggatct ccagaagagg gactagtggt tagag          45

<210> SEQ ID NO 26
<211> LENGTH: 45
<212> TYPE: DNA
<213> ORGANISM: Artificial Sequence
<220> FEATURE:

```
<223> OTHER INFORMATION: H/PF2013/KJ776791

<400> SEQUENCE: 26
tggagatcag ctgtggatct ccagaagagg gactagtggt tagag          45

<210> SEQ ID NO 27
<211> LENGTH: 45
<212> TYPE: DNA
<213> ORGANISM: Artificial Sequence
<220> FEATURE:
<223> OTHER INFORMATION: PRVABC 59/KU501215

<400> SEQUENCE: 27
tggagatcag ctgtggatct ccagaagagg gactagtggt tagag          45

<210> SEQ ID NO 28
<211> LENGTH: 45
<212> TYPE: DNA
<213> ORGANISM: Artificial Sequence
<220> FEATURE:
<223> OTHER INFORMATION: Natal RGN/KU527068

<400> SEQUENCE: 28
tggagatcag ctgtggatct ccagaagagg gactagtggt tagag          45

<210> SEQ ID NO 29
<211> LENGTH: 45
<212> TYPE: DNA
<213> ORGANISM: Artificial Sequence
<220> FEATURE:
<223> OTHER INFORMATION: ZKV2015/KU497555

<400> SEQUENCE: 29
tggagatcag ctgtggatct ccagaagagg gactagtggt tagag          45

<210> SEQ ID NO 30
<211> LENGTH: 45
<212> TYPE: DNA
<213> ORGANISM: Artificial Sequence
<220> FEATURE:
<223> OTHER INFORMATION: P6-740/KX377336

<400> SEQUENCE: 30
tggagatcag ctgtggatct ccaggagagg gactagcggt tagag          45

<210> SEQ ID NO 31
<211> LENGTH: 45
<212> TYPE: DNA
<213> ORGANISM: Artificial Sequence
<220> FEATURE:
<223> OTHER INFORMATION: MR 766/ AY632535

<400> SEQUENCE: 31
tggagactag ctgtgaatct ccagcagagg gactagtggt tagag          45

<210> SEQ ID NO 32
<211> LENGTH: 45
<212> TYPE: DNA
<213> ORGANISM: Artificial Sequence
<220> FEATURE:
<223> OTHER INFORMATION: DAK-41525/KU955591

<400> SEQUENCE: 32
tggagattag ctgtgaatct ccggcagaag gactagtggt tagag          45
```

LIVE ATTENUATED ZIKA VIRUS WITH 3'UTR DELETION, VACCINE CONTAINING AND USE THEREOF

RELATED APPLICATIONS

This application is a U.S. National Phase application of International Application No. PCT/US2018/018114, filed Feb. 14, 2018, which claims priority to U.S. Provisional Application No. 62/458,839, filed Feb. 14, 2017, each of which is incorporated herein by reference.

STATEMENT REGARDING FEDERALLY SPONSORED RESEARCH OR DEVELOPMENT

The invention was funded by NIH grant AI120942.

SEQUENCE LISTING DISCLOSURE

Sequence Listing

This application includes as part of its disclosure a biological sequence listing which is being concurrently submitted through EFS-Web. Said biological sequence listing is contained in a file named "1149561o001207" which was created Oct. 28, 2019, and has a size of 57,144 bytes, and is hereby incorporated by reference in its entirety.

FIELD OF THE INVENTION

The invention generally relates to the development of a live attenuated strain of Zika virus (ZIKV) and vaccine compositions comprising this strain. The strain and vaccines comprising it may be used in humans and animals for treating or providing immunoprotection against ZIKV, which may cause congenital ZIKV syndrome and Guillan-Barre syndrome. The invention specifically discloses methods of protecting against congenital ZIKV syndrome, including microcephaly.

BACKGROUND OF THE INVENTION

The mosquito-borne ZIKV has recently caused a global threat to public health. The most devastating disease associated with Zika virus (ZIKV) infection is the wide range of congenital abnormalities (including microcephaly) now collectively known as congenital ZIKV syndrome (Reference 1). Prevention of congenital ZIKV syndrome is the most pressing task to reduce the burden of epidemics on family and society (Reference 2). In particular, pregnant women without ZIKV immunity in endemic countries are at risk for fetal infection and congenital defects. Since ZIKV could also be sexually transmitted, women living in non-endemic regions can also be at risk when exposed to men who have traveled to endemic countries.

ZIKV is spread to people primarily through the bite of an infected *Aedes* species mosquito. The most common symptoms of ZIKV are fever, rash, joint pain, and conjunctivitis. The illness is usually mild, with symptoms appearing 2 to 7 days after being bitten by an infected mosquito and lasting for several days to a week. However, there have been reports of congenital ZIKV syndrome, e.g., serious birth defects, especially microcephaly, and other poor pregnancy outcomes in babies of mothers who were infected with ZIKV while pregnant. There have also been cases of Guillain-Barre syndrome (GBS) reported in patients following suspected ZIKV infection. GBS is a rare disorder where a person's own immune system damages the nerve cells, causing muscle weakness and sometimes, paralysis. These symptoms can last anywhere from a few weeks to several months, although some people have permanent damage and, in rare cases, GBS may result in death.

ZIKV is a member of the *Flavivirus* genus (in the family Flaviviridae), which also includes other important human pathogens, e.g., yellow fever (YFV), West Nile (WNV), Japanese encephalitis (JEV), tick-borne encephalitis (TBEV), and Dengue viruses (DENV). Like other members of the *Flavivirus* genus, Zika contains a positive single-stranded genomic RNA, encoding a polyprotein that is processed into three structural proteins (capsid [C], premembrane [prM], and envelope [E] proteins) and seven nonstructural proteins (NS1, NS2A, NS2B, NS3, NS4A, NS4B, and NS5). Structural proteins form virions, whereas nonstructural proteins participate in viral RNA synthesis, virion assembly, and evasion of immune response.

Both inactivated and live-attenuated vaccines have been developed for flaviviruses, including YFV, JEV, TBEV, and DENV (Reference 3). Rapid and promising progress has been made toward ZIKV vaccine development (References 4 and 5). Inactivated ZIKV and subunit vaccines (expressing viral prM/E proteins) have shown efficacy in mice and nonhuman primates (References 6-8). A successful vaccine requires a fine balance between immunogenicity and safety. Live-attenuated vaccines generally offer fast and durable immunity, but sometimes with the trade-off of reduced safety; whereas inactivated and subunit vaccines provide enhanced safety at the cost of reduced immunogenicity, and often require multiple doses and periodic boosters.

The present invention addresses the need for novel ZIKV vaccines that serve at-risk populations in order to treat and/or provide immunoprotection against infections elicited by ZIKV and to prevent congenital ZIKV syndrome, especially microcephaly.

BRIEF SUMMARY OF THE INVENTION

The invention in general relates to a live attenuated Zika virus (ZIKV) strain, comprising a deletion in the 3' untranslated region (3'UTR) of the ZIKV genome.

The invention more specifically relates to a live attenuated Zika virus (ZIKV) strain, wherein the 3'UTR deletion ranges from a 10-nucleotide deletion to a 50-nucleotide deletion (i.e., $\Delta$10, $\Delta$11, $\Delta$12, $\Delta$13, $\Delta$14, $\Delta$15, $\Delta$16, $\Delta$17, $\Delta$18, $\Delta$19, $\Delta$20, $\Delta$21, $\Delta$22, $\Delta$23, $\Delta$24, $\Delta$25, $\Delta$26, $\Delta$27, $\Delta$28, $\Delta$29, $\Delta$30, $\Delta$31, $\Delta$32, $\Delta$33, $\Delta$34, $\Delta$35, $\Delta$36, $\Delta$37, $\Delta$38, $\Delta$39, $\Delta$40, $\Delta$41, $\Delta$42, $\Delta$43, $\Delta$44, $\Delta$45, $\Delta$46, $\Delta$47, $\Delta$48, $\Delta$49 or $\Delta$50 3'UTR deletion), in exemplary embodiments the 3'UTR deletion is a 10-nucleotide deletion, a 20-nucleotide deletion, or a 30-nucleotide deletion.

The invention more specifically relates to a live attenuated Zika virus (ZIKV) strain comprising a 3'UTR having at least 80%, at least 85%, at least 90%, at least 95%, at least 98%, at least 99%, or 100% identity to the nucleic acid sequence of SEQ ID NO: 2, 3, 4, or 5.

The invention also specifically relates to a live attenuated Zika virus (ZIKV) strain as above-described which is incompetent in infecting mosquitoes.

The invention also specifically relates to a live attenuated Zika virus (ZIKV) strain as above-described which exhibits decreased viral RNA synthesis compared to wildtype ZIKV strains.

The invention also specifically relates to a live attenuated Zika virus (ZIKV) strain as above-described which exhibits increased sensitivity to type-I interferon inhibition compared to wildtype ZIKV strains.

The invention also specifically relates to a live attenuated Zika virus (ZIKV) strain as above-described wherein the deletion does not affect viral RNA translation.

The invention also specifically relates to a live attenuated Zika virus (ZIKV) strain as above-described which is an mCherry ZIKV strain.

The invention also specifically relates to a live attenuated Zika virus (ZIKV) strain as above-described which comprises or consists of a deletion variant of SEQ ID NO:6 wherein the sequence "CCAGAAGAGG" (3'UTR 10-nucleotide deletion) (SEQ ID NO:8) is deleted therefrom.

The invention also specifically relates to a live attenuated Zika virus (ZIKV) strain as above-described which comprises or consists of a deletion variant of SEQ ID NO:6 wherein the sequence "CTGTGGATCTCCAGAAGAGG" (3'UTR 20-nucleotide deletion) (SEQ ID NO:9) is deleted therefrom.

The invention also specifically relates to a live attenuated Zika virus (ZIKV) strain as above-described which comprises or consists of a deletion variant of SEQ ID NO:7 wherein the sequence "CCAGAAGAGG" (3'UTR 10-nucleotide deletion) (SEQ ID NO:8) is deleted therefrom.

The invention also specifically relates to a live attenuated Zika virus (ZIKV) strain as above-described which comprises or consists of a deletion variant of SEQ ID NO:7 wherein the sequence "CTGTGGATCTCCAGAAGAGG" (3'UTR 20-nucleotide deletion) (SEQ ID NO:9) is deleted therefrom.

The invention also specifically relates to an immunogenic composition comprising a live attenuated ZIKV strain as above-described, which further comprises at least one pharmaceutically acceptable carrier or excipient.

The invention also specifically relates to an immunogenic composition comprising a live attenuated ZIKV strain as above-described, which is suitable for parenteral or enteral administration.

The invention also specifically relates to a method of eliciting an immune response in a subject in need thereof comprising administering a prophylactically or therapeutically effective amount of a live attenuated ZIKV strain or immunogenic composition as above-described.

The invention also specifically relates to a method of eliciting an immune response in a subject in need thereof comprising administering a prophylactically or therapeutically effective amount of a live attenuated ZIKV strain or immunogenic composition as above-described, which induces a CD8$^+$ T cell response, an antibody response, and/or a cellular immune response against ZIKV.

The invention also specifically relates to a method of eliciting an immune response in a subject in need thereof comprising administering a prophylactically or therapeutically effective amount of a live attenuated ZIKV strain or immunogenic composition as above-described, which produces a neutralizing antibody titer equivalent to that of wildtype ZIKV infection.

The invention also specifically relates to a method of eliciting an immune response in a subject in need thereof comprising administering a prophylactically or therapeutically effective amount of a live attenuated ZIKV strain or immunogenic composition as above-described, wherein the subject is a pregnant female.

The invention also specifically relates to a method of eliciting an immune response in a subject in need thereof comprising administering a prophylactically or therapeutically effective amount of a live attenuated ZIKV strain or immunogenic composition as above-described, in order to prevent congenital ZIKV syndrome.

The invention also specifically relates to a method of eliciting an immune response in a subject in need thereof comprising administering a prophylactically or therapeutically effective amount of a live attenuated ZIKV strain or immunogenic composition as above-described, in order to prevent microcephaly.

The invention also specifically relates to a method of eliciting an immune response in a subject in need thereof comprising administering a prophylactically or therapeutically effective amount of a live attenuated ZIKV strain or immunogenic composition as above-described, wherein at least $1.0 \times 10^1$, $1.0 \times 10^2$, $1.0 \times 10^3$, $1.0 \times 10^4$, $1.0 \times 10^5$, or $1.0 \times 10^6$ IFUs of the live attenuated ZIKV strain is administered to the subject.

The invention also specifically relates to a method of eliciting an immune response in a subject in need thereof comprising administering a prophylactically or therapeutically effective amount of a live attenuated ZIKV strain or immunogenic composition as above-described, wherein the administration of said composition prevents viremia in said subject after subsequent challenge with a wildtype ZIKV strain.

The invention also specifically relates to a method of eliciting an immune response in a subject in need thereof comprising administering a prophylactically or therapeutically effective amount of a live attenuated ZIKV strain or immunogenic composition as above-described, wherein the subject is a human.

BRIEF DESCRIPTION OF THE SEVERAL VIEWS OF THE DRAWINGS

FIG. 1A-1F contain characterizations of the 3'UTR deletion mutants in cell culture. FIG. 1A provides sequences of the ZIKV 3'UTR deletions WT (SEQ ID NO:20), 10-del (SEQ ID NO:21), 20-del (SEQ ID NO:22), 30-del-a (SEQ ID NO:23), and 30-del-b (SEQ ID NO:24). FIG. 1B shows an immunostaining focus assay of mutant viruses. Equal amounts of RNAs (10 µg) transcribed from their corresponding infectious cDNA clones were electroporated into Vero cells. On day 4 or 5 post-transfection, culture fluids from the transfected cells were harvested and quantified for infectious viruses (defined as P0 virus) using an immunostaining focus assay on Vero cells. FIG. 1C demonstrates the replication kinetics of WT and mutant viruses. Vero cells in 24-well plates ($2 \times 10^5$ cells per well) were infected with WT and mutant viruses at an MOI of 0.01. Culture fluids were quantified for infectious viruses on days 1 to 5 using the immunostaining focus assay. From left to right for each day, the bars correspond to: WT, 10-del, 20-del, 30-del-a, and 30-del-b. FIG. 1D illustrates a *Renilla* luciferase reporter replicon construct. FIG. 1E contains a replicon analysis of the 3'UTR deletions. A *Renilla* luciferase reporter replicon of ZIKV (FIG. 1D) was engineered with various 3'UTR deletions. Equal amounts of replicon WT and mutant RNAs (10 µg) were electroporated into Vero cells. Luciferase signals were measured at the indicated time points. A non-replicative replicon containing an NS5 polymerase-inactive GDD mutation was included as a negative control. The averages of three replicates are presented. Error bars represent standard deviations. RLU, relative light units. The top curve corresponds to WT and the bottom curve corresponds to the GDD control. FIG. 1F shows the interferon-β inhibition of WT and mutant ZIKVs. Vero cells were seeded in 96-well plate ($1.5 \times 10^4$ cell per well) one day before interferon treatment and viral infection. The cells were infected at an MOI 0.05 in the presence of IFN-β (55, 167, 500, or 1,500 IU/ml). Viral infection and interferon treatment were initiated at the same time. At 48 h post-infection and interferon-β treatment, viral titers were quantified using the immunostaining focus assay on Vero cells. Percentages of viral titer inhibition are presented in $\log_{10}$ scale. Viral titers without interferon-β treatment are set as 100%. Average results of three independent experiments are shown. Error bars represent standard deviations. Symbols  and * indicate P values <0.01 and <0.001, respectively. From left to right for each day, the bars correspond to: WT, 10-del, 20-del, 30-del-a, and 30-del-b.

Figure 2A:
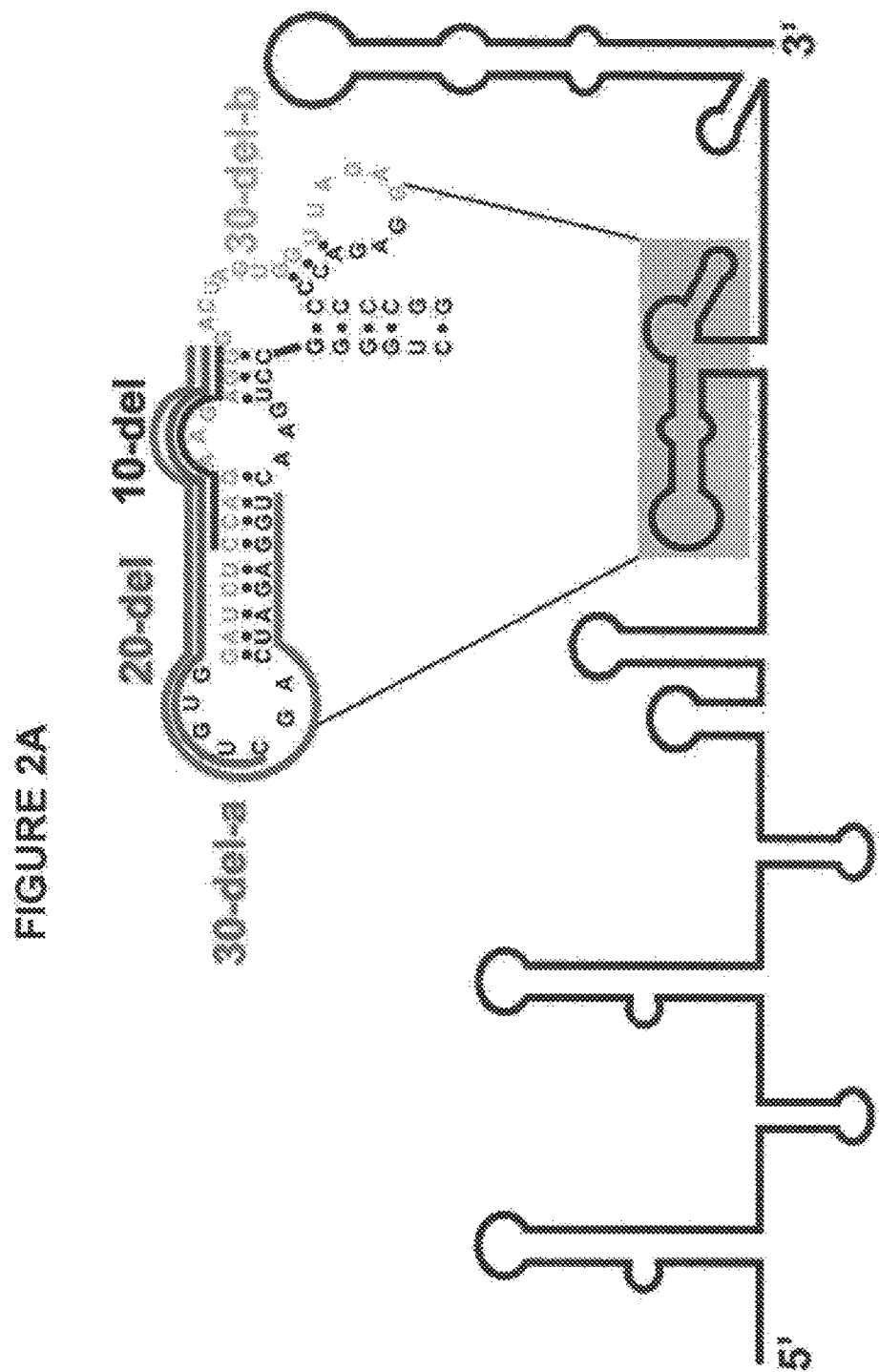

FIG. 2A-2B shows the sequence information of the 3'UTR and the deletion mutants. FIG. 2A depicts the predicted RNA secondary structure of the ZIKV 3'UTR. The stem-loop structure of the 3'UTR of the ZIKV genome is presented as previously reported (References 33,34). The nucleotide sequence of the shaded stem-loop is shown (representing nucleotides 238 to 307 of SEQ ID NO:1). The deleted sequences for 10-del, 20-del, 30-del-a, and 30-del-b mutants are displayed in blue, magenta, green, and orange, respectively. FIG. 2B shows a sequence alignment of the deleted region (nucleotide position 10,630-10,674) in the 3'UTR. The 10-del nucleotides are indicated. Within the 10-del region, sequence variations are observed for early isolates (P6-740 (SEQ ID NO:30), MR766 (SEQ ID NO:31), and DAK-41525 (SEQ ID NO:32) were isolated in 1966, 1947, and 1984, respectively), while an identical sequence is observed for the strains isolated after 2010 (FSS13025 (SEQ ID NO:25), H/PF2013 (SEQ ID NO:26), PRVABC 59 (SEQ ID NO:27), Natal RGN (SEQ ID NO:28), and ZKV2015 (SEQ ID NO:29)).

FIG. 3 shows an immunofluorescence assay (IFA) of viral protein expression in cells transfected with WT or 3'UTR deletion ZIKV RNA. Vero cells were electroporated with 10 µg of genomic WT or 3'UTR deletion RNA of ZIKV. On day 2 and 3 post-transfection, IFA was performed to examine viral E protein expression using a mouse mAb (4G2) and Alexa Fluor® 488 goat anti-mouse IgG as the primary and secondary antibodies, respectively. Green and blue represent E protein and nuclei (stained with DAPI), respectively. Viral E protein staining is visible for WT and all mutant groups on both days.

FIG. 4A-4C contain a stability analysis of the 3'UTR deletion ZIKVs in cell culture. P0 viruses (derived from the culture fluids of RNA-transfected cells from FIG. 1) were continuously cultured on Vero cells for five rounds (5 days for each round of culture), resulting in P5 viruses. The P5 viruses were then characterized. FIG. 4A shows the results of an immunostaining focus assay. WT and P5 mutant viruses were analyzed using an immunostaining focus assay on Vero cells. For each mutant virus, three independent selections were performed on Vero cells. Representative images of infectious foci for each P5 mutant virus are presented. FIG. 4B shows replication kinetics. Vero cells in 24-well plates ($2 \times 10^5$ cells per well) were infected with WT and P5 mutant viruses at an MOI of 0.01. Culture fluids were quantified for infectious viruses on days 1 to 5 using the immunostaining focus assay on Vero cells. From left to right for each day, the bars correspond to: WT, 10-del, 20-del, 30-del-a, and 30-del-b. FIG. 4C shows adaptive mutations in P5 mutant viruses. The complete genomes of P5 mutant viruses were sequenced for each of the three independent selections. The adaptive mutations are indicated by their amino acid positions of indicated genes based on ZIKV FSS13025 strain (GenBank number KU955593.1).

Figure 6A:
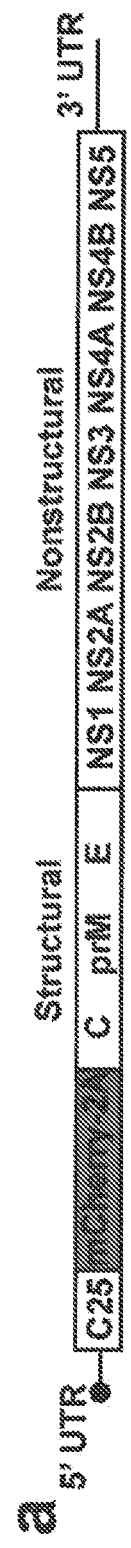
Figure 6B:
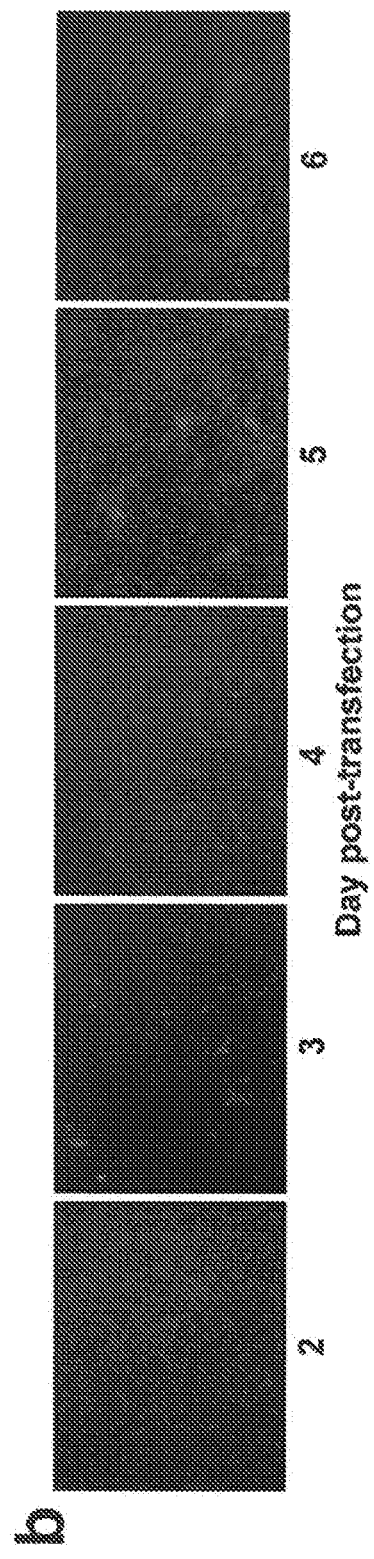

FIG. 5A-5G show a characterization of 3'UTR mutants in the A129 mouse model. FIG. 5A contains an experimental scheme. In two separate experiments, three-week old A129 mice (n=8) were immunized via the S.C. route with $1 \times 10^4$ IFU WT and mutant viruses. The immunized mice were monitored for weight loss, survival, and viremia. FIG. 5B shows the results for weight loss. Weight loss is indicated by percentage using the weight on the day before immunization as 100%. The lowest curve corresponds to WT. FIG. 5C shows the results for survival. The lowest curve corresponds to WT. FIG. 5D shows the results for viremia. Viremias were quantified by an immunostaining focus assay from day 2 to 4 post-infection. From left to right for each day, the bars correspond to: WT, 10-del, 20-del, 30-del-a, and 30-del-b. FIG. 5E shows the pre-challenge neutralization antibody titers. On day 28 post-immunization, mouse sera were measured for neutralizing titers using an mCherry ZIKV infection assay (FIG. 6A-6B). FIG. 5F shows the post-challenge viremia. On day 28 post-immunization, mice were challenged with $1 \times 10^5$ PFU parental virus (ZIKV strain FSS13025) via the I.P. route. Viremia on day 2 post-challenge was quantified using the immunostaining focus assay. FIG. 5G shows the post-challenge neutralization antibody titer. On day 28 post-challenge, mouse sera were quantified for neutralizing titers using the mCherry ZIKV infection assay. L.O.D.: limit of detection.

FIG. 6A-6B show the construction of mCherry ZIKV. FIG. 6A shows a schematic genome of an mCherry ZIKV. A DNA fragment (encoding the first 25 amino acids of C gene, the mCherry gene, and the foot-and-mouth virus 2A protein) was in-frame fused with the open-reading-frame of ZIKV genome. FIG. 6B shows the mCherry expression in Vero cells transfected with mCherry ZIKV RNA. The expression of mCherry in transfected Vero cells was analyzed by fluorescent microscopy at the indicated days post-transfection. The mCherry ZIKV was used to estimate antibody neutralization titers of mouse sera, as described in Methods.

Figures 7A, 7B, 7C:
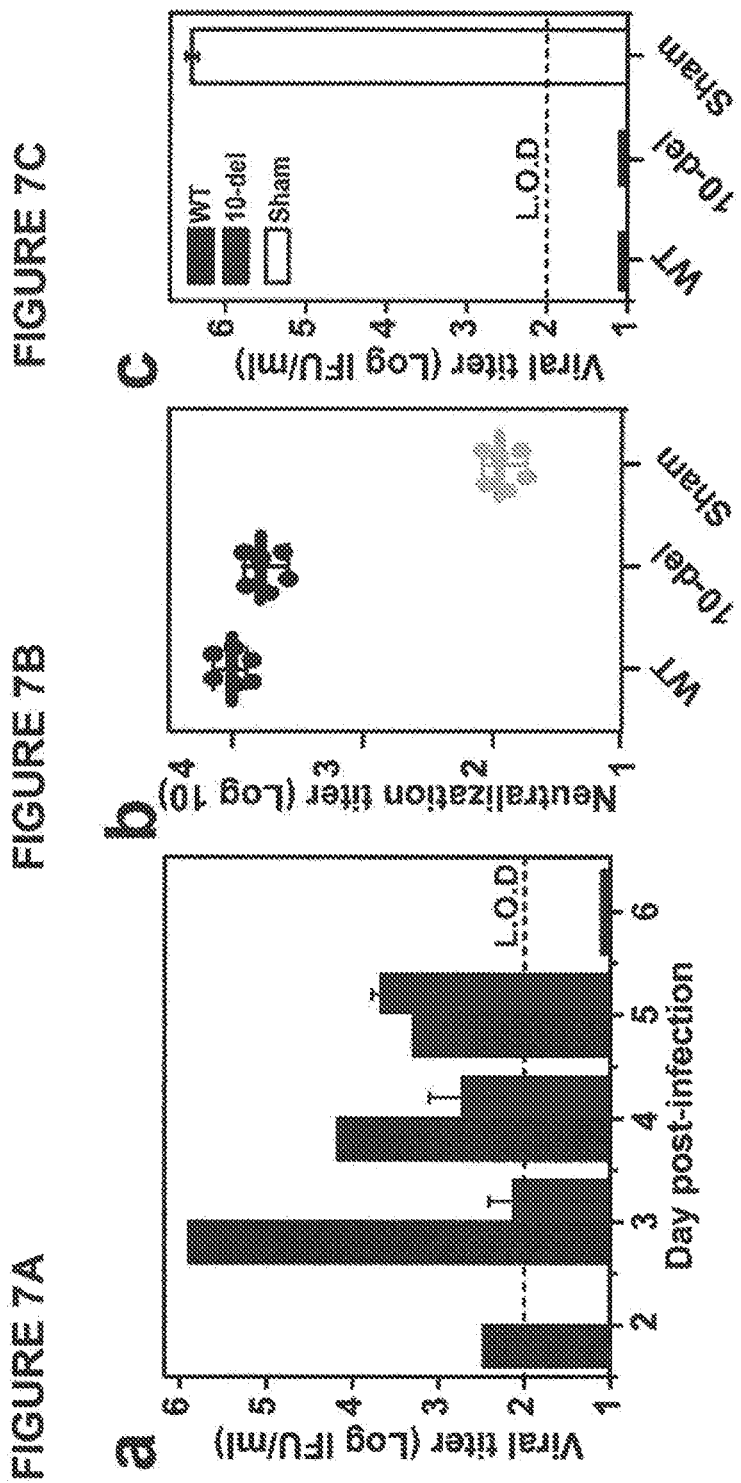

FIG. 7A-7C show the efficacy of immunization with 100 IFU 10-del virus. FIG. 7A shows the viremia after immunization with 100 IFU of WT (left bar) or 10-del ZIKV (right bar). Three-week-old A129 mice (n=5) were immunized with 100 IFU WT or 10-del virus via the S.C. route. Viremia was quantified by immunostaining focus assay from day 2 to 6. L.O.D., limit of detection. FIG. 7B shows the pre-challenge neutralization antibody titers. On day 28 post-immunization, mouse sera were quantified for ZIKV neutralizing antibody titers. FIG. 7C shows the viremia after challenge with ZIKV (Puerto Rico strain PRVABC59). On day 28 post-immunization, the mice were challenged with $1 \times 10^6$ IFU of ZIKV via the I.P. route. Viremias were quantified by immunostaining focus assay on day 2 post-challenge.

Figures 8A, 8B, 8C:
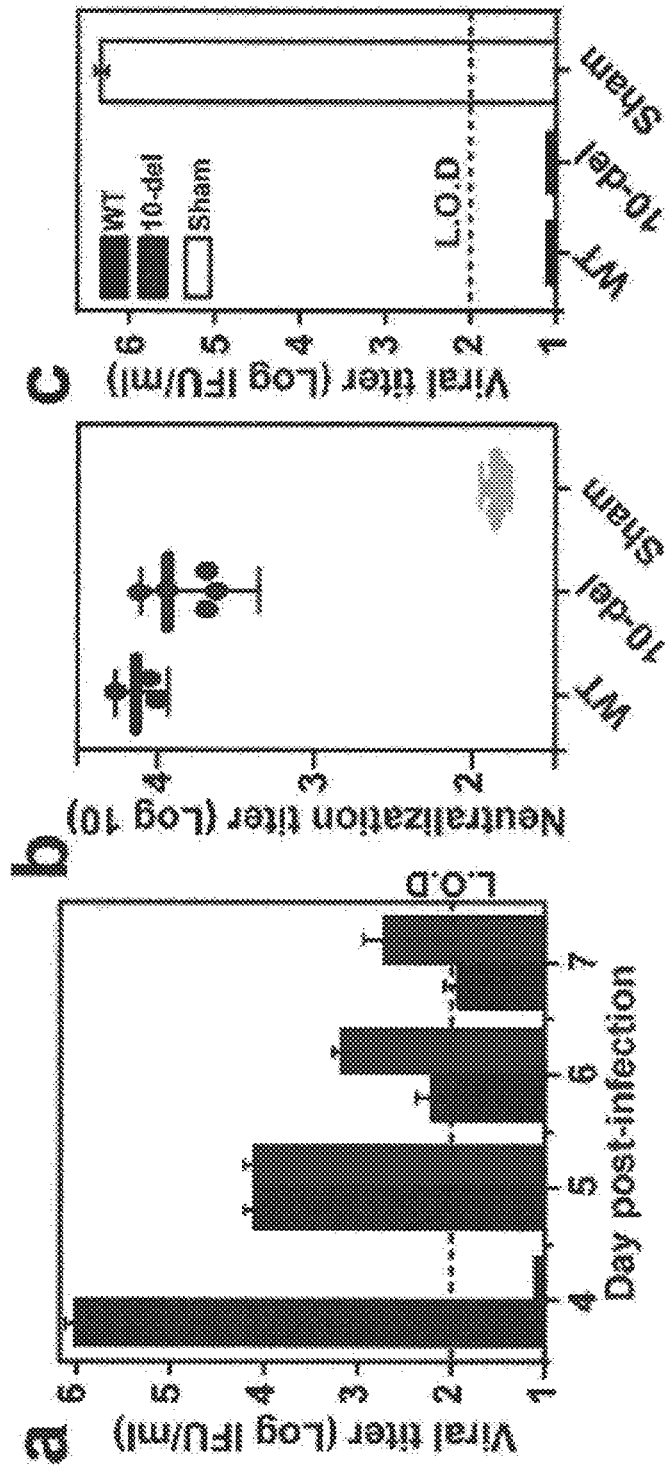

FIG. 8A-8C show the efficacy of immunization with 10 IFU 10-del virus. FIG. 8A shows the viremia after immunization with 10 IFU of WT or 10-del ZIKV. Three-week-old A129 mice (n=5) were immunized with 10 IFU WT or 10-del virus via the S.C. route. Viremia were quantified by immunostaining focus assay from day 4 to 7. L.O.D., limit of detection. FIG. 8B shows the pre-challenge neutralization antibody titers. Three-week-old A129 mice (n=5) were immunized with 10 IFU 10-del ZIKV and PBS via the S.C. route. On day 28 post-immunization, mouse sera were quantified for ZIKV neutralizing antibody titers. On the same day, the mice were challenged with $1 \times 10^6$ IFU of ZIKV (Puerto Rico strain PRVABC59) via the I.P. route.

FIG. 8B shows the viremia after challenge with epidemic ZIKV (Puerto Rico strain PRVABC59). On day 2 post-challenge, viremias were quantified using an immunostaining focus assay. L.O.D.: limit of detection.

Figure 9A:
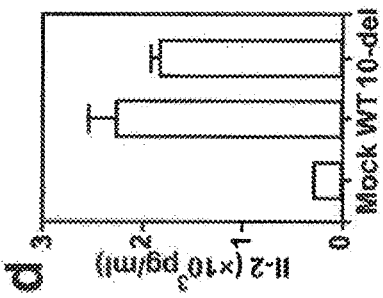
Figure 9B:
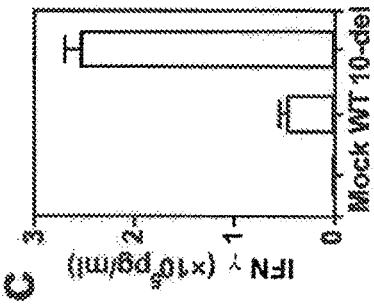
Figure 9C:
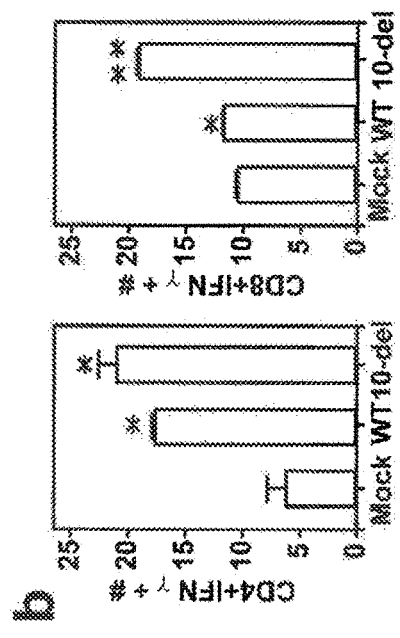
Figure 9D:
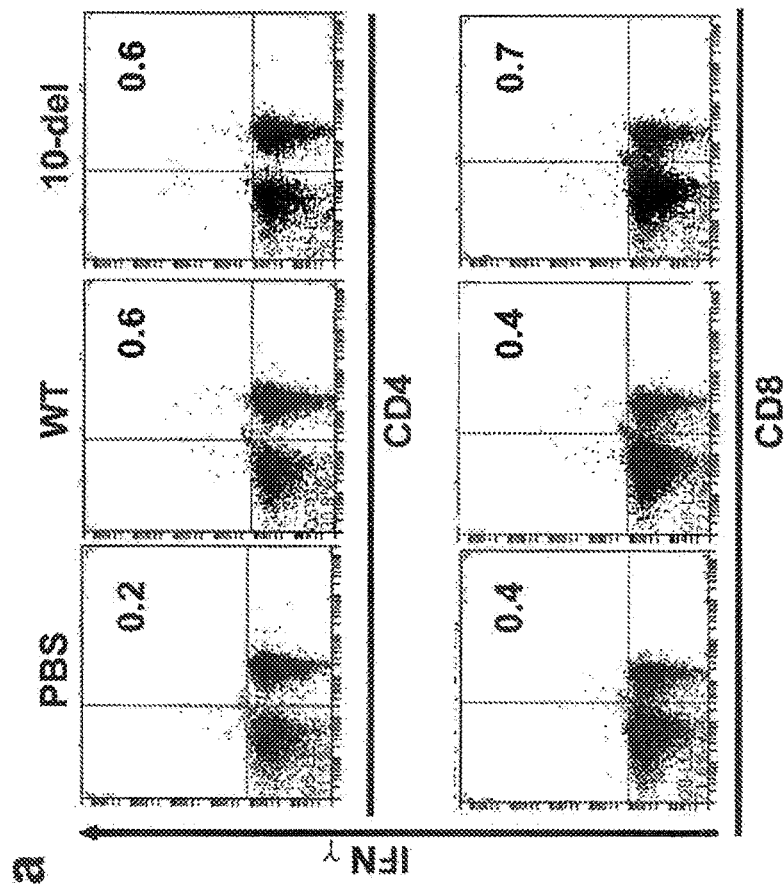

FIG. 9A-9D show the T cell responses after primary infection with ZIKV WT or 10-del mutant. A129 mice were infected with 1×10$^4$ IFU WT and 10-del viruses. On day 28 post-infection, mouse spleens were harvested. Splenocytes were counted, cultured ex vivo with WT ZIKV for 24 h, and stained for markers (IFN-γ, CD3, and CD4 or CD8). The T cells were gated based on staining for these markers. FIG. 9A shows percentages of CD4$^+$IFN-γ$^+$ cells and CD8$^+$IFN-γ$^+$ cells. FIG. 9B shows the average total number of T cell subsets per spleen. Supernatants from the ex vivo culture were harvested on day 2 after WT ZIKV re-stimulation, and measured for IFN-γ and IL-2 production. FIG. 9C shows IFN-γ production. FIG. 9D shows IL-2 production. Data are presented as means±SEM, n=2-4 per group. *P<0.05 or **P<0.01 difference between the virus- and mock-infected mice.

Figure 10A:
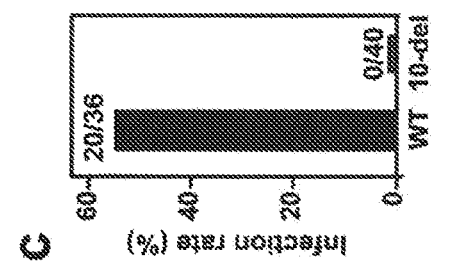
Figure 10B:
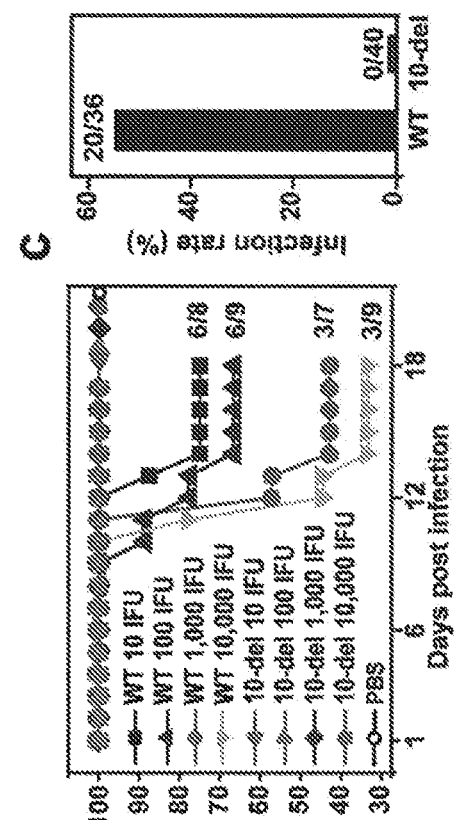
Figure 10C:
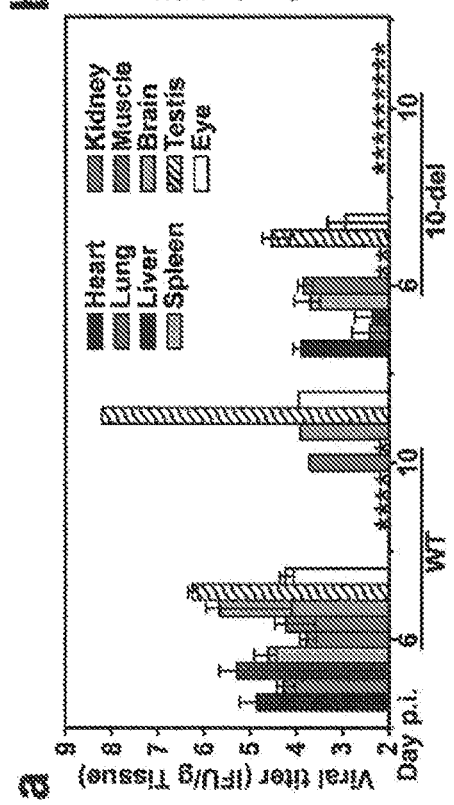

FIG. 10A-10C show the safety evaluation of 10-del virus. FIG. 10A shows the viral loads in organs of infected A129 mice. Three-week-old A129 mice were immunized with 1×10$^4$ IFU of WT and 10-del viruses. Organs from infected mice were collected and homogenized on day 6 and 10 post-infection. The amounts of viruses were quantified on Vero cells using an immunostaining focus assay. The mean results from three animals are presented. Bars denote standard errors. "*" denotes no detectable virus. From left to right on each day, the bars correspond to: heart, lung, liver, spleen, kidney, muscle, brain, testis, and eye. FIG. 10B shows a comparison of neurovirulence of WT and 10-del viruses in CD1 newborn mouse. Groups of one-day-old CD1 mice (n=7-10) were injected via the I.C. route with 10 to 1×10$^4$ IFU of WT or 10-del virus. All 10-del virus curves show 100% survival, while WT curves show less than 100% survival. FIG. 10C shows the results of a mosquito infectivity assay. *Aedes aegypti* were fed with WT or 10-del virus on artificial blood-meals. On day 7 post-feeding, individual engorged, incubated mosquitoes were homogenized and infection was assayed by immunostaining of viral protein expression on inoculated Vero cells (see Methods for details). The number of infected mosquitos and total number of engorged mosquitoes are indicated.

Figure 11C:
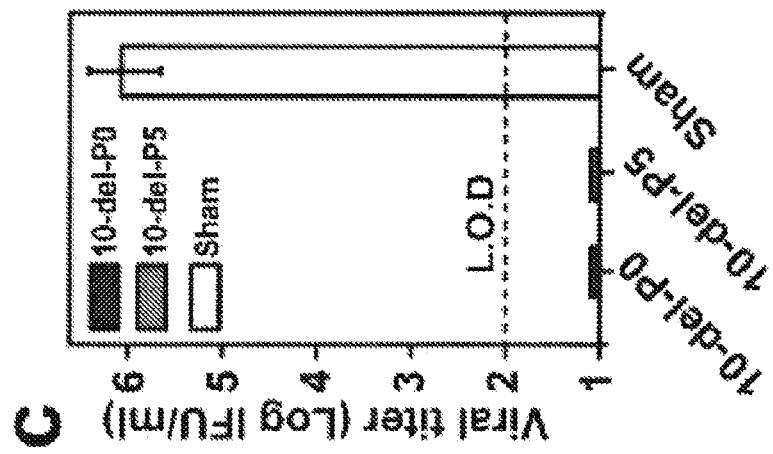
Figure 11B:
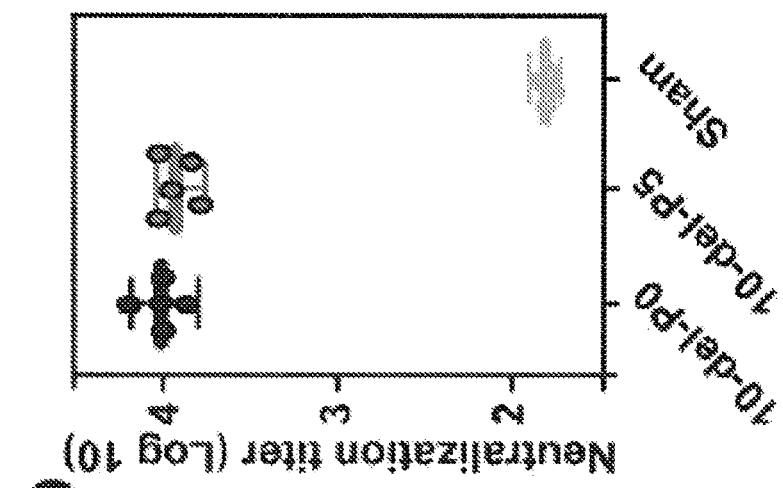
Figure 11A:
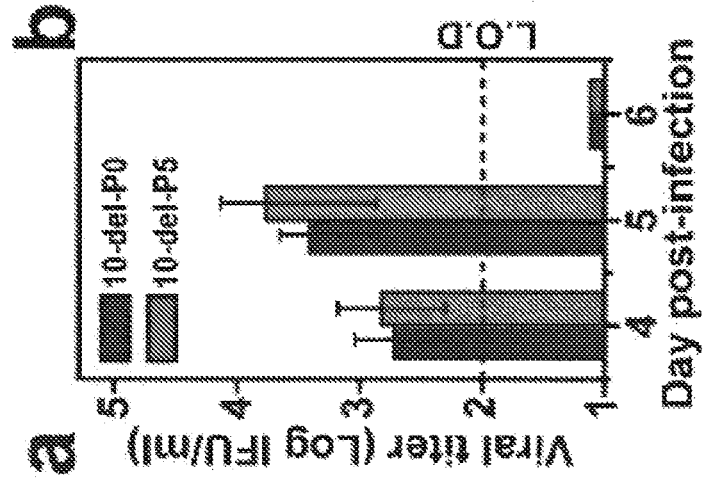

FIG. 11A-11C shows the comparison of viremia and efficacy of P0 and P5 10-del viruses. FIG. 11A shows the viremia after immunization with 100 IFU of P0 or P5 10-del ZIKV. Three-week-old A129 mice (n=5) were immunized with 100 IFU P0 or P5 10-del virus via the S.C. route. Viremia was quantified by immunostaining focus assay from day 4 to 6. L.O.D., limit of detection. FIG. 11B shows pre-challenge neutralization antibody titers. On day 28 post-immunization, mouse sera were quantified for ZIKV neutralizing antibody titers. FIG. 11C shows viremia after challenge with wild-type ZIKV. On day 28 post-immunization, the mice were challenged with 1×10$^6$ IFU of an epidemic strain of ZIKV (Puerto Rico strain PRVABC59) via the I.P. route. On day 2 post-challenge, viremias were quantified using an immunostaining focus assay.

Figure 12A:
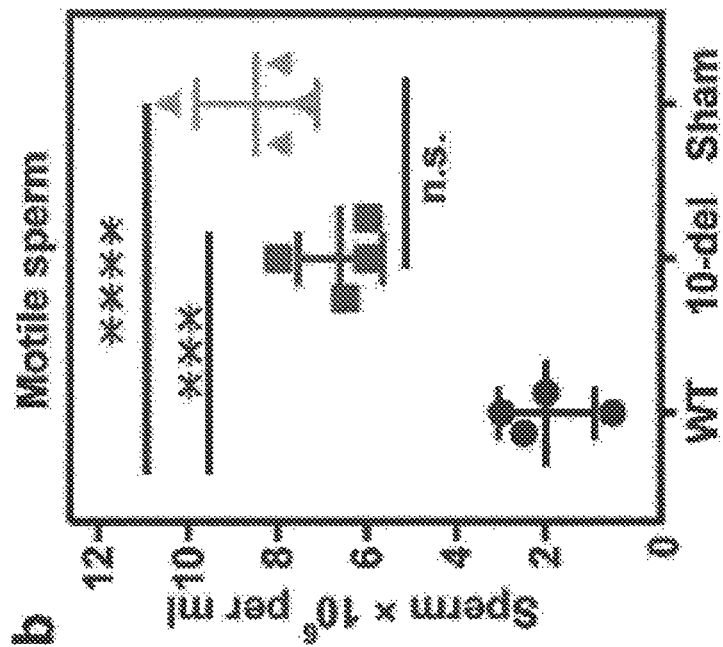
Figure 12B:
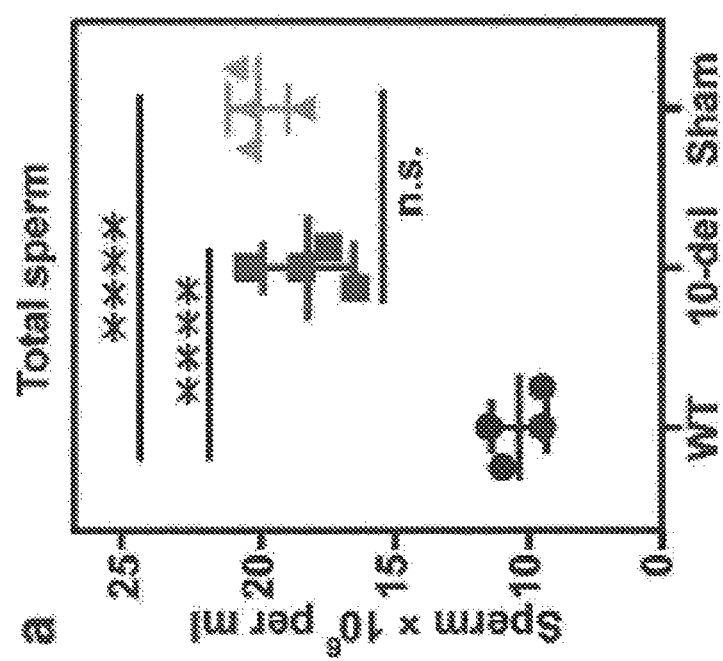

FIG. 12A-12B show a sperm count analysis of A129 mice infected with WT or 10-del mutant virus. Male A129 mice were infected with 1×10$^4$ IFU of WT and 10-del viruses (n=4 per group). On day 16 p.i., epididymis was harvested for sperm count analysis. FIG. 12A shows total sperm counts. FIG. 12B shows motile sperm counts. One-way ANOVA test was performed to indicate statistical significance among different infection groups. n.s., not significant; *very significant (p value<0.001); **extremely significant (p value<0.0001).

FIG. 13A-G shows that ZIKV-3'UTR-Δ10-LAV protects pregnant C57BL/6 mice and their developing fetuses. FIG. 13A shows the scheme of immunization of wild-type (WT) C57BL/6 female mice with 10$^5$ FFU of ZIKV-3'UTR-Δ10-LAV (A10; n=12) or PBS sham (n=16). FIG. 13B shows experiments wherein serum was collected at day 28 post-immunization and analyzed for neutralizing activity using an mCherry infectious ZIKV. Representative neutralization curves are shown. Error bars denote the standard deviation (SD) of duplicate technical replicates. FIG. 13C shows NT$_{50}$ values of neutralizing antibodies were measured for individual animals. The dashed lines indicate the limit of detection (L.O.D.) of the assay. FIG. 13D-G shows that at day 35 post-immunization, vaccinated female mice were mated with WT C57BL/6 males. A subset of the female mice developed vaginal plugs. Pregnant mice (n=8 pooled from two independent experiments) were administered 2 mg of anti-Ifnar1 blocking antibody on E5, and one day later (E6), challenged with 10$^5$ FFU of a pathogenic, mouse adapted ZIKV Dakar 41519 strain. On E13, animals were euthanized; maternal spleen (FIG. 13D), maternal brain (FIG. 13E), placenta (FIG. 13F), and fetal heads (FIG. 13G) were harvested and quantified for viral RNA levels. Median viral RNA levels are indicated for each group. Asterisks indicate significant differences (Mann-Whitney test: ****, P value<0.0001). All negative samples are plotted at the half value of L.O.D. The results in the Figure are pooled from two independent experiments.

FIG. 14A-I show that ZIKV-3'-UTR-Δ10-LAV protects young A129 male mice against testis infection and injury. FIG. 13A contains the scheme of immunization of 3-week-old A129 male mice with 10$^4$ FFU of ZIKV-3'-UTR-Δ10-LAV (A10; n=6) or PBS sham (n=4 or 6). At day 28 post-immunization, mice were measured for neutralization antibody titers. On the same day, mice from one sham group and mice from A10-immunized group were challenged with 10$^6$ FFU of ZIKV-PRVABC59, and viremia was measured at day 2 post-challenge (day 30 post-immunization). At day 49 post-immunization, mice were analyzed for sperm counts and viral load in the testis. FIG. 14A-B shows viremia after immunization with A10 vaccine candidate. FIG. 14C contains NT50 values of antibody neutralization at day 28 post-immunization were measured for individual animals in each group. The dashed lines indicate the limit of detection (L.O.D.) of the assay. FIG. 14D shows viremia at day 2 post-challenge (day 30 post-immunization) with ZIKV PRV-ABC59. FIG. 14E shows viral load in the testis at day 21 post-challenge (day 49 post-immunization). FIG. 14F-G show total (F) and motile (G) sperm counts at day 21 post-challenge. (H-I) Testis weight (H) and representative images of testis (i) from animals from sham, sham with challenge, and Δ10-immunized and challenged groups at day 21 post-challenge. Scale bar, 1 mm. Asterisks indicate significant differences (One-way ANOVA: **, P value<0.0001; *, P value<0.001). Non-significant (n.s.), P value>0.5. All negative samples are plotted at the half value of L.O.D. Error bars represent standard deviations.

Figures 15A, 15B, 15C, 15D:
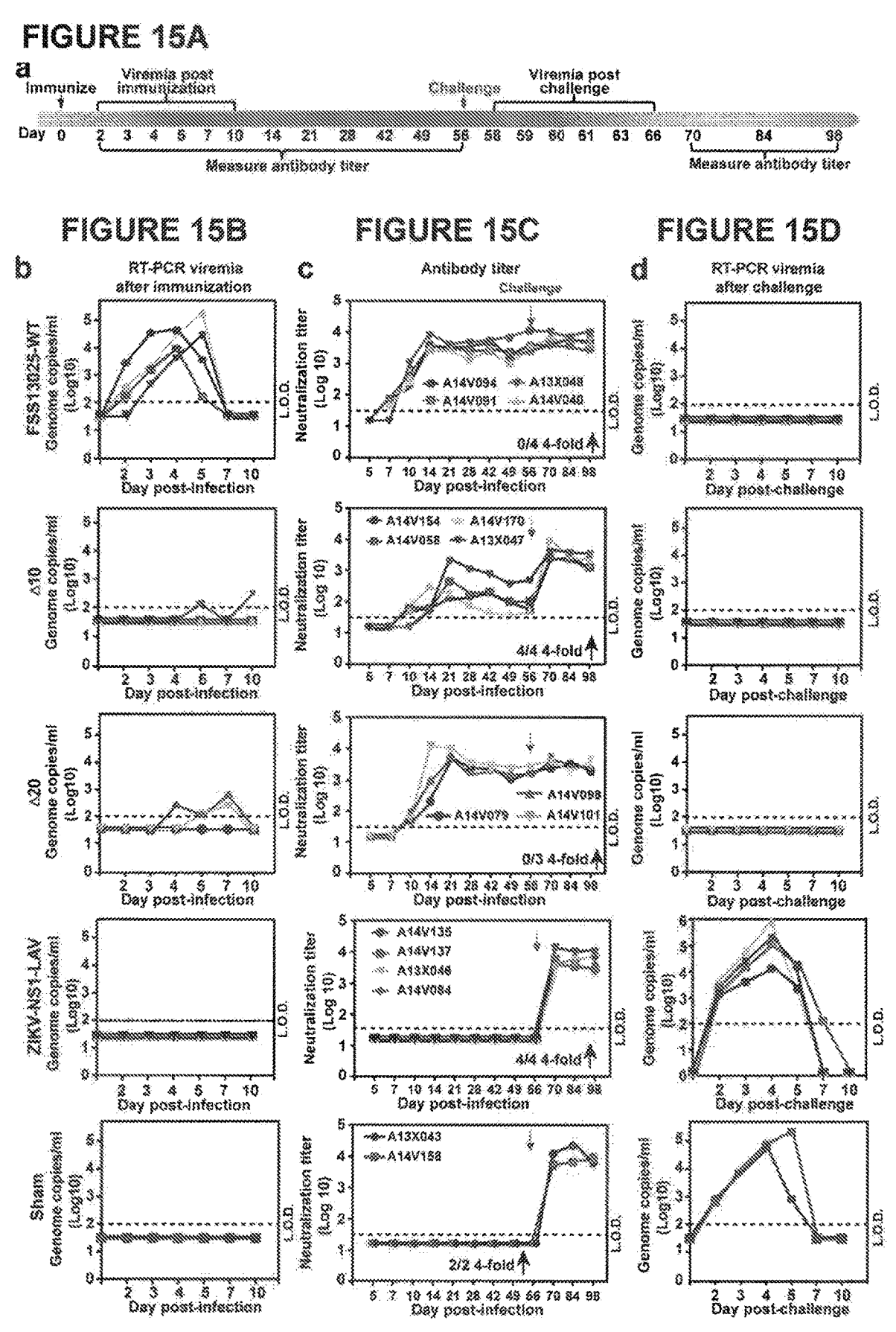

FIG. 15A-D shows that ZIKV-3'UTR-Δ10-LAV and ZIKV-3'UTR-Δ20-LAV protect rhesus macaques (RM) from ZIKV infection. FIG. 15A shows the scheme of immunization of RM with 10$^3$ FFU of WT ZIKV strain FSS13025 (n=4), ZIKV-3'UTR-Δ10-LAV (A10; n=4), ZIKV-3'UTR-Δ20-LAV (A20; n=3), or PBS sham (n=2) via the subcutaneous route. FIG. 15B shows viremia measured at day 2, 3, 4, 5, 7, and 10 post-immunization by qRT-PCR. Each colored line represents data from different animals in each group. The dashed line indicates the limit of detection (L.O.D.) of the assay. FIG. 15C shows pre- and post-challenge antibody neutralization titers. On various days post-immunization, sera were measured for neutralizing titers using an mCherry ZIKV infection assay. Red arrows indicate challenge with $10^3$ FFU of epidemic ZIKV strain PRVABC59 via the subcutaneous route at day 56 post-immunization. The number of animals whose antibody neutralization titers increased by ≥4-fold after challenge is indicated by symbol "↑" for each experimental group. FIG. 15D shows post-challenge viremia. Viremia was measured by qRT-PCR at day 2, 3, 4, 5, 7, and 10 post-challenge. All negative samples are plotted at the half value of L.O.D. Error bars represent standard deviations.

FIG. 16A-H shows a safety evaluation of ZIKV-3'-UTR-Δ20-LAV (A20) vaccine candidate. FIG. 16A shows viral loads in organs of infected A129 mice. Three-week-old A129 mice (n=7) were subcutaneously immunized with $10^3$ FFU of WT ZIKV FSS13025 (left panel) and its derivative Δ20 vaccine candidate (right panel). Organs from infected mice were collected and homogenized at day 6 and 10 post-infection. The amounts of viruses were quantified on Vero cells using a focus forming assay. The mean results from seven animals are presented. Bars denote standard errors. The dashed lines indicate the limit of detection (L.O.D.) of the assay. FIG. 16D-F shows the effect of Δ20 vaccination on the testis. Three-week-old A129 mice (n=5) were subcutaneously infected with $1 \times 10^3$ FFU of WT ZIKV FSS13025 or Δ20 vaccine candidate. At day 28 post-infection, animals from each group were analyzed for testis weight (FIG. 16B), testis size (FIG. 16C), total sperm counts (FIG. 16D), motile sperm counts (FIG. 16E), and viral RNA load (FIG. 16F). Scale bar, 1 mm. (FIG. 16G) Comparison of neurovirulence of WT ZIKV FSS13025 and Δ20 vaccine candidate in outbred CD-1 mice. One-day-old CD-1 mice (n=7-8 per group) were injected intracranially with 10 to $10^4$ FFU of WT ZIKV or $10^3$ to $10^4$ FFU of Δ20 vaccine candidate. Survival mice and total infected animals are indicated. (FIG. 16H) Analysis of vector competency. *Aedes aegypti* were fed on artificial blood-meals spiked with $10^6$ FFU/ml of WT ZIKV FSS13025 or Δ20 vaccine virus. At day 7 post-feeding, individual engorged mosquitoes were assayed for infection by immunostaining of viral protein expression on inoculated Vero cells. The number of infected mosquitos and total number of engorged mosquitoes are indicated. Asterisks indicate significant differences (One-way ANOVA: *, P value<0.001; , P value<0.01; *, P value<0.05). Non-significant (n.s.) with P value>0.5. All negative samples are plotted at the half value of L.O.D. Error bars represent standard deviations.

FIG. 17A-C shows the infectious ZIKV burden in placentas and fetal heads from sham or ZIKV-3'UTR-Δ10-LAV-immunized dams. In the pregnancy protection experiment (see details in FIG. 13), at day 7 post-challenge (equivalent to E13), placenta (FIG. 17A) and fetal heads (FIG. 17B) were collected from PBS sham and ZIKV-3'UTR-Δ10-LAV-immunized dams, and quantified for infectious ZIKV using a focus forming assay. Dashed lines indicate limit of detection (L.O.D.) of the assays. Results are pooled from two independent biological experiments, and each symbol represents data from an individual placenta (n=23) or fetus (n=30). (FIG. 17C) Correlation of E13 placenta viral burden with antibody neutralizing $NT_{50}$ values of ZIKV-3'UTR-Δ10-LAV. P and $R^2$ values reflect Pearson correlation tests. All negative samples are plotted at the half value of L.O.D. Error bars represent standard deviations.

FIG. 18 A-I contains experiments which show that ZIKV-3'UTR-Δ10-LAV protects adult A129 male mice against testis infection and injury. (A) Scheme of immunization of 15-week-old A129 male mice with $1 \times 10^4$ FFU of ZIKV-3'UTR-Δ10-LAV (A10; n=5) or PBS sham (n=5). At day 28 post-immunization, mice were measured for neutralizing antibody titers. On the same day, the mice were challenged with $10^6$ FFU of ZIKV-PRVABC59. Peak viremia was measured at day 2 post-challenge (day 30 post-immunization). At day 49 post-immunization, mice were euthanized and measured for total and motile sperm counts and viral loads in the testis. FIG. 18B shows viremia after ZIKV-3'UTR-Δ10-LAV immunization. FIG. 18C shows $NT_{50}$ values of antibody neutralization at day 28 post-immunization. Antibody neutralizing titers were measured for individual animals in each group by an mCherry ZIKV. The dashed lines indicate the limit of detection (L.O.D.) of the assay. FIG. 18D shows day 2 post-challenge (day 30 post-immunization) viremia. At day 21 post-challenge, animals from each group were analyzed for testis viral load FIG. 18E shows testis viral load, FIG. 18F shows total sperm counts, FIG. 18G shows motile sperm counts, FIG. 18H shows testis weight, and FIG. 18I shows testis size. Representative images of testis are presented in (i). Scale bar, 1 mm. Asterisks indicate significant differences (One-way ANOVA: *, P value<0.05; , P value<0.01; **, P value<0.0001). Non-significant (n.s.), P value>0.5. All negative samples are plotted at the half value of L.O.D. Error bars represent standard deviations.

Figure 19A:
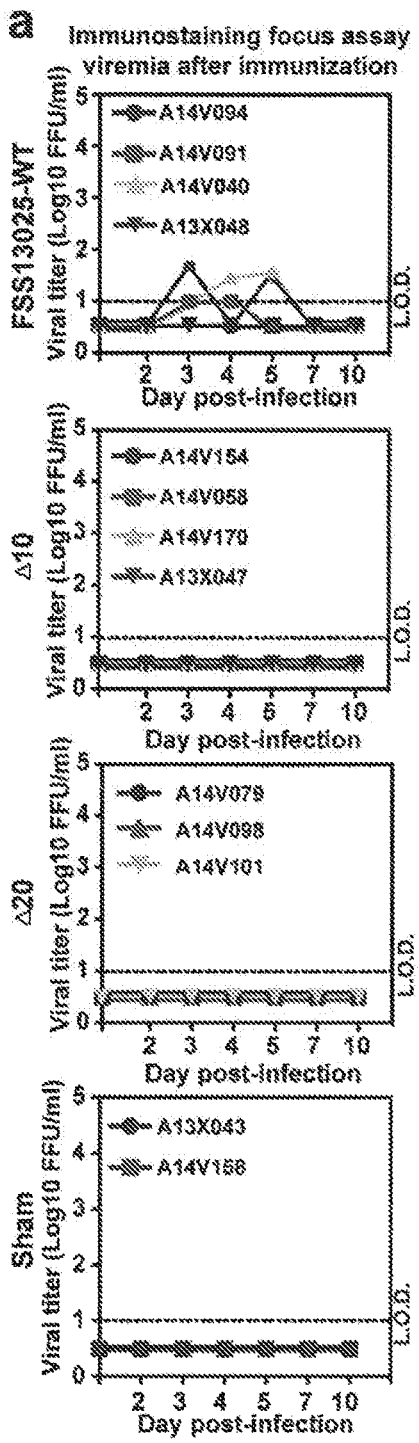
Figure 19B:
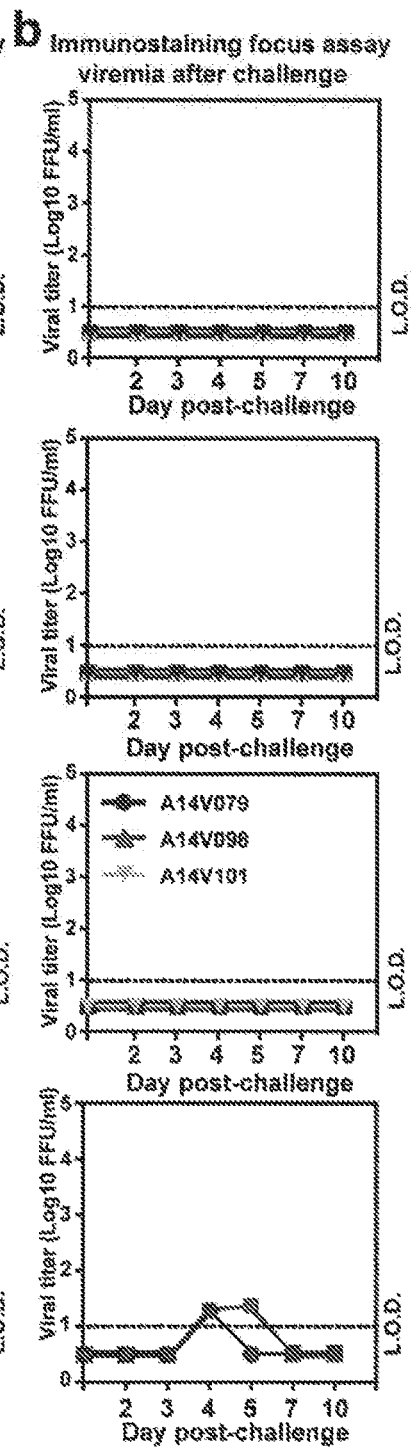

FIG. 19A-B shows infectious virus in serum of challenged rhesus macaque. Infectious virus in RM serum (viremia) was collected at days 2, 3, 4, 5, 7, and 10 post-immunization (FIG. 19A) or post-challenge (FIG. 19B) was quantified by a focus forming assay. (See detailed experimental scheme in FIG. 15A-D). Dashed lines indicate limit of detection (L.O.D.) of the assays. All negative samples are plotted at the half value of L.O.D.

FIG. 20A-I shows that ZIKV-3'-UTR-Δ20-LAV protects young A129 male mice against testis infection and injury. FIG. 20A shows the scheme of immunization of 3-week-old A129 male mice with $10^3$ FFU of ZIKV-3'-UTR-Δ20-LAV (A20; n=6) or PBS sham (n=4 or 6). FIG. 20B shows viremia post immunization. At day 28 post-immunization, immunized mice were measured for neutralization antibody titers. At the same day, mice from one sham group and mice from A20-immunized group were challenged with $10^6$ FFU of ZIKV-PRVABC59. FIG. 20D shows viremia measured at day 2 post-challenge (day 30 post-immunization). FIGS. 20E&F show that at day 49 post-immunization, mice were analyzed for sperm counts and viral loads in testis. FIG. 20C shows $NT_{50}$ values of antibody neutralization at day 28 post-immunization were measured for individual animals in each group. The dashed lines indicate the limit of detection (L.O.D.) of the assay. FIG. 20D shows day 2 post-challenge (day 30 post-immunization) viremia. FIGS. 20E & F respectively show total (E) and motile (F) sperm counts at day 21 post-challenge (equivalent to day 49 post-immunization). FIG. 20G shows testis weight from animals from sham, sham with challenge, and A20-immunized and challenged groups at day 21 post-challenge. FIG. 20H shows viral load in testis at day 21 post-challenge. FIG. 20I contains representative images of testis harvested at day 21 post-challenge. Scale bar, 1 mm. Asterisks indicate significant differences (One-way ANOVA: ****, P value<0.0001). Non-significant (n.s.) with P value>0.5. All negative samples are plotted at the half value of L.O.D. Error bars represent standard deviations.

FIG. 21 contains a summary of experiments which evaluated the stability of ZIKV-3'UTR-Δ20-LAV in cell culture. P0 viruses (derived from the culture fluids of RNA-transfected cells) were continuously cultured on Vero cells for five rounds (5 days for each round of culture), resulting in P5 viruses. The complete genomes of P5 mutant viruses were sequenced. All P5 viruses retained the 20-nucleotide deletion in the 3'UTR. In addition, several adaptive mutations are recovered; these mutations are presented by their amino acid positions of indicated genes based on ZIKV FSS13025 strain (GenBank number KU955593.1). Results from three independent passages are presented.

Figure 22:
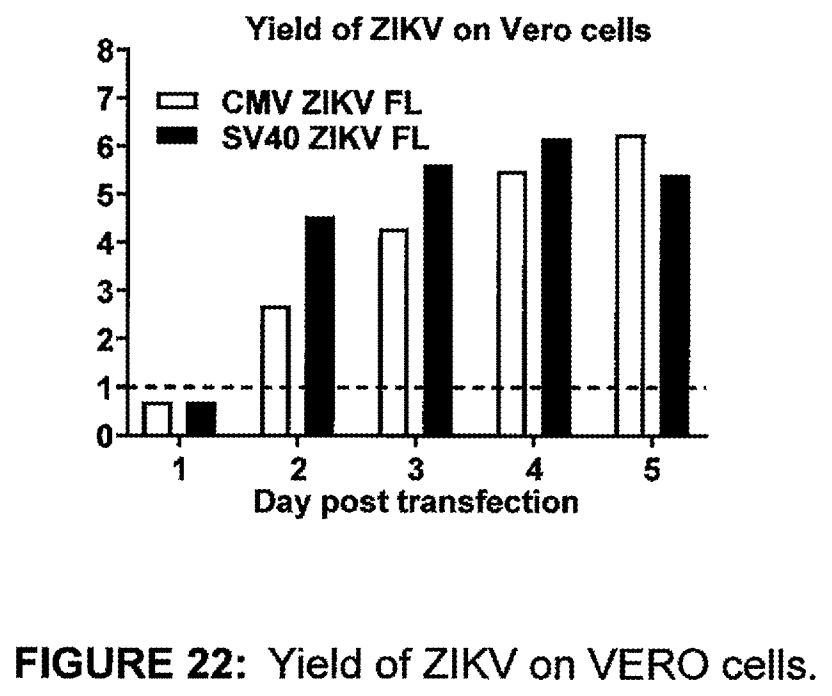

FIG. 22 depicts the results of experiments wherein 5 micrograms of a Zika DNA plasmid according to the invention was transfected into Vero cells through electroporation. Culture fluids were collected from day 1 to 5. Infectious viral titers were measured by plaque assay on Vero cells.

FIG. 23 shows the yield of ZIKV DNA vaccine candidates on Vero cells. Five micrograms of indicated DNA plasmid was transfected into Vero cells through electroporation. Culture fluids were collected from day 1 to 5. Infectious viral titers were measured by plaque assay on Vero cells.

DETAILED DESCRIPTION OF THE INVENTION

The present invention in general relates to the construction and characterization of a novel live attenuated Zika virus (ZIKV) strain having one or more deletions in the 3' untranslated region (3'UTR). These ZIKV deletion mutants may have reduced RNA production and increased susceptibility to interferon-β inhibition, and thus can be utilized as effective live attenuated vaccines against ZIKV. Particularly we show herein that live-attenuated ZIKV vaccine candidates containing deletions in the 3' untranslated region of the ZIKV genome (ZIKV-3'UTR-LAV) prevent viral transmission during pregnancy and testis damage in mice, as well as inhibiting infection in non-human primates. We also demonstrate a desirable safety profile of the vaccine candidates. Our results suggest that ZIKV-3'UTR-LAV potentially may be used to vaccinate humans against Zika virus infection.

Moreover, as evidenced by the results disclosed herein mutated live attenuated Zika virus strains according to the invention and compositions containing same may be used in treating or providing immunoprotection against infections elicited by ZIKV, including congenital ZIKV syndrome, microcephaly, and Guillan-Barre syndrome (GBS).

The present invention provides a vaccine which may be used to prevent viremia in pregnant women and travelers to epidemic/endemic regions to avert congenital ZIKV syndrome and which may also be useful to suppress epidemic transmission. The ZIKV strain of the invention is a live-attenuated vaccine candidate that contains a deletion or "Δ" in the 3' untranslated region of ZIKV genome, preferably a 10-nucleotide deletion (10-del ZIKV) or a 20-nucleotide deletion (20-del ZIKV) and more preferably comprising or consisting of the Zika strains having the sequences in Appendix A modified as set forth in Appendix B. The 10-del ZIKV is highly attenuated, immunogenic, and protective in the A129 mouse model. A single dose of 10 IFU of 10-del ZIKV elicited a high level of neutralizing antibodies and completely prevented viremia after challenge. Besides the antibody response, the immunized mice also developed a robust T cell response. Intracranial inoculation of one-day-old CD1 mice with $1\times10^4$ IFU of 10-del ZIKV caused no detectable disease, whereas infections with 10 IFU of wild-type ZIKV were lethal. Mechanistically, the 10-del ZIKV attenuated its virulence through decreased viral RNA synthesis and increased sensitivity to type-I interferon inhibition. The attenuated 10-del ZIKV was incompetent in infecting mosquitoes, representing an additional safety feature for use in non-endemic regions. Collectively, the safety and efficacy results warrant further development of this promising live-attenuated ZIKV vaccine candidate.

The live attenuated ZIKV strains of the invention may further comprise additional mutations to the ZIKV genome. A mutation can be, but is not limited to, a deletion of noncoding or coding nucleotides, a deletion of one or more amino acids, an addition of one or more amino acids, a substitution (conserved or non-conserved) of one or more amino acids or a combination thereof. ZIKV can be mutated, e.g., using deletions to the 3'UTR, such that the infectivity of ZIKV is reduced. In certain embodiments, the infectivity of ZIKV is reduced by a factor of at least 5, 10, 50, 100, 500, 10, $5\times10^3$, $10^4$, $5\times10^4$, $10^5$, $5\times10^5$, or at least $10^6$.

Additionally, ZIKV can be mutated, e.g., having deletions to the 3'UTR and/or using point mutations, such that the rate of replication of the recombinant virus is reduced or increased. The rate of replication can be determined by any standard technique known to the skilled artisan. The rate of replication is represented by the growth rate of the virus and can be determined by plotting the viral titer over the time post infection. The viral titer can be measured by any technique known to the skilled artisan. In certain embodiments, a suspension containing the virus is incubated with cells that are susceptible to infection by the virus including, but not limited to, Vero cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF). Subsequent to the incubation of the virus with the cells, the number of infected cells is determined. In certain specific embodiments, the virus comprises a reporter gene. Thus, the number of cells expressing the reporter gene is representative of the number of infected cells. In a specific embodiment, the virus comprises a heterologous nucleotide sequence encoding mCherry, and the number of cells expressing mCherry, i.e., the number of cells infected with the virus, is determined using FACS.

The assays described herein may be used to assay viral titre over time to determine the growth characteristics of the virus. In a specific embodiment, the viral titre is determined by obtaining a sample from the infected cells or the infected subject, preparing a serial dilution of the sample and infecting a monolayer of cells that are susceptible to infection with the virus at a dilution of the virus that allows for the emergence of single plaques. The plaques can then be counted and the viral titre express as plaque forming units per milliliter of sample. In a specific embodiment of the invention, the growth rate of a virus of the invention in a subject is estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is best tested by sampling biological fluids of a host at multiple time points post-infection and measuring viral titer.

The expression of heterologous gene sequence in a cell culture system or in a subject can be determined by any technique known to the skilled artisan. In certain embodiments, the expression of the heterologous gene is measured by quantifying the level of the transcript. The level of the transcript can be measured by Northern blot analysis or by RT-PCR using probes or primers, respectively that are specific for the transcript. The transcript can be distinguished from the genome of the virus because the virus is in the antisense orientation whereas the transcript is in the sense orientation. In certain embodiments, the expression of the heterologous gene is measured by quantifying the level of the protein product of the heterologous gene. The level of the protein can be measured by Western blot analysis using antibodies that are specific to the protein.

The invention provides a live attenuated ZIKV strain comprising a deletion of one or more nucleotides in the 3'UTR of the ZIKV genome. In some embodiments, the ZIKV strain of the invention may comprise a 1-nucleotide deletion, a 2-nucleotide deletion, a 3-nucleotide deletion, a 4-nucleotide deletion, a 5-nucleotide deletion, a 6-nucleotide deletion, a 7-nucleotide deletion, an 8-nucleotide deletion, a 9-nucleotide deletion, a 10-nucleotide deletion, an 11-nucleotide deletion, a 12-nucleotide deletion, a 13-nucleotide deletion, a 14-nucleotide deletion, a 15-nucleotide deletion, a 16-nucleotide deletion, a 17-nucleotide deletion, an 18-nucleotide deletion, a 19-nucleotide deletion, a 20-nucleotide deletion, 21-nucleotide deletion, a 22-nucleotide deletion, a 23-nucleotide deletion, a 24-nucleotide deletion, a 25-nucleotide deletion, a 26-nucleotide deletion, a 27-nucleotide deletion, a 28-nucleotide deletion, a 29-nucleotide deletion, a 30-nucleotide deletion, 31-nucleotide deletion, a 32-nucleotide deletion, a 33-nucleotide deletion, a 34-nucleotide deletion, a 35-nucleotide deletion, a 36-nucleotide deletion, a 37-nucleotide deletion, a 38-nucleotide deletion, a 39-nucleotide deletion, a 40-nucleotide deletion, a 41-nucleotide deletion, a 42-nucleotide deletion, a 43-nucleotide deletion, a 44-nucleotide deletion, a 45-nucleotide deletion, a 46-nucleotide deletion, a 47-nucleotide deletion, a 48-nucleotide deletion, a 49-nucleotide deletion, or a 50-nucleotide deletion in the 3'UTR of the ZIKV genome.

The live attenuated ZIKV strains of the present invention, nucleotide sequences encoding the same, vectors encoding the same, and cells comprising nucleotide sequences encoding said strains may be further modified, engineered, optimized, or appended in order to provide or select for various features. In addition to deletions within the 3'UTR, the attenuated virus may also contain other mutations including, but not limited to, replacing a gene of the human virus with the analogous gene of a virus of a different species, of a different subgroup, or of a different variant.

In some embodiments, other mutations may be introduced into the virus (e.g., missense mutations) can be introduced into the C, prM, E, NS1, NS2A, NS2B, NS3, NS4A, NS4B, or NS5 proteins of the recombinant virus. Also, the mutations may include additions, substitutions, deletions, or combinations thereof. For example a deletion mutation in any of the C, prM, E, NS1, NS2A, NS2B, NS3, NS4A, NS4B, or NS5 proteins may be introduced. In other embodiments, a missense mutation may be introduced which results in a cold-sensitive mutation or a heat-sensitive mutation. In some embodiments, major phosphorylation sites of viral protein may be removed.

In other embodiments, deletions are introduced into the genome of the recombinant virus. In more specific embodiments, a deletion can be introduced into the C, prM, E, NS1, NS2A, NS2B, NS3, NS4A, NS4B, or NS5 proteins of the recombinant virus.

In certain embodiments, the intergenic region of the recombinant virus is altered. In one embodiment, the length of the intergenic region is altered. In another embodiment, the intergenic regions may be shuffled from 5' to 3' end of the viral genome. In other embodiments, the genome position of a gene or genes of the recombinant virus can be changed.

In certain embodiments, attenuation of the virus is further enhanced by replacing a gene of the wild type virus with a gene of a virus of a different species, of a different subgroup, or of a different variant.

The attenuated phenotypes of a recombinant virus of the invention can be tested by any method known to the artisan. A candidate virus can, for example, be tested for its ability to infect a host or for the rate of replication in a cell culture system. In certain embodiments, growth curves at different temperatures are used to test the attenuated phenotype of the virus. For example, an attenuated virus is able to grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In certain embodiments, the ability of the recombinant virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

Various assays can be used to test the safety of a vaccine. For example, sucrose gradients and neutralization assays can be used to test the safety. A sucrose gradient assay can be used to determine whether a heterologous protein is inserted in a virion. If the heterologous protein is inserted in the virion, the virion should be tested for its ability to cause symptoms even if the parental strain does not cause symptoms. Without being bound by theory, if the heterologous protein is incorporated in the virion, the virus may have acquired new, possibly pathological, properties.

Attenuated virus produced according to the invention will be used to confer prophylactic or therapeutic protection in susceptible hosts against ZIKV infection, e.g., to treat or prevent ZIKV infection and/or to prevent congenital ZIKV syndrome or GBS. The attenuated ZIKV strain may be formulated using known techniques for formulating attenuated viral vaccines or immunogenic compositions of viral vaccines.

In one embodiment, the 3'UTR of the ZIKV strain of the invention comprises the nucleic acid sequence of the 3'UTR of the 10-del mutant ZIKV strain, SEQ ID NO: 2.

In one embodiment, the 3'UTR of the ZIKV strain of the invention comprises the nucleic acid sequence of the 3'UTR of the 20-del mutant ZIKV strain, SEQ ID NO: 3.

In one embodiment, the 3'UTR of the ZIKV strain of the invention comprises the nucleic acid sequence of the 3'UTR of the 30-del-a mutant ZIKV strain, SEQ ID NO: 4.

In one embodiment, the 3'UTR of the ZIKV strain of the invention comprises the nucleic acid sequence of the 3'UTR of the 30-del-b mutant ZIKV strain, SEQ ID NO: 5.

In some exemplary embodiments the ZIKV strain of the invention comprises or consists of the sequences set forth in Appendix A modified as set forth in Appendix B.

In some exemplary embodiments immunogenic compositions are provided containing a therapeutically or prophylactically effective amount of a ZIKV strain which comprises or consists of the sequences set forth in Appendix A modified as set forth in Appendix B.

In some exemplary embodiments individuals in need thereof are administered therapeutically or prophylactically effective amount of a ZIKV strain which comprises or consists of the sequences set forth in Appendix A modified as set forth in Appendix B.

Administration

The immunogenic compositions of the present invention may be administered in a number of ways depending upon whether local or systemic treatment is desired. In exemplary embodiments administration may be topical, parenteral, or enteral.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories for the lower intestinal tract of the alimentary canal.

Preferably, the formulated virus containing composition is suitable for intranasal, injection, topical or oral administration, for example as a dried stabilized powder for reconstitution in a suitable buffer prior to administration or in an aerosol composition. In a preferred embodiment, the composition is intranasally administered.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams microsponges, liposomes, nanoemulsions, aerosol foams, polymers, fullerenes, and powders (see, e.g., Reference 35, Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin, cationic glycerol derivatives, and polycationic molecules, such as polylysine, also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvants, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxychoalate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (Triton N-101, Octoxynol 9), Octoxinol-9 (Triton X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenolsulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

The vaccine or immunogenic composition may be used in the vaccination of a mammalian host, particularly a human, nonhuman primate, ape, monkey, horse, cow, carabao, goat, duck, bat, or other suitable non-human host. A dosage may comprise at least 10 IFU, $10^1$ IFU, $10^2$ IFU, $10^3$ IFU, $10^4$ IFU, $5\times10^4$ IFU, $10^5$ IFU, $5\times10^5$ IFU, $10^6$ IFU, $5\times10^6$ IFU, $10^7$ IFU, $5\times10^7$ IFU, $10^8$ IFU, or $5\times10^8$ IFU of said live attenuated ZIKV strain. In some instances the subject may be immunocompromised or may have another condition, e.g., may be pregnant.

Definitions

The "3'UTR" or "3' untranslated region" or "three prime untranslated region" of the ZIKV genome corresponds to the section of RNA that immediately follows the translation termination codon of the genomic polyprotein.

An "adjuvant" refers to a substance that enhances an immune response, e.g., an antibody or cell-mediated immune response against a specific agent, e.g., an antigen, or an infectious agent.

An "attenuated" or "live attenuated" virus strain refers a mutated or modified or recombinant virus having reduced or no virulence or propensity to cause a disease or infection normally associated with the "wild-type" or "unmodified" (or in this case "non-mutated") virus.

An "attenuated" or "live attenuated" ZIKV strain, in particular, refers to a ZIKV strain that has been modified to have reduced or no virulence or propensity to cause a disease or infection which is normally associated with a "wild-type" or "unmodified" or "non-mutated" virus, in particular congenital ZIKV syndrome or GBS. More particularly, this includes "attenuated" ZIKV strains that are "modified" or "altered" or "mutated" to have one or more deletions in the 3'UTR of the ZIKV genome, e.g., a 10-nucleotide, 20-nucleotide, or 30-nucleotide deletion in the 3'UTR, preferably a 10-nucleotide deletion. The deletions may not disrupt RNA translation. The deletions may slow RNA production and increase interferon-β susceptibility. Such live attenuated ZIKV strain elicits immunoprotection against the virus, i.e., maintains an important immunogenic epitope.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter. The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

An "immunogenic composition" herein refers to a composition containing a live attenuated ZIKV strain according to the invention which elicits an immune response in a susceptible host, e.g., an antibody, Th1 or cellular (e.g., T cell-mediated) immune response.

An "isolated" biological component (such as an isolated bacterium or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

A "pharmaceutically acceptable carrier" or "excipient" refers to compounds or materials conventionally used in immunogenic or vaccine compositions during formulation and/or to permit storage.

"Prophylactically effective amount" of a live attenuated ZIKV strain according to the invention refers to an amount sufficient to prevent or reduce the incidence of infection in a susceptible host.

The term "recombinant" means a polynucleotide with semisynthetic, or synthetic origin which either does not occur in nature or is linked to another polynucleotide in an arrangement not found in nature.

A "susceptible host" herein refers to a host or animal that may be infected by ZIKV. Such hosts include humans or animals, e.g., a human, nonhuman primate, ape, monkey, horse, cow, carabao, goat, duck, bat, or other suitable non-human host.

"Therapeutically effective amount" of a live attenuated ZIKV strain according to the invention refers to an amount sufficient to treat ZIKV infection or a disease associated therewith in a susceptible host.

A "vaccine" composition herein refers to a composition containing a live attenuated ZIKV strain according to the invention which elicits a therapeutic or prophylactic immune response against ZIKV.

"ZIKV infection" or "infection elicted by ZIKV" herein refers to the infection of a susceptible host with ZIKV and diseases associated therewith, including congenital ZIKV syndrome and Guillan-Barré syndrome (GBS).

The following examples are offered to illustrate, but not to limit, the claimed invention.

EXAMPLES

Example 1: Generating Live Attenuated ZIKV Strains with 3'UTR Deletions

Materials and Methods:
Viruses: The ZIKV Cambodian strain FSS13025 (GenBank number KU955593.1) was generated from an infectious cDNA clone pFLZIKV as described previously (Reference 10). All the cell lines are tested negative for mycoplasma.

Plasmid construction. Standard molecular biology procedures were performed for all plasmid constructions. Standard overlap PCR was performed to amplify the DNA fragment between unique restriction enzyme sites EcoRI and ClaI using corresponding primer pairs. The DNA fragment containing 3'UTR deletion mutations were individually introduced into the pFLZIKV and pZIKV Rep (replicon cDNA plasmid, Reference 11) through EcoRI and ClaI. All the constructs were verified by DNA sequencing. Primer sequences are available upon request. All restriction enzymes were purchased from New England BioLabs (Ipswitch, Mass.).

Results:
We chose to pursue a live-attenuated vaccine to capitalize on its advantages of single-dose immunization, a rapid and robust immune response, and long-lived protection. We attenuated wild-type (WT) ZIKV through deletion of a portion of the 3' untranslated region (3'UTR) of the viral genome, as has been successfully used to develop a DENV vaccine currently in a phase III clinical trial (Reference 9). Using an infectious cDNA clone of the ZIKV Cambodian strain FSS13025 (Reference 10) (which is closely related to strains now circulating in the Americas), we prepared a panel of recombinant viruses containing distinct 3'UTR deletions (FIG. 1A). Mutants 10-del, 20-del, 30-del-a, and 30-del-b contained overlapping 10-to-30-nucleotide deletions, which were expected to change the local secondary structure of the viral 3'UTR (FIG. 2).

Example 2: Replication and IFN-0 Inhibition Analysis of ZIKV 3'UTR Deletion Mutants Materials and Methods:

Cells and antibodies. Vero cells were purchased from the American Type Culture Collection (ATCC, Bethesda, Md.), and maintained in a high glucose Dulbecco modified Eagle medium (DMEM) (Invitrogen, Carlsbad, Calif.) supplemented with 10% fetal bovine serum (FBS) (HyClone Laboratories, Logan, Utah) and 1% penicillin/streptomycin (Invitrogen, Carlsbad, Calif.) at 37° C. with 5% $CO_2$. The following antibodies were used in this study: a mouse monoclonal antibody (mAb) 4G2 cross-reactive with flavivirus E protein (ATCC), ZIKV-specific HMAF (hyper-immune ascitic fluid), World Reference Center of Emerging Viruses and Arboviruses (WRCEVA) at the University of Texas Medical Branch], Anti-Mouse IgG (H+L) Antibody Horseradish Peroxidase-labeled (KPL, Gaithersburg, Md.), and goat anti-mouse IgG conjugated with Alexa Fluor 488 (Thermo Fisher Scientific).

RNA transcription and transfection. Full-genome ZIKV, mCherry ZIKV, and replicon RNAs were in vitro transcribed using a T7 mMessage mMachine kit (Ambion, Austin, Tex.) from cDNA plasmids pre-linearized by ClaI. The RNA was precipitated with lithium chloride, washed with 70% ethanol, re-suspended in RNase-free water, quantitated by spectrophotometry, and stored at –80° C. in aliquots. The RNA transcripts (10 µg) were electroporated into Vero cells following a protocol described previously (Reference 31).

Indirect immunofluorescence assays (IFA). Vero cells were electroporated with 10 µg of genomic WT or 3'UTR deletion RNA of ZIKV and grown in an 8-well Lab-Tek chamber slide (Thermo Fisher Scientific, Waltham, Mass.). On day 2 and 3 post-transfection, the cells were fixed in 100% methanol at –20° C. for 15 min. After 1 h incubation in a blocking buffer containing 1% FBS and 0.05% Tween-20 in PBS, the cells were treated with a mouse monoclonal antibody 4G2 for 1 h and washed three times with PBS (5 min for each wash). The cells were then incubated with Alexa Fluor® 488 goat anti-mouse IgG for 1 h in blocking buffer, after which the cells were washed three times with PBS. The cells were mounted in a mounting medium with DAPI (4', 6-diamidino-2-phenylindole; Vector Laboratories, Inc.). Fluorescence images were observed under a fluorescence microscope equipped with a video documentation system (Olympus).

Immunostainingfocus assay of mutant viruses. Equal amounts of RNAs (10 µg) transcribed from their corresponding infectious cDNA clones were electroporated into Vero cells. On day 4 or 5 post-transfection, culture fluids form the transfected cells were harvested and quantified for infectious viruses (defined as P0 virus) using an immunostaining focus assay on Vero cells.

Immunostainingfocus assay and immunostaining. Viral samples were ten-fold serially diluted six times in DMEM. For each dilution, 100 µl sample was added to a 24-well plate containing Vero cells at about 90% confluency. The infected cells were incubated for 1 h and swirled every 15 min to ensure complete coverage of the monolayer for even infection. After 1 h incubation, 0.5 ml of methyl cellulose overlay containing 2% FBS 1% penicillin/streptomycin was added to each well. The plate was incubated at 37° C. for four days. Following the incubation, methyl cellulose overlay was removed and 0.5 ml methanol-acetone (1:1) solution was added into each well and incubated at room temperature for 15 min. Fixation solution was aspirated and plates were allowed to air dry, then washed three times with PBS and incubated in blocking buffer (PBS supplemented with 3% FBS), followed by 1 h incubation with ZIKV-specific HMAF. Plates were washed three times with PBS followed by an hour-long incubation with a secondary antibody conjugated to horseradish peroxidase (KPL, Gaithersburg, Md.). Detection proceeded with the addition of aminoethylcarbazole substrate (ENZO Life sciences, Farmingdale, Mass.) prepared according to the vendor's instructions.

Luciferase assay. The luciferase assay was performed as previously reported (Reference 11). Briefly, Vero cells transfected with WT or mutant ZIKV replicon RNAs (10 µg) were seeded in a 12-well plate. At various time points, the cells were washed once with phosphate-buffered saline (PBS) and lysed using cell lysis buffer (Promega, Madison, Wis.). The cells were scraped from plates and stored at –80° C. The luciferase signals were measured by Cytation 5 (Biotek) according to the manufacturer's instructions.

Replication curves. Subconfluent Vero cells in 24-well plates ($2\times10^5$ cells per well) were infected with WT or mutant P0 ZIKV at a multiplicity of infection (MOI) of 0.01 in triplicate wells. Virus stocks were diluted in DMEM containing 2% FBS and 1% penicillin/streptomycin. One hundred microliters of virus were added to each well of the 12-well plates. After 1 h attachment (5% $CO_2$ at 37° C.), the inocula were removed, monolayers were washed three times with PBS, and 1 ml DMEM medium containing 2% FBS and 1% penicillin/streptomycin was added to each well. Culture fluids were quantified for infectious viruses on days 1 to 5 using the immunostaining focus assay.

Replicon analysis of the 3'UTR deletions. A Renilla luciferase reporter replicon of ZIKV was engineered with various 3'UTR deletions. Equal amounts of replicon WT and mutant RNAs (10 µg) were electroporated into Vero cells. Luciferase signals were measured at several time points. A non-replicative replicon containing an NS5 polymerase-inactive GDD mutation was included as a negative control.

Interferon-β inhibition of WT and mutant ZIKVs. Vero cells were seeded in 96-well plate ($1.5\times10^4$ cell per well) one day before interferon treatment and viral infection. The cells were infected at an MOI 0.05 in the presence of IFN-β (55, 167, 500, or 1,500 IU/ml). Viral infection and interferon treatment were initiated at the same time. At 48 h post-infection and interferon-β treatment, viral titers were quantified using the immunostaining focus assay on Vero cells.

Results:

Upon transfection into Vero cells, all mutant genomic RNAs generated viral E protein-expression cells (FIG. 3) and infectious viruses (defined as P0 viruses). Compared with the WT, all mutants exhibited smaller infectious foci (FIG. 1B), slower replication kinetics, and lower peak titers (FIG. 1C). To examine the mutational effects on viral replication, we engineered the deletions into a luciferase ZIKV replicon (Reference 11). The replicon results showed that the 3'UTR deletions did not affect viral RNA translation (indicated by the luciferase signals at 2-6 h post-transfection), but decreased RNA synthesis (indicated by the luciferase activities at 24-48 h post-transfection; FIGS. 1D & 1E); a similar observation was previously reported for West Nile virus, a closely related flavivirus (Reference 12). Since the 3'UTR of flavivirus may also modulate host innate immune response (References 13, 14), we compared the susceptibility of the WT and mutant viruses to interferon inhibition. All four mutant viruses were much more sensitive to interferon-β inhibition than the WT virus, among which mutant 10-del exhibited the greatest inhibition (FIG. 1F). Collectively, these results indicate that 3'UTR deletions attenuate ZIKV replication through diminished viral RNA synthesis and increased vulnerability to type-I interferon inhibition.

Example 3: Stability of Mutant Viruses

Materials and Methods:

Stability of 3'UTR mutants, RNA extraction, and RT-PCR. To examine the stability of 3'UTR mutants, we passaged them on Vero cells for five rounds (5 days for each round of culture). Briefly, $1.5 \times 10^6$ Vero cells were seeded into T-25 flask. The virus derived from RNA transfection, defined as P0 was used to infect the Vero cells. At 5 d p.i., culture fluid (100 µl) was transferred to a new T-25 flask containing Vero cells in 5 ml of culture medium. After five rounds of such passaging (P5), viral RNAs were extracted from the P5 culture fluids using QIAamp Viral RNA Kit (Qiagen). Viral RNAs were amplified by RT-PCR using SuperScript III one-step RT-PCR kits (Invitrogen). The P5 viruses were subjected to complete genome-length sequencing. Three independent passages were performed for each mutant virus.

Immunostainingfocus assay. WT and P5 mutant viruses were analyzed using an immunostaining focus assay on Vero cells. For each mutant virus, three independent selections were performed on Vero cells.

Replication kinetics. Subconfluent Vero cells in 24-well plates ($2 \times 10^5$ cells per well) were infected with WT and P5 mutant viruses at a multiplicity of infection (MOI) of 0.01 in triplicate wells. Virus stocks were diluted in DMEM containing 2% FBS and 1% penicillin/streptomycin. One hundred microliters of virus were added to each well of the 12-well plates. After 1 h attachment (5% $CO_2$ at 37° C.), the inocula were removed, monolayers were washed three times with PBS, and 1 ml DMEM medium containing 2% FBS and 1% penicillin/streptomycin was added to each well. Culture fluids were quantified for infectious viruses on days 1 to 5 using the immunostaining focus assay on Vero cells.

Results:

To test the stability of the mutant viruses, we passaged them five times on Vero cells (an approved cell line for vaccine production, see Reference 15). The passage 5 (P5) viruses developed larger infectious foci (FIG. 4A) and faster replication kinetics than the corresponding P0 viruses on Vero cells (Compare FIG. 4B with FIG. 1C). Complete genome sequencing of P0 and P5 viruses showed that all mutants retained the original deletions, but the P5 viruses had accumulated additional mutations in the E and/or NS1 genes, which presumably were Vero cell-adaptive mutation(s) and/or compensatory mutation(s) to 3'UTR deletions (FIG. 4C). In some embodiments, these mutations may be introduced into the infectious cDNA clone for vaccine production. Either way, the results indicated that the engineered deletions are stable when propagated on Vero cells, and further passaging of the mutant viruses on Vero cells to P20 did not change the engineered 3'UTR deletions.

Example 4: Characterization of 3'UTR mutants in the A129 Mouse Model

Materials and Methods:

Vaccination and challenge of mice. Three-week old A129 mice (n=8) were immunized by the subcutaneous (S.C.) route with $1 \times 10^4$ IFU WT and mutant viruses. Mock-infected mice were given PBS by the same route. Mice were weighed and monitored daily for progression of disease. Mice were anesthetized and bled via the retro orbital sinus (R.O.) every two days. Viremias were quantified by an immunostaining focus assay from day 2 to 4 post-infection. On day 28 post-immunization, mice were anesthetized and bled to measure neutralization antibody titers using a mCherry ZIKV infection assay. The vaccinated mice were then challenged via the intraperitoneal (IP.) route with $1 \times 10^5$ PFU parental virus (ZIKV strain FSS13025). On day 2 post-challenge, the mice were bled to measure viremia. Blood was clarified post collection by centrifugation at $3,380 \times g$ for 5 min and immediately stored at −80° C. for storage. Viral titers of sera and inoculum were determined by an immunostaining focus assay on Vero cells, as described above. All animal testing was performed in accordance with UTMB policy as approved by the UTMB IACUC.

Construction of mCherry ZIKV. A DNA fragment encoding the first 25 amino acids of C gene, the mCherry gene, and the foot-and-mouth virus 2A protein was in-frame fused with the open-reading-frame of ZIKV genome. The expression of mCherry in transfected Vero cells was analyzed by a fluorescent microscopy at days 2-6 post-transfection. The mCherry ZIKV was used to estimate antibody neutralization titers of mouse sera.

Antibody neutralization assay. Neutralizing activity of mouse sera was assessed using a newly established mCherry ZIKV. The sera were 2-fold serially diluted starting at 1:100 in DMEM with 2% FBS and 1% penicillin/streptomycin. Serial dilution of mice sera was incubated with mCherry ZIKV at 37° C. for 2 h. Antibody-virus complexes were added to pre-seeded Vero cells in 96-well plates. After 48 h post-infection, cells were visualized by fluorescence microscopy using Cytation 5 Cell Imaging Multi-Mode Reader (Biotek) to quantify the mCherry fluorescence-positive cells. The percentage of fluorescence-positive cells in the non-treatment controls was set at 100%. The fluorescence-positive cells from serum-treated wells were normalized to those of non-treatment controls. A four-parameter sigmoidal (logistic) model in the software GraphPad Prism 7 was used to calculate the neutralization titers ($NT_{50}$).

Results:

We evaluated the immunogenicity and efficacy of the mutant viruses in an A129 (interferon α/β receptor-deficient) mouse model (Reference 16) (FIG. 5A). After subcutaneous (S.C.) inoculation with $1 \times 10^4$ IFU of virus, mice infected with the WT virus had significantly more weight loss than those infected with mutant viruses; whereas the differences in mean weight loss among the four mutant virus-infected groups were not statistically significant (FIG. 5B). About 50% of the mice succumbed to the WT virus infection, whereas no mortality was observed in the mutant virus-infected mice (FIG. 5C). The WT virus produced significantly higher peak viremia than the mutant viruses, among which the 10-del virus had the lowest viremic profile (FIG. 5D). The viremia for 10-del mutant dropped to 700 IFU, 350 IFU, and undetectable on days 5, 6, and 7 post-infection, respectively. Sequencing analysis confirmed that the engineered deletions were retained without other mutations in the mutant viruses recovered from the mouse sera. On day 28 post-infection, mouse sera were taken and quantified for pre-challenge neutralization titers using an mCherry ZIKV (FIG. 6). Comparable pre-challenge neutralization titers of $(1.8 \pm 1.1) \times 10^3$ to $(8.6 \pm 1.5) \times 10^3$ were observed among the WT and mutant virus-infected mice (FIG. 5E). After challenge with $1 \times 10^5$ IFU of WT ZIKV (Cambodian strain FSS13025) on day 28 post-immunization, the immunized mice had no detectable peripheral viremia, whereas the mock-immunized group produced a mean viremia of $(8.5\pm1.5)\times10^6$ IFU/ml on day 2 post-challenge (FIG. 5F). On day 28 post-challenge, we measured the neutralization titers of the mouse sera again; remarkably, the post-challenge neutralization titers were equivalent to the pre-challenge neutralization titers (compare FIGS. 5E & 5G), suggesting that a sterilizing antibody response had been achieved by a single vaccination. Altogether, the results demonstrate that the mutant viruses are highly attenuated, immunogenic, and protective in A129 mice.

Example 5: Further Characterization of 10-Del Mutant ZIKV

Materials and Methods:

Viruses. The Puerto Rico strain PRVABC59 (GenBank number KU501215) was obtained from WRCEVA. All the cell lines are tested negative for mycoplasma.

Immunization with 100IFU 10-del virus. Three-week-old A129 mice (n=5) were immunized with 100 IFU WT or 10-del virus via the S.C. route. Viremia was quantified by immunostaining focus assay from day 2 to 6. On day 28 post-immunization, mouse sera were quantified for ZIKV neutralizing antibody titers. Also on day 28 post-immunization, the mice were challenged with $1\times10^6$ IFU of ZIKV (Puerto Rico strain PRVABC59) via the I.P. route. Viremias were quantified by immunostaining focus assay on day 2 post-challenge.

Immunization with 10 IFU 10-del virus. Three-week-old A129 mice (n=2 for each virus) were immunized with 10 IFU WT or 10-del ZIKV via the S.C. route. On day 28 post-immunization, mouse sera were quantified for ZIKV neutralizing antibody titers. On the same day, the mice were challenged with $1\times10^6$ IFU of ZIKV (Puerto Rico strain PRVABC59) via the I.P. route. On day 2 post-challenge, viremias were quantified using an immunostaining focus assay.

Results:

Since the 10-del virus produced the lowest viremia in mice (FIG. 5D), yet induced a neutralizing antibody response comparable to those of the WT and other mutants (FIG. 5E-5G), we prioritized this mutant for further characterization. At a dose of 100 IFU, 10-del virus-infected mice showed a delayed peak viremia that was >100-fold lower than that of the WT virus (FIG. 7A). Equivalent levels of pre-challenge neutralization titers were induced by the WT and 10-del viruses (FIG. 7B), leading to complete protection from viremia after challenge with $1\times10^6$ IFU of Puerto Rico ZIKV strain PRVABC59 (FIG. 7C). Furthermore, even when immunized at a dose of only 10 IFU, 10-del virus-infected mice generated a neutralization titer of $(9.7\pm6.8)\times10^3$, and were fully protected from viremia after challenge (FIG. 8).

It is noteworthy that mice immunized with different doses of 10-del mutant (10, $10^2$, and $10^4$ IFU) induced similar neutralization antibody titers and completely prevented viremia upon challenge (compare FIG. 5 and FIGS. 7 & 8).

Collectively, these results demonstrate that the 10-del virus is a potent vaccine candidate.

Example 6: Comparison of P0 and P5 10-Del Viruses

Materials and Methods:

Immunization with P0 or P5 10-del virus: Three-week-old A129 mice (n=5) were immunized with 100 IFU P0 or P5 10-del virus via the S.C. route. Viremia were quantified by immunostaining focus assay from day 4 to 6.

Pre-challenge neutralization antibody titers: On day 28 post-immunization, mouse sera were quantified for ZIKV neutralizing antibody titers.

Viremia after challenge with wild-type ZIKV: On day 28 post-immunization, the mice were challenged with $1\times10^6$ IFU of an epidemic strain of ZIKV (Puerto Rico strain PRVABC59) via the I.P. route. On day 2 post-challenge, viremias were quantified using an immunostaining focus assay.

Results:

Since P5 virus accumulated Vero cell-adaptive mutations (FIG. 4C), we compared the virulence and immunogenicity between the P0 and P5 10-del viruses in the A129 mice. After immunization with 100 IFU virus via the S.C. route, the P0 and P5 viruses generated comparable viremia and induced equivalent neutralization titers (FIGS. 11A & 11B). After challenging with $1\times10^6$ IFU of Puerto Rico strain PRVABC59 ZIKV via the I.P. route, no viremia was detected in the P0 or P5 virus-vaccinated mice; in contrast, robust viremia were detected in the sham group (FIG. 11C). These results indicate that the Vero cell-adaptive mutations recovered from the P5 virus do not significantly affect the virulence and immunogenicity of the 10-del virus.

Example 7: T Cell Responses in A129 Mice Immunized with 10-Del ZIKV

Materials and Methods:

Measuring T cell responses in A129 mice. A129 mice were infected with $1\times10^4$ IFU WT and 10-del viruses. On day 28 post-infection, mouse spleens were harvested. Splenocytes were counted, cultured ex vivo with WT ZIKV for 24 h, and stained for markers (IFN-γ, CD3, and CD4 or CD8). The T cells were gated based on staining for these markers, percentages of CD4$^+$IFN-γ$^+$ cells and CD8$^+$IFN-γ$^+$ cells were counted, and average total number of T cell subsets per spleen was recorded. Supernatants from the ex vivo culture were harvested on day 2 after WT ZIKV re-stimulation, and measured for IFN-γ and IL-2 production.

Bio-Plex immuneassay. Approximately $3\times10^5$ splenocytes were plated in 96-well plates and stimulated with $1.25\times10^4$ IFU ZIKV strain FSS13025 for 48 h. Culture supernatants were harvested and cytokine production were measured using a Bio-Plex Pro Mouse Cytokine Assay (Bio-Rad, Hercules, Calif.).

Intracellular cytokine staining (ICS). Approximately $2.5\times10^6$ splenocytes were stimulated with $1\times10^5$ IFU live ZIKV (strain FSS13025) for 24 h. During the final 5 h of stimulation, BD GolgiPlug (BD Bioscience) was added to block protein transport. Cells were stained with antibodies for CD3, CD4, or CD8; fixed in 2% paraformaldehyde, and permeabilized with 0.5% saponin before addition of anti-IFN-γ, or control rat IgG1 (e-Biosciences). Samples were processed with a C6 Flow Cytometer instrument. Dead cells were excluded on the basis of forward and side light scatter. Data were analyzed with a CFlow Plus Flow Cytometer (BD Biosciences).

Results:

We analyzed the T cell responses in A129 mice immunized with $1\times10^4$ IFU of WT and 10-del viruses. On day 28 post-immunization, ZIKV-specific T cells were re-stimulated with live WT virus in vitro, and analyzed using an intracellular cytokine staining (ICS) assay and a Bio-Plex immunoassay. The results showed that both WT and mutant virus-immune CD4$^+$ and CD8$^+$ T cells had higher IFN-γ responses than the mock-immunized group (FIGS. 9A & 9B). Furthermore, these immune T cells induced more IFN-γ (FIG. 9C) and IL2 (FIG. 9D) than the mock group; particularly, the 10-del mutant-immune T cells produced 4-fold higher IFN-γ than the WT virus-immune group. These results indicate that 10-del vaccine candidate induces a robust T cell response.

Example 8: Safety of 10-del Vaccine Candidate

Materials and Methods:

Organ virus titers. The heart, lung, liver, spleen, kidney, muscle, brain, testis, and eye were harvested on day 6 and 10 post-infection after $1\times10^4$ IFU of WT and 10-del virus vaccination via the S.C. route. Organ titrations were performed using a immunostaining focus assay as described above. In brief, 500 µl of DMEM with 2% FBS and penicillin/streptomycin along with a steel ball bearing were placed in a 2-ml Eppendorf tube. The organ (whole or part) was placed in the tube. Tubes were weighed, and organ weight was determined by subtracting the tube weight. Tissues were homogenized in a Qiagen TissueLyser II shaking at 26 p/second for 5 minutes. The homogenate was clarified by centrifugation for 5 min at 12,000 rpm and titrated on Vero monolayer using an immunostaining focus assay. The titer was then adjusted for volume and organ weight to report the organ loads as IFU/g (Reference 16).

Neurovirulence on newborn CD1 mice. Groups of 1-day-old outbred CD1 mice (n=7-10) were injected intracranially (I.C.) with WT or 10-del with serial tenfold dilutions from 10,000 IFU to 10 IFU. Mice were monitored daily for morbidity and mortality.

Experimental infection of mosquitoes with ZIKV. *Aedes aegypti* mosquitoes derived from a Galveston, Tex. colony were exposed for 45 min to blood-meals consisting of 1% (weight/volume) sucrose, 20% (vol/vol) FBS, 5 mM ATP, 33% (vol/vol) PBS-washed human blood cells (UTMB Blood Bank), and 33% (vol/vol) DMEM medium and combined with 1 ml virus offered in Hemotek 2-ml heated reservoirs (Discovery Workshops) covered with a mouse skin. Virus titers in the blood meals were $1\times10^6$ IFU/ml. Infectious blood meals were loaded on cartons containing Ae. aegypti. Fully engorged mosquitoes were incubated at 28° C., 80% relative humidity on a 12:12 h light:dark cycle with ad lib access to 10% sucrose solution for 7 days and harvested by freezing at −20° C. for 3 h. Whole mosquitoes were individually homogenized (Retsch MM300 homogenizer, Retsch Inc., Newton, Pa.) in DMEM with 20% FBS and 250 µg/ml amphotericin B and stored at −80° C. Samples were centrifuged for 10 min at 5,000 rpm, and 75 µl of each sample supernatant were inoculated into 96-well plates containing Vero cells at 37° C. and 5% $CO_2$ for 3 days, when they were fixed with a mixture of ice-cold acetone and methanol (1:1) solution and immunostained as described above. Infection was determined by detection of virus in the homogenized mosquito. The infection rate was recorded as the fraction of positive mosquitoes divided by the total number of engorged, incubated mosquitoes.

Testis and sperm count analyses: A129 mice were infected with $1\times10^4$ IFU of WT or 10-del mutant virus. A mock-infected group with PBS was included as a negative control. On day 16 p.i., the mice were euthanized and necropsied; epididymis and testes were harvested immediately as previously described (Reference 32). Briefly, the epididymis was placed into 1 ml of pre-warmed M2 media at 37° C. To release the sperm, the epididymis was cut lengthwise six times and incubated for 10 min, agitating every 2 min at 37° C. Following the incubation, the media containing the sperm was immediately diluted 1:50 into pre-warmed M2 media and counted on a hemocytometer. Motile sperms were categorized into progressive and non-progressive. Progressively motile sperms are described as continuous displacement of the head by flagellar movement. Non-progressively motile sperms are described as little to no displacement of the head by flagellar movement. In the non-motile sperms, no flagellar movement was observed.

Results:

Three sets of experiments were performed to analyze the safety of the 10-del vaccine candidate. First, we measured the viral loads in different organs after S.C. inoculation of A129 mice with $1\times10^4$ IFU of WT or 10-del viruses (FIG. 10A). On day 6 post-infection, the WT-infected mice had high viral loads in all organs tested, whereas the 10-del-infected mice had no virus in muscle or brain, and lower viral loads in heart, lung, liver, spleen, kidney, testes, and eye. On day 10 post-infection, WT virus-infected mice retained viral loads in kidney, brain, testis, and eye, among which testes had the highest mean titer; in contrast, no virus could be detected ($<10^2$ IFU/mL) in any organs from the 10-del-infected mice. Since ZIKV infection was reported to damage the testes in mice (References 17, 18), we examined the effect of immunization on the function of testes in the A129 mice. On day 16 post-immunization, similar weight and size of testes were recovered from the mock-, WT virus-, and 10-del mutant-infected mice. However, motile and total sperm counts were reduced in the WT virus-infected mice, whereas the 10-del virus-infected mice did not significantly compromise the sperm counts when compared with the mock group (FIG. 12).

Second, we examined the neurovirulence of 10-del virus through intracranial (IC.) injection of one-day-old CD1 mice (FIG. 10B). The newborn mice succumbed to WT virus infection in a dose-responsive manner; even a dose of 10 IFU resulted in 25% mortality. Remarkably, mice infected with 10-del virus did not show any apparent disease or death, even at a dose of $1\times10^4$ IFU. Finally, we determined if 10-del virus could infect *Aedes aegypti* mosquitoes, the main transmission vector of ZIKV in the Americas (References 19, 20). After exposure to artificial blood-meals containing $1\times10^6$ IFU/ml of WT or 10-del virus and incubation for 7 days, 56% of the engorged mosquitoes were infected by the WT virus, whereas no mosquitoes were infected by the 10-del mutant. Furthermore, intrathorax injection of 10-del virus to mosquitoes did not yield any infectious virus on day 7 after injection. Collectively, our results demonstrated that the 10-del virus significantly reduced or eliminated viral loads in mouse organs, decreased neurovirulence by >1,000-fold, and attenuated its ability to infect the principal urban mosquito vector, all suggestive of an excellent safety profile.

Our data indicate that the 3'UTR 10-del ZIKV is a promising live-attenuated vaccine candidate with a good balance between immunogenicity and safety. A single immunization elicited robust antibody and T cell responses, and significantly, unlike the subunit and inactivated ZIKV vaccines published to date, likely induces sterilizing immunity and providing complete protection against parental and epidemic strains of ZIKV. Vaccine-induced sterilizing immunity is likely critical for a successful ZIKV vaccine to prevent viremia and congenital abnormalities. The safety profile of this vaccine candidate is highlighted by the low viremia, little and transient viral loads in organs, and limited weight loss in the severe A129 mouse model, as well as a complete lack of morbidity and mortality in one-day-old mice after receiving an intracranial (IC.) injection. The latter safety result is impressive because I.C. inoculation with YFV 17D and JEV SA14-14-2 (two licensed live-attenuated flavivirus vaccines) results in lethal disease in one-day-old newborn mice (References 21, 22). Although potential homologous recombination between the WT and vaccine ZIKVs might pose a safety liability for the 10-del vaccine candidate, it should be noted that recombination events are rare and could not be detected in cell culture (References 23-27). Compared with the chimeric, live-attenuated ZIKV vaccine (e.g., YFV 17D expressing ZIKV prM-E or DENV expressing ZIKV prM-E (Reference 28)), our 3'UTR mutant vaccine has the advantage of retaining all ZIKV structural and nonstructural genes that may contribute to antiviral protection, as indicated from dengue vaccine studies (References 29, 30).

Compared with the chimeric, live-attenuated ZIKV vaccine (e.g., YFV 17D expressing ZIKV prM-E), our 3'UTR mutant vaccine has the advantage of retaining all ZIKV structural and nonstructural genes that may contribute to antiviral protection, as indicated from dengue vaccine studies (References 29, 30). Mechanistically, the 3'UTR mutant viruses appeared to be attenuated through decreased viral RNA replication and increased sensitivity to type-I interferon inhibition. The latter mechanism is in agreement with a recent report that genetic diversity at the 3'UTR of DENV contributes to epidemic potential (Reference 14). Taken together, our results indicate that the 3'UTR mutant ZIKV is an attractive vaccine candidate that should be advanced to non-human primates for further development. Additional in vivo experiments to characterize safety and efficacy of live attenuated ZIKV strains with 3'UTR deletions Materials and Methods:

Additional in vivo systems using the Materials and Methods and the examples which follow were also employed to characterize the safety and efficacy of vaccine candidates, including C57BL/6J mouse pregnancy, A129 mouse testis protection, viral loading in A129 mouse organ, CD-1 mouse neurovirulence, and rhesus macaque efficacy (see details below). The protocols for each of these experimental systems have been previously established (e.g., inoculum dose, infection route, challenge dose, and end-point measurement), and were not altered when evaluating these vaccine candidates. Therefore, different inoculum doses, challenge doses, and end-point measurements (e.g., qRT-PCR to measure viral RNA and focus forming assay to measure infection virus) were used in different in vivo systems according to the established protocols. The detailed information is described below and indicated in the Examples which follow.

Mouse Studies: All in vivo experiments using mice were performed in accordance with the recommendations in the Guide for the Care and Use of Laboratory Animals of the National Institutes of Health. The protocols were approved by the Institutional Animal Care and Use Committee (IACUC) at the Washington University School of Medicine (Assurance Number A3381-01) and the IACUC at the University of Texas Medical Branch (UTMB; Protocol Number 0209068B). Dissections and footpad injections were performed under anesthesia that was induced and maintained with ketamine hydrochloride and xylazine at the Washington University or isoflurane at UTMB. All efforts were made to minimize animal suffering. Rhesus macaque experiments were reviewed and approved by Vaccine Research Center Animal Care and Use Committee at the National Institute of Allergy and Infectious Diseases, the National Institutes of Health. The non-human primate experiments were performed in compliance with the pertinent regulations and policies from the National Institutes of Health.

Viruses and cells: The ZIKV Cambodian strain FSS13025 (GenBank number KU955593.1) was produced from an infectious cDNA clone (Reference 35). The ZIKV-3'UTR-Δ10-LAV and ZIKV-3'UTR-Δ20-LAV strains were generated as described. The Zika Puerto Rico strain PRVABC59 (GenBank number KU501215) and Dakar 41519 strain (GenBank number HQ234501.1) were obtained originally from Dr. Robert Tesh from the World Reference Center of Emerging Virus and Arboviruses (WRCEVA) at UTMB. The mouse-adapted ZIKV-Dakar 41519 strain was passaged twice in Rag1–/– mice (Jackson Laboratories) and described previously (Reference 29). Vero cells were purchased from the American Type Culture Collection (ATCC CCL-81; Bethesda, Md.), and maintained at 37° C. with 5% $CO_2$ in a high glucose Dulbecco modified Eagle medium (DMEM; Invitrogen, Carlsbad, Calif.) with 10% fetal bovine serum (FBS; HyClone Laboratories, Logan, Utah) and 1% penicillin/streptomycin (Invitrogen, Carlsbad, Calif.). All cell lines tested negative for mycoplasma.

Antibodies: The following antibodies were used in this study: anti-mouse IFN alpha/beta receptor 1 (Ifnar1) monoclonal antibody (clone MAR1-5A3; Leinco Technologies, Inc., St. Louis, Mo.); ZIKV-specific HMAF (hyper-immune ascites fluids; obtained from WRCEVA), anti-mouse IgG antibody labeled with horseradish peroxidase (KPL, Gaithersburg, Md.), and goat anti-mouse IgG conjugated with Alexa Fluor 488 (Thermo Fisher Scientific, Providence, R.I.).

A129 mouse experiments: A129 mice were bred in the animal facilities at UTMB. All mice were housed in pathogen-free mouse facilities. Three-week or 15-week old male A129 mice were infected with PBS (two sham groups), $10^4$ FFU of ZIKV-3'UTR-Δ10-LAV (A10), or $10^3$ FFU of ZIKV-3'UTR-Δ20-LAV (A20). Mice were anesthetized and bled via the retro orbital sinus (R.O.) for viremia testing. At day 28 post-immunization, mice were measured for neutralizing antibody titers using an mCherry ZIKV infection assay (Reference 36). On the same day, one sham group of PBS-immunized mice and Δ10- and Δ20-immunized mice were challenged with $10^6$ FFU of ZIKV PRVABC59. Another sham group of mice was used as an unchallenged negative control. At day 49 post-immunization, mice were euthanized and necropsied. Epididymis and testes were harvested immediately as previously described (Reference 32). Motile and non-motile sperms were counted manually on an emocytometer by microscopy. Total sperm counts equal to the sum of motile and non-motile sperms. For quantification of viral loads, testes were homogenized and infectious viral levels were measured by a focus forming assay or quantitative reverse transcriptase PCR (qRT-PCR) (Reference 36).

The qRT-PCT primer/probe set includes forward primer (1193F: 5'-CCGCTGCCCAACACAAG-3')(SEQ ID NO:10), reverse primer (1269R: 5'-CCACTAACGTTCTTTTGCAGACAT-3')(SEQ ID NO:11), and probe (5'-FAM/AGCCTACCT/ZEN/ TGACAAGCAATCAGACACTCAA/3IABkFQ-3')(SEQ ID NO:12). The probe contains a 5'-FAM reporter dye, 3' IBFQ quencher, and an internal ZEN quencher.

Mouse pregnancy experiments: C57BL/6J mice were bred and housed in pathogen-free mouse facilities at Washington University School of Medicine. One day prior to immunization, the eight-week old female C57BL/6J mice were dosed with 0.5 mg of anti-Ifnar1 antibody via an intraperitoneal route. Subsequently, mice were subcutaneously inoculated in the footpad with $10^5$ FFU of ZIKV-3'UTR-Δ10-LAV or PBS sham. Immunized wild-type (WT) C57BL/6 female mice were mated with naïve WT male mice. At embryonic day 5 (E5), pregnant dams were injected intraperitoneally with 2 mg of anti-Ifnar1 antibody. On E6, mice were inoculated subcutaneously with $10^5$ FFU of mouse-adapted ZIKV Dakar 41519 via footpad injection. All animals were sacrificed on E13 and analyzed for viral loads in placentas, fetuses, and maternal tissues. Briefly, maternal blood, organs from dams (brain and spleen) and fetuses (placenta and fetal head) were collected. Serum was prepared after coagulation and centrifugation. Organs were weighed and homogenized using a bead-beater apparatus (MagNA Lyser, Roche). Viral RNA was extracted from serum and tissue samples using the RNeasy Mini kit (Qiagen). The viral RNA levels were determined by TaqMan one-step qRT-PCR on an ABI 7500 Fast Instrument using standard cycling conditions. Viral burden is expressed on a log 10 scale as viral RNA equivalents per gram or per milliliter after comparison with a standard curve produced using serial 5-fold dilutions of ZIKV RNA from known quantities of infectious virus. The following primer/probe set was used for ZIKV qRT-PCR: forward primer (1183F: 5'-CCACCAATGTTCTCTTGCAGACATATTG-3')(SEQ ID NO:13), reverse primer (1268R: 5'-TTCGGACAGCCGTTGTCCAACACAAG-3')(SEQ ID NO:14), and probe (1213F: 5'-56-FAM/AGCCTACCT TGACAAGCAGTC/3IABkFQ-3')(SEQ ID NO:15). Wherever indicated, viral burden for some samples was determined by focus forming assay on Vero cells (Reference 28).

Quantification of viral load in organs from A129 mice: A129 mice were infected and organs were quantified for viral load using a focus forming assay (Reference 28). Viral RNA in testis also was quantified by qRT-PCR. Briefly, testes were harvested and placed in DMEM with beads for homogenization. After homogenization, the supernatant was used to extract viral RNA using RNeasy Mini kit (Qiagen). Extracted RNA was eluted in 40 μl RNase-free water. qRT-PCR assays were performed on the LightCycler® 480 System (Roche) following the manufacturer's protocol by using a 50-μl reaction of the QuantiTect Probe RT-PCR Kit (QIAGEN) and 10 μl RNA template. The viral load was calculated based on a standard curve produced using serial 10-fold dilutions of ZIKV RNA from known quantities of infectious virus. The qRT-PCT primer/probe set includes forward primer (1193F: 5'-CCGCTGCCCAACACAAG-3') (SEQ ID NO:16), reverse primer (1269R: 5'-CCACTAACGTTCTTTTGCAGACAT-3')(SEQ ID NO:17), and probe (5'-FAM/AGCCTACCT/ZEN/ TGACAAGCAATCAGACACTCAA/3IABkFQ-3')(SEQ ID NO:18). The probe contains a 5'-FAM reporter dye, 3' IBFQ quencher, and an internal ZEN quencher.

Vaccination of non-human primates: Rhesus macaque (*Macaca mulatta*) experiments were performed at Bioqual, Inc. (Rockville, Md.). All animal experiments were reviewed and approved by the Animal Care and Use Committee of the Vaccine Research Center, the National Institute of Allergy and Infectious Diseases, the National Institutes of Health. Animals were housed and cared in accordance with local, state, federal, and institutional policies in an American Association for Accreditation of Laboratory Animal Care-accredited facility at the Bioqual Inc. Rhesus macaques (3-4/group) were randomized by body weight, gender, and age, and subcutaneously administered with $10^3$ FFU of parental WT ZIKV strain FSS13025, ZIKV-3'UTR-Δ10-LAV, ZIKV-3'UTR-Δ20-LAV, or PBS sham at day 0. Blood was collected at day 2, 3, 4, 5, 7, and 10 for viremia testing and weekly for analysis of antibody responses by an mCherry ZIKV neutralization assay (References 36, 38). The immunized animals were subcutaneously challenged with $10^3$ FFU of ZIKV strain PRVABC59 at week 8. Blood samples were collected for determination of viral load at day 2, 3, 4, 5, 7, and 10 and neutralization antibody at week 2, 4, and 6 post-challenge.

Viremia from rhesus macaques was quantified by a qRT-PCR assay and focus forming assay as described in the proceeding section. For qRT-PCR quantification, viral RNA was extracted from rhesus serum using QIAamp Viral RNA Kits (QIAGEN) following the manufacture instruction. Extracted RNA was eluted in 40 l RNase-free water. qRT-PCR assay was performed as described above. In vitro transcribed full-length ZIKV RNA was used as a standard for qRT-PCR quantification. The primer/probe set is described in the proceeding section.

Neutralization assay and neurovirulence: All antibody neutralization titers were determined using an mCherry ZIKV as previously reported (Reference 36). The dilution folds that neutralized 50% of mCherry ZIKV infection (NT50) were presented. For measuring neurovirulence, 1-day-old outbred CD-1 mice (Charles River) were injected intracranially with indicated amounts of viruses. The infected mice were monitored for morbidity and mortality as reported previously (Reference 36).

Mosquito infection: For measuring mosquito infection, artificial blood-meal spiked with $10^6$ FFU/ml of indicated viruses was used to feed *Aedes aegypti* mosquitoes (derived from a Galveston, Tex.), and engorged mosquitoes were incubated at 28° C., 80% relative humidity on a 12:12 h light:dark cycle with ad libitum access to 10% sucrose. The infection rates were determined at day 7 post-feeding as reported previously (Reference 10).

Data analysis: All data from these experiments the results of which are described in the examples which follow and are contained in the figures referenced therein were analyzed with GraphPad Prism v7.02 software. Data are expressed as the mean±standard deviation (SD). Comparisons of groups were performed using Mann-Whitney test or one-way ANOVA with a multiple comparisons correction. A P value of <0.05 indicates statistically significant.

Example 9: Prevention of Vertical Transmission in Pregnant Mice

The live-attenuated vaccine candidate described herein which contains a 10-nucleotide deletion in the 3'UTR of ZIKV genome (ZIKV-3'UTR-Δ10-LAV) was tested for its ability to prevent in utero transmission. In these experiments we subcutaneously inoculated $10^5$ focus-forming units (FFU) of ZIKV-3'UTR-Δ10-LAV or PBS-sham into 8-week-old wild-type C57BL/6 female mice (FIG. 13A). Because mice are not a native host for ZIKV due in part to a species-dependent lack of antagonism of type I IFN signaling (References 39, 40), we administered 0.5 mg of anti-Ifnar1 blocking antibody to female mice one day prior to vaccination to facilitate transient replication of ZIKV-3'UTR-Δ10-LAV and to attempt to produce disease (Reference 41). At day 28 post-vaccination, the animals were phlebotomized and serum was analyzed for neutralizing antibody (FIG. 13B); all ZIKV-3'UTR-Δ10-LAV-immunized mice developed high neutralizing antibody titers of 18,900 5,900 (mean±standard deviation; n=13), whereas, as expected, the PBS-immunized animals did not develop detectable neutralizing antibodies (FIG. 13C). At day 35 post-vaccination, the immunized females were mated with 12-week-old wild-type (WT) C57BL/6 male mice and monitored for vaginal plugs (FIG. 13A). At embryo day 6 (E6), pregnant mice were challenged subcutaneously with $10^5$ FFU of a mouse-adapted, pathogenic ZIKV African strain Dakar 41519 (Reference 42); to facilitate ZIKV-Dakar dissemination to the maternal decidua and fetal placenta, the pregnant mice were administered 2 mg of anti-Ifnar1 antibody at E5, one day before the challenge. At E13, maternal and fetal organs were harvested and measured for viral load.

After a single immunization, ZIKV-3'UTR-Δ10-LAV reduced median viral loads in the maternal spleen and brain by ~49,000-fold and ~120-fold, respectively (FIG. 13D-E). Placentas and fetal heads from the vaccinated dams showed 138,000-fold and 260-fold decreases in viral RNA loads, respectively, when compared with the PBS-immunized dams (FIG. 13F-G). Notably, 21 of 30 (70%) placentas and 21 of 30 (70%) fetal heads from ZIKV-3'UTR-Δ10-LAV-immunized dams had viral RNA loads at or below the detection limit; no infectious virus was recovered by focus forming assay from the placentas or fetal heads from the vaccinated dams (FIG. 17A-B). In addition, the immune correlate between the $EC_{50}$ values and the levels of infectious viruses recovered in the placenta revealed an expected inverse relationship between neutralizing titers and levels of ZIKV particles in placenta (FIG. 17C). Collectively, the data suggest that ZIKV-3'UTR-Δ10-LAV protects maternal organs from infection, partially prevents viral transmission to the fetus during an early stage of pregnancy, and limits fetal replication.

Example 10: Protection of ZIKV-Induced Damages to Testes

We examined the ability of ZIKV-3'UTR-Δ10-LAV to prevent testis infection and injury in Ifnar1$^{-/-}$ A129 mice (FIG. 14A). Since male mice reach sexual maturity at 8-week-old, we tested the vaccine efficacy in two age groups of mice: 3-week-old young males and 15-week-old adult males. Three-week-old young A129 male mice were vaccinated with a single-dose of $10^4$ FFU of ZIKV-3'UTR-Δ10-LAV or PBS sham. The ZIKV-3'UTR-Δ10-LAV generated a peak viremia of $1.2±0.34×10^4$ FFU (n=6) at day 4 post-vaccination (FIG. 14B). At day 28 post-vaccination, ZIKV-3'UTR-Δ10-LAV had induced robust neutralizing antibody titers of 7,700±2,600 (n=6) (FIG. 14C). At the same day, the animals were challenged intraperitoneally with $10^6$ FFU of an epidemic ZIKV strain from Puerto Rico (PRVABC59). No viremia was detected from the ZIKV-3'UTR-Δ10-LAV-vaccinated mice after challenge, whereas the sham-vaccinated animals sustained a mean peak viremia of $7.1\ 5.9×10^6$ FFU/ml (n=6) at day 2 post-challenge (FIG. 14D). At day 21 post-challenge, viral burden in the testis of PBS-immunized mice reached $5.8±8.4×10^6$ FFU/g (n=6), whereas no infectious virus was detected in the testes of ZIKV-3'UTR-Δ10-LAV-immunized mice (FIG. 14E). Both total and motile sperm counts from the ZIKV-3'UTR-Δ10-LAV-immunized mice were equivalent to those from age-matched unvaccinated, unchallenged healthy male mice. In contrast, the PBS-immunized, ZIKV-challenged mice showed 85% and 90% reduction for total and motile sperm counts, respectively, at day 21 post-infection (FIGS. 14F&G). Consistent with these data, the testis weight and size from the PBS-immunized, ZIKV-challenged mice were reduced, whereas no such reduction was observed in the ZIKV-3'UTR-Δ10-LAV-immunized, ZIKV-challenged animals (FIGS. 14H&I).

In 15-week-old adult A129 male mice, vaccination with ZIKV-3'UTR-Δ10-LAV also protected against testis infection, injury, and oligospermia (FIG. 17A-G). However, challenge of the PBS-vaccinated adult males with ZIKV PRVABC59 did not reduce the testis weight and size (FIGS. 17H&I) as much as that observed in the corresponding sham-vaccinated, young males (FIGS. 17H&I), suggesting an age-dependent testis pathology. Collectively, the results indicate that a single-dose immunization of ZIKV-3'UTR-Δ10-LAV protects the testis from infection and injury in male mice.

Example 11: Efficacy in Non-Human Primates

To determine whether the efficacy in mice extends to non-human primates (NHPs), we evaluated the viremia, immunogenicity, and potency of ZIKV-3'UTR-Δ10-LAV in rhesus macaques (RM; FIG. 15A). First, we assessed the level of attenuation of ZIKV-3'UTR-Δ10-LAV in RM by comparing viremia to the parental WT virus. After subcutaneous inoculation with $10^3$ FFU, WT ZIKV (2010 Cambodian strain FSS 13025) produced high levels of viremia in each of the four inoculated RM, with a mean peak viremia of 9.6 and $28.8×10^4$ genome copies/ml at days 4 and 5 post-infection, respectively (FIG. 15B, top panel). In contrast, only one of the four ZIKV-3'UTR-Δ10-LAV-inoculated RM exhibited viremia, and this level was just above the limit of detection of our qRT-PCR assay (FIG. 15B, second panel); thus, ZIKV-3'UTR-Δ10-LAV is highly attenuated in RM.

We next evaluated the immunogenicity of ZIKV-3'UTR-Δ10-LAV by measuring neutralizing antibodies from serum at days 5-98 post-immunization. Neutralizing antibodies elicited by WT ZIKV were detectable at day 7-10, peaked at 1/1,000 to 1/10,000 at day 14, and plateaued thereafter (FIG. 15C, top panel). Compared with the WT ZIKV infection, ZIKV-3'UTR-Δ10-LAV-inoculated animals showed slightly delayed production and lower levels of neutralizing antibody, with titers of ~1/100 at days 21-56 (FIG. 15C, second panel). At day 56 post-immunization, all RM were challenged with $10^3$ FFU of the epidemic ZIKV strain PRVABC59. Notably, no viremia was detected upon challenge in any of the RM that were pre-infected with WT ZIKV or vaccinated with the ZIKV-3'UTR-Δ10-LAV (FIG. 15D, top two panels). As controls, two PBS-inoculated RM were challenged in parallel and high levels of viremia were measured (FIG. 15D bottom panel). In addition to analysis of viral RNA by qRT-PCR, we also performed focus forming assays to measure infectious virus; infectious ZIKV was detected only in naïve RM challenged with WT ZIKV (FIG. 19).

To examine whether the ZIKV challenge resulted in boosted immune responses, we measured neutralizing activity post-challenge. No increase in neutralizing activity was observed in the WT ZIKV-vaccinated RM after challenge (FIG. 15C, top panel), indicating that the initial infection likely conferred sterilizing immunity. In contrast, the neutralizing antibody titers rose after challenge from approximately 1/100 to 1/1,000-1/10,000 in the ZIKV-3'UTR-Δ10-

LAV-immunized animals (FIG. 15C, second panel), demonstrating an anamnestic response and suggesting a low level of infection after challenge that was not detectable by qRT-PCR of serum. As expected, the PBS-inoculated control RM increased their neutralizing titers to ~1/10,000 after challenge (FIG. 15C, bottom panel).

Since ZIKV-3'UTR-Δ10-LAV did not elicit sterilizing immunity in RM, we evaluated whether a second live-attenuated vaccine candidate ZIKV-3'UTR-Δ20-LAV (Reference 36), which contains a 20-nucleotide deletion in the 3'UTR, could induce a stronger immune response. ZIKV-3'UTR-Δ20-LAV was shown previously, and paradoxically, to be less attenuated than ZIKV-3'UTR-Δ10-LAV in A129 mice, most likely because it is less sensitive to type-I IFN inhibition compared to ZIKV-3'UTR-Δ10-LAV(Reference 36). After subcutaneous inoculation of $10^3$ FFU of ZIKV-3'UTR-Δ20-LAV, two of the three RM had low, but detectable viremia (FIG. 15B, third panel). The immunized animals rapidly produced neutralizing antibodies by day 10, with inhibitory titers plateauing at 1/1,000 to 1/10,000 by days 14-21 (FIG. 15C, third panel). After challenge with $10^3$ FFU of ZIKV PRVABC59 at day 56, viremia was not detected by qRT-PCR (FIG. 15D, third panel) and no rise in neutralizing antibody titers was observed (FIG. 15C, third panel) in the ZIKV-3'UTR-Δ20-LAV-immunized animals. Although low number of animals were used for each vaccine candidates, the results suggest that a single-dose vaccination of ZIKV-3'UTR-Δ20-LAV-induces sterilizing immunity in NHPs (i.e., no detectable viremia and no increase of neutralizing antibody titer after challenge).

We also evaluated another live-attenuated ZIKV vaccine candidate encoding an NS1 without glycosylation (ZIKV-NS1-LAV) in RM. ZIKV-NS1-LAV was recently shown to prevent in utero transmission in a mouse pregnancy model (Reference 43). After subcutaneous immunization of four RMs with $10^3$ FFU of ZIKV-NS1-LAV, none of the animals showed any detectable viral RNA (FIG. 15B, fourth panel). Back titering of the ZIKV-NS1-LAV inoculum using focus-forming assay confirmed the infectivity of viral stock with the expected infectious titer. Unexpectedly the immunization did not elicit any neutralizing activity (FIG. 15C, fourth panel). After challenge with $10^3$ FFU of ZIKV PRVABC59 at day 56, all four animals displayed robust viremia (FIG. 15D, fourth panel) and generated neutralizing antibody titers (FIG. 15C, fourth panel). These results indicate that ZIKV-NS1-LAV is incapable of replicating and triggering antibody responses in RM.

Example 12: Testis Protection and Safety Analysis of ZIKV-3'UTR-Δ20-LAV

Because of the highly desirable sterilizing immunity induced by ZIKV-3'UTR-Δ20-LAV in RM, we further tested its efficacy and safety. Similar to ZIKV-3'UTR-Δ10-LAV, immunization of male A129 mice with $10^3$ FFU of ZIKV-3'UTR-Δ20-LAV completely prevented viral infection and testis injury after challenge with ZIKV PRVABC59, as determined by a lack of detectable viremia post-challenge, the absence of oligospermia, and no decrease in testis weight and size (FIG. 20). Next, five sets of experiments were performed to characterize the safety of ZIKV-3'UTR-Δ20-LAV.

First, we measured the organ viral loads after subcutaneous inoculation of A129 mice with $10^3$ FFU of ZIKV-3'UTR-Δ20-LAV or parental WT ZIKV (FIG. 16A). At day 6 post-infection, WT ZIKV-infected mice exhibited high viral loads in all tested organs, whereas no virus was detected ($\leq 10^2$ FFU/ml) in liver or brain from the ZIKV-3'UTR-Δ20-LAV-infected mice, with other organs (except spleen) exhibiting lower levels of the vaccine virus than those of the WT-infected animals. At day 10 post-infection, WT ZIKV-infected mice retained viral loads in the heart, spleen, kidney, testis, eye, and brain, whereas no organs from the ZIKV-3'UTR-Δ20-LAV-infected mice had any detectable virus.

Second, we examined the potential adverse effect of ZIKV-3'UTR-Δ20-LAV on the testis in 3-week-old A129 mice. As expected, at day 21 post-infection, WT ZIKV infection reduced testis weight and size (FIG. 16A-C), lowered total and motile sperm counts (FIG. 16D-E), and resulted in viral RNA in the shrunken testis (FIG. 16F). In contrast, ZIKV-3'UTR-Δ20-LAV did not affect sperm counts or testis weight and size (FIG. 16B-E), with no detectable viral RNA in the testes (FIG. 16F).

Third, we evaluated the neurovirulence of ZIKV-3'UTR-Δ20-LAV through intracranial inoculation of 1-day-old CD-1 mice (FIG. 16G). As reported previously (Reference 36), neonates succumbed to WT ZIKV infection; even a dose of only 10 FFU resulted in 13% mortality (FIG. 16G). In contrast, no mortality was observed in mice that were inoculated with $10^3$ FFU of ZIKV-3'UTR-Δ20-LAV; however, infection with $10^4$ FFU of ZIKV-3'UTR-Δ20-LAV resulted in a mortality rate of 29%.

Fourth, we tested if the vaccine candidate could infect *Aedes aegypti* mosquitoes, the main vector of ZIKV(References 19, 20). After feeding on artificial blood-meals containing $10^6$ FFU/ml of ZIKV-3'UTR-Δ20-LAV or WT ZIKV, 50% of the engorged mosquitoes were infected by WT ZIKV, whereas no mosquitoes were infected by ZIKV-3'UTR-Δ20-LAV (FIG. 16H).

Finally, we tested the stability of ZIKV-3'UTR-Δ20-LAV in cell culture. After continuous culture of ZIKV-3'UTR-Δ20-LAV on Vero cells (an approved cell line for vaccine production (Reference 44) for five rounds, all recovered P5 viruses (derived from three independent experiments) retained the 20-nucleotide deletion. However, the P5 viruses accumulated additional mutations in the E- and NS1-encoding genes (FIG. 21), which may represent Vero-cell-adaptive mutation(s) or compensatory mutation(s) to 3'UTR deletion. Further passaging of the viruses to P10 did not change the 20-nucleotide deletion, indicating that the deletion is stable in cell culture. Moreover, we passaged ZIKV-3'UTR-Δ20-LAV in A129 mice for three rounds (3 days per round); all recovered viruses retained the 20-nucleotide deletion, further suggesting the stability of the mutant virus. Taken together, these results demonstrate an excellent safety profile of ZIKV-3'UTR-Δ20-LAV, including limited, transient viral loads in mouse organs, no adverse effect on testicular function, decreased neurovirulence, incompetency to infect mosquitoes, and good stability.

Conclusions

Herein we demonstrate that live-attenuated ZIKV vaccine candidates containing deletions in the 3' untranslated region of the ZIKV genome (ZIKV-3'UTR-LAV), i.e., 10 and 20 nucleotide deletions, prevent viral transmission during pregnancy and testis damage in mice, as well as infection of non-human primates. After a single-dose vaccination, pregnant mice challenged with ZIKV at embryonic day 6 (E6) and evaluated at E13 show markedly diminished levels of viral RNA in maternal, placental, and fetal tissues. Vaccinated male mice challenged with ZIKV are protected against testis infection, injury, and oligospermia. A single immunization of rhesus macaques elicited a rapid and robust antibody response, conferring complete protection upon challenge. Furthermore, the ZIKV-3'UTR-LAV vaccine candidates have a desirable safety profile. These results suggest that further development of ZIKV-3'UTR-LAV is warranted for humans.

Particularly our results showed that a single immunization of ZIKV-3'UTR-Δ10-LAV prevented maternal-to-fetal transmission early during pregnancy in C57BL/6 mice. Although no infectious challenge virus was detected, very low levels of viral RNA were recovered from ~30% of placenta and fetal heads from the vaccinated dams after challenge; these breakthrough viral RNAs might derive from stable antibody-virus complexes, which can last for several days in vivo (Reference 47).

Based on these results the clinical implications of such breakthrough non-infectious viral RNA will be determined in other species and in particular will be evaluated in non-human primates (NHPs) and if successful in humans. In male A129 mice, a single-dose immunization of either ZIKV-3'UTR-Δ10-LAV or ZIKV-3'UTR-Δ20-LAV prevented testis infection and injury after challenge, indicating an additional benefit of vaccination to protect the male reproductive system. Notably, unprotected young A129 mice (3- or 7-week-old) infected with ZIKV developed smaller testes, whereas adult mice (19-week-old when infected) did not, suggesting that ZIKV infection might cause more severe reproductive damage in younger males. As noted above the clinical relevance of this observation will be confirmed in NHPs and humans.

In NHPs, a single-dose vaccination with ZIKV-3'UTR-Δ10-LAV or ZIKV-3'UTR-Δ20-LAV induced sufficient immune responses to prevent viremia, with the ZIKV-3'UTR-Δ10-LAV eliciting greater immunogenicity, as reflected by its ability to induce sterilizing immunity against challenge. One limitation of the current non-human primate results is the low number of animals used for each vaccine candidates (n=3-4). ZIKV vaccine-induced sterilizing immunity might be critical for protection of congenital abnormalities in humans.

Live-attenuated vaccines generally have the advantage of single dose, rapid induction of durable immunity. Since ZIKV is endemic primarily in low income countries, a vaccine with single-dose efficacy is of practical importance, particularly when controlling an explosive outbreak or immunizing population in remote areas where multiple doses and periodic boosting will be challenging (Reference 45). Thus, live-attenuated vaccines may be useful for immunizing populations living in and traveling to ZIKV-endemic areas. Besides our ZIKV-3'UTR-LAV, a single-dose immunization with nucleoside-modified mRNA expressing ZIKV prM-E (50 µg) (Reference 46) or a recombinant rhesus adenovirus serotype 52 vector expressing ZIKV prM-E ($10^{11}$ viral particles) (Reference 8) was also shown to rapidly elicit antibody response and prevent viremia in NHPs; whether these two vaccines achieved sterilizing immunity was not determined. All other vaccine platforms, including inactivated vaccine and prM-E DNA vaccine, need two shots to elicit robust antibody response for viremia protection in NHPs (References 7, 8).

It is conceivable that in immunocompromised individuals and pregnant women, vaccination with live-attenuated virus may be contraindicated to avoid potential adverse risks. However, these individuals could be protected using inactivated, subunit, or gene-based replication-defective vaccines. Therefore, it is desirable that multiple vaccine platforms be developed in parallel with those described herein in order to provide complementary options for preventing and controlling ZIKV infection and disease.

Example 13: DNA Plasmid-Launched Wild-Type Zika Virus and Vaccines

In order to facilitate the development of vaccines for preventing and controlling ZIKV infection and disease the inventors have developed a DNA plasmid that can be directly transfected into cells to generate Zika virus (ZIKV). The new DNA-launched ZIKV full-length (FL) clone is assembled in the backbone of the pCC1 vector. Besides the pCC1 vector sequence, it contains an eukaryotic promoter CMV or SV40, the full genome of ZIKV strain FSS13025, HDVr sequence, and poly-A tail. The clones are named as CMV ZIKV FL and SV40 ZIKV FL depending on the types of promoters used to transcribe the viral RNA. DNA-launched ZIKV full-length clones used to construct live attenuated ZIKV vaccine candidates are listed in Appendix A.

As shown in FIG. 22, both pCC1-CMV ZIKV FL and pCC1-SV40 ZIKV FL can efficiently launch wild-type ZIKV by transfection of DNA plasmid into Vero cells. In the experiments 5 micrograms of indicated DNA plasmid was transfected into Vero cells through electroporation. Culture fluids were collected from day 1 to 5. Infectious viral titers were measured by plaque assay on Vero cells.

Using the DNA-launched ZIKV FL clones (SEQ ID NO:6 and 7), we made DNA-launched live attenuated ZIKV vaccine candidates. Specifically, we engineered the 3'UTR 10-del or 20-del mutations (References 19, 48) into the DNA-launched ZIKV FL clones, resulting in ZIKV Del 10 and ZIKV Del 20, respectively. Depending on the promoter types, these DNA vaccine candidates are named as CMV ZIKV Del 10, CMV ZIKV Del 20, SV40 ZIKV Del 10, and SV40 ZIKV Del 20. Detailed description of the sequences of these particular DNA vaccine candidates is summarized in Appendix B. As shown in FIG. 23, the four DNA-launched live-attenuated ZIKV vaccine plasmids can also produce robust levels of vaccines after transfecting the DNA into Vero cells.

Appendix A: ZIKV Full-Length Clones Used to Construct Live Attenuated ZIKV Vaccine Candidates 1. CMV ZIKV Full Length (FL) sequence: SEQ ID NO: 6 in Sequence Listing
2. SV40 ZIKV Full Length (FL) sequence: SEQ ID NO:7 in Sequence Listing Appendix B: Detailed Description of Sequences of Exemplary Live Attenuated ZIKV Vaccine Candidates CMV ZIKV Del 10: Consists of a deletion variant of SEQ ID NO: 6 wherein the sequence "CCAGAAGAGG" (SEQ ID NO: 8 in Sequence Listing) is deleted.

CMV ZIKV Del 20: Consists of a deletion variant of SEQ ID NO: 6 wherein the sequence "CTGTGGATCTCCAGAAGAGG" (SEQ ID NO: 9 in Sequence Listing) is deleted.

SV40 ZIKV Del 10: Consists of a deletion variant of SEQ ID NO: 7 wherein the sequence "CCAGAAGAGG" (SEQ ID NO: 8 in Sequence Listing) is deleted.

SV40 ZIKV Del 10: Consists of a deletion variant of SEQ ID NO: 7 wherein the sequence "CTGTGGATCTCCAGAAGAGG" (SEQ ID NO: 9 in Sequence Listing) is deleted.

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

SEQUENCES

3'UTR-WT

SEQ ID NO: 1

GCACCAATCTTAGTGTTGTCAGGCCTGCTAGTCAGCCACAGCTTGGGGAAAGCTG

TGCAGCCTGTGACCCCCCCAGGAGAAGCTGGGAAACCAAGCCCATAGTCAGGCC

GAGAACGCCATGGCACGGAAGAAGCCATGCTGCCTGTGAGCCCCTCAGAGGACA

CTGAGTCAAAAAACCCCACGCGCTTGGAGGCGCAGGATGGGAAAAGAAGGTGG

CGACCTTCCCCACCCTTTAATCTGGGGCCTGAACTGGAGATCAGCTGTGGATCTC

CAGAAGAGGGACTAGTGGTTAGAGGAGACCCCCCGGAAAACGCAAAACAGCAT

ATTGACGCTGGGAAAGACCAGAGACTCCATGAGTTTCCACCACGCTGGCCGCCA

GGCACAGATCGCCGAATAGCGGCGGCCGGTGTGGGGAAATCCATGGTTTCT

3'UTR-10-del

SEQ ID NO: 2

GCACCAATCTTAGTGTTGTCAGGCCTGCTAGTCAGCCACAGCTTGGGGAAAGCTG

TGCAGCCTGTGACCCCCCCAGGAGAAGCTGGGAAACCAAGCCCATAGTCAGGCC

GAGAACGCCATGGCACGGAAGAAGCCATGCTGCCTGTGAGCCCCTCAGAGGACA

CTGAGTCAAAAAACCCCACGCGCTTGGAGGCGCAGGATGGGAAAAGAAGGTGG

CGACCTTCCCCACCCTTTAATCTGGGGCCTGAACTGGAGATCAGCTGTGGATCTG

ACTAGTGGTTAGAGGAGACCCCCCGGAAAACGCAAAACAGCATATTGACGCTGG

GAAAGACCAGAGACTCCATGAGTTTCCACCACGCTGGCCGCCAGGCACAGATCG

CCGAATAGCGGCGGCCGGTGTGGGGAAATCCATGGTTTCT

3'UTR-20-del

SEQ ID NO: 3

GCACCAATCTTAGTGTTGTCAGGCCTGCTAGTCAGCCACAGCTTGGGGAAAGCTG

TGCAGCCTGTGACCCCCCCAGGAGAAGCTGGGAAACCAAGCCCATAGTCAGGCC

GAGAACGCCATGGCACGGAAGAAGCCATGCTGCCTGTGAGCCCCTCAGAGGACA

CTGAGTCAAAAAACCCCACGCGCTTGGAGGCGCAGGATGGGAAAAGAAGGTGG

CGACCTTCCCCACCCTTTAATCTGGGGCCTGAACTGGAGATCAGGACTAGTGGTT

AGAGGAGACCCCCCGGAAAACGCAAAACAGCATATTGACGCTGGGAAAGACCA

GAGACTCCATGAGTTTCCACCACGCTGGCCGCCAGGCACAGATCGCCGAATAGC

GGCGGCCGGTGTGGGGAAATCCATGGTTTCT

3'UTR-30-del-a

SEQ ID NO: 4

GCACCAATCTTAGTGTTGTCAGGCCTGCTAGTCAGCCACAGCTTGGGGAAAGCTG

TGCAGCCTGTGACCCCCCCAGGAGAAGCTGGGAAACCAAGCCCATAGTCAGGCC

GAGAACGCCATGGCACGGAAGAAGCCATGCTGCCTGTGAGCCCCTCAGAGGACA

CTGAGTCAAAAAACCCCACGCGCTTGGAGGCGCAGGATGGGAAAAGAAGGTGG

CGACCTTCCCCACCCTTTAATCTGGGGCCTGAACGACTAGTGGTTAGAGGAGACC

CCCGGAAAACGCAAAACAGCATATTGACGCTGGGAAAGACCAGAGACTCCATG

AGTTTCCACCACGCTGGCCGCCAGGCACAGATCGCCGAATAGCGGCGGCCGGTG

TGGGGAAATCCATGGTTTCT

3'UTR-30-del-b

SEQ ID NO: 5

GCACCAATCTTAGTGTTGTCAGGCCTGCTAGTCAGCCACAGCTTGGGGAAAGCTG

TGCAGCCTGTGACCCCCCCAGGAGAAGCTGGGAAACCAAGCCCATAGTCAGGCC

GAGAACGCCATGGCACGGAAGAAGCCATGCTGCCTGTGAGCCCCTCAGAGGACA

-continued

CTGAGTCAAAAAACCCCACGCGCTTGGAGGCGCAGGATGGGAAAAGAAGGTGG

CGACCTTCCCCACCCTTTAATCTGGGGCCTGAACTGGAGATCAGCTGTGGAGACC

CCCCGGAAAACGCAAAACAGCATATTGACGCTGGGAAAGACCAGAGACTCCATG

AGTTTCCACCACGCTGGCCGCCAGGCACAGATCGCCGAATAGCGGCGGCCGGTG

TGGGGAAATCCATGGTTTCT

CMV ZIKV FL sequence:

SEQ ID NO: 6

AGTTGTTGATCTGTGTGAATCAGACTGCGACAGTTCGAGTTTGAAGCGAAAGCTA

GCAACAGTATCAACAGGTTTTATTTTGGATTTGGAAACGAGAGTTTCTGGTCATG

AAAAACCCAAAGAAGAAATCCGGAGGATTCCGGATTGTCAATATGCTAAAACGC

GGAGTAGCCCGTGTGAGCCCCTTTGGGGGCTTGAAGAGGCTGCCAGCCGGACTT

CTGCTGGGTCATGGGCCCATCAGGATGGTCTTGGCGATTCTAGCCTTTTTGAGAT

TCACGGCAATCAAGCCATCACTGGGTCTCATCAATAGATGGGGTTCAGTGGGGA

AAAAGAGGCTATGGAAATAATAAAGAAGTTTAAGAAAGATCTGGCTGCCATGC

TGAGAATAATCAATGCTAGGAAGGAGAAGAAGAGACGAGGCACAGATACTAGT

GTCGGAATTGTTGGCCTCCTGCTGACCACAGCCATGGCAGTGGAGGTCACTAGAC

GTGGGAATGCATACTATATGTACTTGGACAGAAGCGATGCTGGGGAGGCCATAT

CTTTTCCAACCACAATGGGGATGAATAAGTGTTATATACAGATCATGGATCTTGG

ACACATGTGTGATGCCACCATGAGCTATGAATGCCCTATGCTGGATGAGGGGGT

AGAACCAGATGACGTCGATTGTTGGTGCAACACGACGTCAACTTGGGTTGTGTAC

GGAACCTGCCACCACAAAAAAGGTGAAGCACGGAGATCTAGAAGAGCTGTGAC

GCTCCCCTCCCATTCCACTAGGAAGCTGCAAACGCGGtCGCAGACCTGGTTGGAA

TCAAGAGAATACACAAAGCACCTGATTAGAGTCGAAAATTGGATATTCAGGAAC

CCTGGCTTCGCGTTAGCAGCAGCTGCCATCGCTTGGCTTTTGGGAAGCTCAACGA

GCCAAAAAGTCATATACTTGGTCATGATACTGCTGATTGCCCCGGCATACAGCAT

CAGGTGCATAGGAGTCAGCAATAGGGACTTTGTGGAAGGTATGTCAGGTGGGAC

TTGGGTTGATGTTGTCTTGGAACATGGAGGTTGTGTTACCGTAATGGCACAGGAC

AAACCGACTGTCGACATAGAGCTGGTTACAACAACAGTCAGCAACATGGCGGAG

GTAAGATCCTACTGCTATGAGGCATCAATATCGGACATGGCTTCGGACAGCCGCT

GCCCAACACAAGGTGAAGCCTACCTTGACAAGCAATCAGACACTCAATATGTCT

GCAAAAGAACGTTAGTGGACAGAGGCTGGGGAAATGGATGTGGACTTTTTGGCA

AAGGGAGCCTGGTGACATGCGCTAAGTTTGCTTGCTCTAAGAAAATGACCGGGA

AGAGCATCCAGCCAGAGAATCTGGAGTACCGGATAATGCTGTCAGTTCATGGCT

CCCAGCACAGTGGGATGATCGTTAATGATACAGGACATGAAACTGATGAGAATA

GAGCGAAGGTTGAGATAACGCCCAATTCACCAAGAGCCGAAGCCACCCTGGGGG

GTTTTGGAAGCCTAGGACTTGATTGTGAACCGAGGACAGGCCTTGACTTTTCAGA

TTTGTATTACTTGACTATGAATAACAAGCACTGGTTGGTTCACAAGGAGTGGTTC

CACGACATTCCATTACCTTGGCAcGCTGGGGCAGACACCGGAACTCCACACTGGA

ACAACAAAGAAGCACTGGTAGAGTTCAAGGACGCACATGCCAAAAGGCAGACT

GTCGTGGTTCTAGGGAGTCAAGAAGGAGCAGTTCACACGGCCCTTGCTGGAGCT

CTGGAGGCTGAGATGGATGGTGCAAAGGGAAGGCTGTCCTCTGGCCACTTGAAA

TGTCGCCTGAAAATGGAcAAACTTAGATTGAAGGGCGTGTCATACTCCTTGTGTA

-continued

```
CCGCAGCGTTCACATTCACTAAGATCCCGGCTGAAACACTGCACGGGACAGTCA
CAGTGGAGGTACAGTACGCAGGGACAGATGGACCTTGCAAGGTTCCAGCTCAGA
TGGCGGTGGACATGCAAACTCTGACCCCAGTTGGGAGGTTGATAACCGCTAACC
CTGTAATCACTGAAAGCACTGAGAACTCCAAGATGATGCTGGAACTGGATCCAC
CATTTGGGGACTCTTACATTGTCATAGGAGTCGGGGAAAAGAAGATCACCCACC
ACTGGCACAGGAGTGGCAGCACCATTGGAAAAGCATTTGAAGCCACTGTGAGAG
GTGCCAAGAGAATGGCAGTCTTGGGAGACACAGCCTGGGACTTTGGATCAGTTG
GGGGTGCTCTCAACTCACTGGGCAAGGGCATCCATCAAATTTTTGGAGCAGCTTT
CAAATCATTGTTTGGAGGAATGTCCTGGTTCTCACAAATTCTCATTGGAACGTTG
CTGGTGTGGTTGGGTCTGAATACAAAGAATGGATCTATTTCCCTTATGTGCTTGG
CCTTAGGGGAGTGTTGATCTTCTTATCCACAGCCGTCTCTGCTGATGTGGGGTG
CTCGGTGGACTTCTCAAAGAAGGAAACGAGATGCGGTACAGGGGTGTTCGTCTA
TAACGACGTTGAAGCTTGGAGGGACAGGTACAAGTACCATCCTGACTCCCCTCGT
AGATTGGCAGCAGCAGTCAAGCAAGCCTGGGAAGATGGGATCTGTGGGATCTCC
TCTGTTTCAAGAATGGAAAACATCATGTGGAGATCAGTAGAAGGGGAGCTCAAC
GCAATCCTGGAAGAGAATGGAGTTCAACTGACGGTCGTTGTGGGATCTGTAAAA
AACCCCATGTGGAGAGGTCCACAGAGATTGCCCGTGCCTGTGAACGAGCTGCCC
CATGGCTGGAAGGCTTGGGGGAAATCGTACTTCGTCAGGGCAGCAAAGACAAAT
AACAGCTTTGTCGTGGATGGTGACACACTGAAGGAATGCCCACTCAAACATAGA
GCATGGAACAGCTTTCTTGTGGAGGATCATGGGTTCGGGGTATTTCACACTAGTG
TCTGGCTCAAGGTTAGAGAAGATTATTCACTCGAGTGTGATCCAGCCGTCATTGG
AACAGCCGCTAAGGGAAAGGAGGCTGTGCACAGTGATCTAGGCTACTGGATTGA
GAGTGAGAAGAACGACACATGGAGGCTGAAGAGGGCCCACCTGATCGAGATGA
AAACATGTGAATGGCCAAAGTCCCACACATTGTGGACAGATGGAATAGAAGAA
GTGATCTGATCATACCCAAGTCTTTAGCTGGGCCACTCAGCCATCACAACACCAG
AGAGGGCTACAGGACCCAAATGAAAGGGCCATGGCATAGTGAAGAGCTTGAAAT
TCGGTTTGAGGAATGCCCAGGCACTAAGGTCCACGTGGAGGAAACATGTGGAAC
AAGAGGACCATCTCTGAGATCAACCACTGCAAGCGGAAGGGTGATCGAGGAATG
GTGCTGCAGGGAGTGCACAATGCCCCACTGTCGTTCCGGGCTAAAGATGGTTGT
TGGTATGGAATGGAGATAAGGCCCAGGAAAGAACCAGAAAGTAACTTAGTAAG
GTCAATGGTGACTGCAGGATCAACTGATCACATGGATCACTTCTCCCTTGGAGTG
CTTGTGATTCTGCTCATGGTACAGGAAGGGCTAAAGAAGAGAATGACCACAAAG
ATCATCATAAGCACATCAATGGCAGTGCTGGTAGCTATGATCCTGGGAGGATTTT
CAATGAGTGACCTGGCTAAGCTTGCAATTTTGATGGGTGCCACCTTCGCGGAAAT
GAACACTGGAGGAGATGTTGCTCATCTGGCGCTGATAGCGGCATTCAAAGTCAG
ACCTGCGTTGCTGGTATCTTTCATTTTCAGAGCTAATTGGACACCCCGTGAGAGC
ATGCTGCTGGCCTTGGCCTCGTGTCTTCTGCAAACTGCGATCTCCGCCTTGGAAG
GCGACCTGATGGTTCCCATCAATGGTTTTGCTTTGGCCTGGTTGGCAATACGAGC
GATGGTTGTTCCACGCACTGACAACATCACCTTGGCAATCCTGGCTGCTCTGACA
CCACTGGCCCGGGGCACACTGCTTGTGGCGTGGAGAGCAGGCCTTGCTACTTGCG
```

-continued

```
GGGGGTTCATGCTCCTTTCTCTGAAGGGGAAAGGCAGTGTGAAGAAGAACTTAC
CATTTGTCATGGCCCTGGGACTAACCGCTGTGAGGCTGGTCGACCCCATCAACGT
GGTGGGACTGCTGTTGCTCACAAGGAGTGGGAAGCGGAGCTGGCCCCCTAGTGA
AGTACTCACAGCTGTTGGCCTGATATGCGCATTGGCTGGAGGGTTCGCCAAGGCG
GATATAGAGATGGCTGGGCCCATGGCCGCGGTCGGTCTGCTAATTGTCAGTTACG
TGGTCTCAGGAAAGAGTGTGGACATGTACATTGAAAGAGCAGGTGACATCACAT
GGGAAAAAGATGCGGAAGTCACTGGAAACAGTCCCCGGCTCGATGTGGCACTAG
ATGAGAGTGGTGATTTCTCCCTAGTGGAGGATGATGGTCCCCCCATGAGAGAGAT
CATACTCAAAGTGGTCCTGATGGCCATCTGTGGCATGAACCCAATAGCCATACCC
TTTGCAGCTGGAGCGTGGTACGTGTATGTGAAGACTGGAAAAAGGAGTGGTGCT
CTATGGGATGTGCCTGCTCCCAAGGAAGTAAAAAGGGGGAGACCACAGATGGA
GTGTACAGAGTAATGACTCGTAGACTGCTAGGTTCAACACAAGTTGGAGTGGGA
GTCATGCAAGAGGGGGTCTTCCACACTATGTGGCACGTCACAAAAGGATCCGCG
CTGAGAAGCGGTGAAGGGAGACTTGATCCATACTGGGGAGATGTCAAGCAGGAT
CTGGTGTCATACTGTGGTCCATGGAAGCTAGATGCCGCCTGGGACGGGCACAGC
GAGGTGCAGCTCTTGGCCGTGCCCCCCGGAGAGAGAGCGAGGAACATCCAGACT
CTGCCCGGAATATTTAAGACAAAGGATGGGGACATTGGAGCAGTTGCGCTGGAC
TACCCAGCAGGTACCTCAGGATCTCCAATCCTAGATAAGTGTGGGAGAGTGATA
GGACTCTATGGTAATGGGGTCGTGATCAAAAATGGGAGTTACGTTAGTGCCATCA
CCCAAGGGAGGAGGGAGGAAGAGACTCCTGTTGAGTGCTTCGAGCCTTCGATGC
TGAAGAAGAAGCAGCTAACTGTCTTAGACTTGCATCCTGGAGCTGGGAAAACCA
GGAGAGTTCTTCCTGAAATAGTCCGTGAAGCCATAAAAACAAGACTCCGCACTG
TGATCTTAGCTCCAACCAGGGTTGTCGCTGCTGAAATGGAGGAAGCCCTTAGAGG
GCTTCCAGTGCGTTATATGACAACAGCAGTCAATGTCACCCATTCTGGGACAGAA
ATCGTTGACTTAATGTGCCATGCCACCTTCACTTCACGTCTACTACAGCCAATCA
GAGTCCCCAACTATAATCTGTATATTATGGATGAGGCCCACTTCACAGATCCCTC
AAGTATAGCAGCAAGAGGATACATTTCAACAAGGGTTGAGATGGGCGAGGCGGC
TGCCATCTTCATGACTGCCACGCCACCAGGAACCCGTGACGCATTCCCGGACTCC
AACTCACCAATTATGGACACCGAAGTGGAAGTCCCAGAGAGAGCCTGGAGCTCA
GGCTTTGATTGGGTGACGGATCATTCTGGAAAAACAGTTTGGTTTGTTCCAAGCG
TGAGGAATGGCAATGAGATCGCAGCTTGTCTGACAAAGGCTGGAAAACGGGTCA
TACAGCTCAGCAGAAAGACTTTTGAGACAGAGTTCCAGAAAACAAAACATCAAG
AGTGGGACTTCGTCGTGACAACTGACATTTCAGAGATGGGCGCCAACTTTAAAGC
TGACCGTGTCATAGATTCCAGGAGATGCCTAAAGCCGGTCATACTTGATGGCGAG
AGAGTCATTCTGGCTGGACCCATGCCTGTCACACATGCCAGCGCTGCCCAGAGG
AGGGGGCGCATAGGCAGGAACCCCAACAAACCTGGAGATGAGTATCTGTATGGA
GGTGGGTGCGCAGAGACTGATGAAGACCATGCACACTGGCTTGAAGCAAGAATG
CTTCTTGACAACATTTACCTCCAAGATGGCCTCATAGCCTCGCTCTATCGACCTGA
GGCCGACAAAGTAGCAGCTATTGAGGGAGAGTTCAAGCTTAGGACGGAGCAAAG
GAAGACCTTTGTGGAACTCATGAAAAGAGGAGATCTTCCTGTTTGGCTGGCCTAT
CAGGTTGCATCTGCCGGAATAACCTACACAGATAGAAGATGGTGCTTTGATGGC
```

```
ACGACCAACAACACCATAATGGAAGACAGTGTGCCGGCAGAGGTGTGGACCAGA

TACGGAGAGAAAAGAGTGCTCAAACCGAGGTGGATGGACGCCAGAGTTTGTTCA

GATCATGCGGCCCTGAAGTCATTCAAAGAGTTTGCCGCTGGGAAAAGAGGAGCG

GCCTTTGGAGTGATGGAAGCCCTGGGAACACTGCCAGGACATATGACAGAGAGA

TTCCAGGAGGCCATTGACAACCTCGCTGTGCTCATGCGGGCAGAGACTGGAAGC

AGGCCCTACAAAGCCGCGGCGGCCCAATTACCGGAGACCCTAGAGACTATCATG

CTTTTGGGGTTGCTGGGAACAGTCTCGCTGGGAATCTTTTTCGTCTTGATGCGGA

ACAAGGGCATAGGGAAGATGGGCTTTGGAATGGTGACTCTTGGGGCCAGCGCAT

GGCTTATGTGGCTCTCGGAAATTGAGCCAGCCAGAATTGCATGTGTCCTCATTGT

TGTGTTCCTATTGCTGGTGGTGCTCATACCTGAGCCAGAAAAGCAAAGATCTCCC

CAGGACAACCAAATGGCAATCATCATCATGGTAGCAGTGGGTCTTCTGGGCTTGA

TTACCGCCAATGAACTCGGATGGTTGGAGAGAACAAAGAGTGACCTAAGCCATC

TAATGGGAAGGAGAGAGGAGGGGGCAACTATAGGATTCTCAATGGACATTGACC

TGCGGCCAGCCTCAGCTTGGGCTATCTATGCTGCTCTGACAACTTTCATTACCCCA

GCCGTCCAACATGCAGTGACCACTTCATACAACAACTACTCCTTAATGGCGATGG

CCACGCAAGCTGGAGTGTTGTTCGGTATGGGTAAAGGGATGCCATTCTATGCATG

GGACTTTGGAGTCCCGCTGCTAATGATAGGTTGCTACTCACAATTAACACCCCTG

ACCCTAATAGTGGCCATCATTTTGCTCGTGGCGCACTACATGTACTTGATCCCAG

GGCTGCAGGCAGCAGCTGCGCGTGCTGCCCAGAAGAGAACGGCAGCTGGCATCA

TGAAGAACCCTGTTGTGGATGGAATAGTGGTGACTGACATTGACACAATGACAA

TTGACCCCCAAGTGGAGAAAAAGATGGGACAGGTGCTACTCATAGCAGTAGCTG

TCTCCAGCGCCATACTGTCGCGGACCGCCTGGGGGTGGGGTGAGGCTGGGGCCC

TGATCACAGCTGCAACTTCCACTTTGTGGGAGGGCTCTCCGAACAAGTACTGGAA

CTCCTCCACAGCCACCTCACTGTGTAACATTTTTAGGGGAAGCTACTTGGCTGGA

GCTTCTCTAATCTACACAGTAACAAGAAACGCTGGCTTGGTCAAGAGACGTGGG

GGTGGAACGGGAGAGACCCTGGGAGAGAAATGGAAGGCCCGCCTGAACCAGAT

GTCGGCCCTGGAGTTCTACTCCTACAAAAAGTCAGGCATCACCGAGGTGTGCAG

AGAAGAGGCCCGCCGCGCCCTCAAGGACGGTGTGGCAACGGGAGGCCACGCTGT

GTCCCGAGGAAGTGCAAAGCTGAGATGGTTGGTGGAGAGGGGATACCTGCAGCC

CTATGGAAAGGTCATTGATCTTGGATGTGGCAGAGGGGGCTGGAGTTACTATGCC

GCCACCATCCGCAAAGTTCAAGAAGTGAAAGGATACACAAAAGGAGGCCCTGGT

CATGAAGAACCCATGTTGGTGCAAAGCTATGGGTGGAACATAGTCCGTCTTAAG

AGTGGGGTGGACGTCTTTCATATGGCGGCTGAGCCGTGTGACACGTTGCTGTGTG

ATATAGGTGAGTCATCATCTAGTCCTGAAGTGGAAGAAGCACGGACGCTCAGAG

TCCTCTCCATGGTGGGGATTGGCTTGAAAAAAGACCAGGAGCCTTTTGTATAAA

AGTGTTGTGCCCATACACCAGCACTATGATGGAAACCCTGGAGCGACTGCAGCG

TAGGTATGGGGAGGACTGGTCAGAGTGCCACTCTCCCGCAACTCTACACATGA

GATGTACTGGGTCTCTGGAGCGAAAAGCAACACCATAAAAAGTGTGTCCACCAC

GAGCCAGCTCCTTTTGGGGCGCATGGACGGGCCCAGGAGGCCAGTGAAATATGA

AGAGGATGTGAATCTCGGCTCTGGCACGCGGGCTGTGGTAAGCTGCGCTGAAGC
```

-continued
```
TCCCAACATGAAGATCATTGGTAACCGCATTGAGAGGATCCGCAGTGAGCACGC

GGAAACGTGGTTCTTTGACGAGAACCACCCATATAGGACATGGGCTTACCATGG

AAGCTACGAGGCCCCCACACAAGGGTCAGCGTCCTCTCTAATAAACGGGGTTGT

CAGGCTCCTGTCAAAACCCTGGGATGTGGTGACTGGAGTCACAGGAATAGCCAT

GACCGACACCACACCGTATGGTCAGCAAAGAGTTTTCAAGGAAAAAGTGGACAC

TAGGGTGCCAGACCCCCAAGAAGGCACTCGTCAGGTTATGAGCATGGTCTCTTCC

TGGTTGTGGAAAGAGTTAGGCAAACACAAACGGCCACGAGTCTGTACCAAAGAA

GAGTTCATCAACAAGGTTCGTAGCAACGCAGCATTAGGGGCAATATTTGAAGAG

GAAAAAGAGTGGAAGACTGCAGTGGAAGCTGTGAACGATCCAAGGTTCTGGGCT

CTAGTGGACAAGGAAAGAGAGCACCACCTGAGAGGAGAGTGCCAGAGCTGTGT

GTACAACATGATGGGAAAAAGAGAAAAGAAACAAGGGGAATTTGGAAAGGCCA

AGGGCAGCCGCGCCATCTGGTACATGTGGCTAGGGGCTAGATTTCTAGAGTTCGA

AGCCCTTGGATTCTTGAACGAGGATCACTGGATGGGGAGAGAGAATTCAGGAGG

TGGTGTTGAAGGGCTAGGATTACAAAGACTCGGATATGTCTTAGAAGAGATGAG

TCGCATACCAGGAGGAAGGATGTATGCAGATGATACTGCTGGCTGGGACACCCG

CATCAGCAGGTTTGATCTGGAGAATGAAGCTCTAATCACCAACCAAATGGAGAA

AGGGCACAGGGCCTTGGCATTGGCCATAATCAAGTACACATACCAAAACAAAGT

GGTAAAGGTCCTTAGACCAGCTGAAAAAGGGAAGACAGTTATGGACATTATTTC

AAGACAAGACCAAAGGGGGAGCGGACAAGTTGTCACTTACGCTCTTAATACATT

TACCAACCTAGTGGTGCAGCTCATTCGGAATATGGAGGCTGAGGAAGTTCTAGA

GATGCAAGACTTGTGGCTGCTGCGGAGGTCAGAGAAAGTGACCAACTGGTTGCA

GAGCAATGGATGGGATAGGCTCAAACGAATGGCAGTCAGTGGAGATGATTGCGT

TGTGAAACCAATTGATGATAGGTTTGCACATGCTCTCAGGTTCTTGAATGATATG

GGAAAAGTTAGGAAGGACACACAAGAGTGGAAGCCCTCAACTGGATGGGACAA

CTGGGAAGAAGTTCCGTTTTGCTCCCACCACTTCAACAAGCTCCATCTCAAGGAC

GGGAGGTCCATTGTGGTTCCCTGCCGCCACCAAGATGAACTGATTGGCCGAGCTC

GCGTCTCACCGGGGGCGGGATGGAGCATCCGGGAGACTGCTTGCCTAGCAAAAT

CATATGCGCAAATGTGGCAGCTCCTTTATTTCCACAGAAGGGACCTCCGACTGAT

GGCCAATGCCATTTGTTCATCTGTGCCAGTTGACTGGGTTCCAACTGGGAGAACT

ACCTGGTCAATCCATGGAAAGGGAGAATGGATGACCACTGAAGACATGCTTGTG

GTGTGGAACAGAGTGTGGATTGAGGAGAACGACCACATGGAAGACAAGACCCC

AGTTACGAAATGGACAGACATTCCCTATTTGGGAAAAAGGGAAGACTTGTGGTG

TGGGTCTCTCATAGGGCACAGACCGCGCACCACCTGGGCTGAGAACATTAAAAA

CACAGTCAACATGATGCGTAGGATCATAGGTGATGAAGAAAAGTACGTGGACTA

CCTATCCACCCAAGTTCGCTACTTGGGCGAAGAAGGGTCCACACCTGGAGTGCTA

TAAGCACCAATCTTAGTGTTGTCAGGCCTGCTAGTCAGCCACAGCTTGGGGAAAG

CTGTGCAGCCTGTGACCCCCCAGGAGAAGCTGGGAAACCAAGCCCATAGTCAG

GCCGAGAACGCCATGGCACGGAAGAAGCCATGCTGCCTGTGAGCCCCTCAGAGG

ACACTGAGTCAAAAAACCCCACGCGCTTGGAGGCGCAGGATGGGAAAAGAAGG

TGGCGACCTTCCCCACCCTTTAATCTGGGGCCTGAACTGGAGATCAGCTGTGGAT

CTCCAGAAGAGGGACTAGTGGTTAGAGGAGACCCCCCGGAAAACGCAAAACAG
```

-continued

```
CATATTGACGCTGGGAAAGACCAGAGACTCCATGAGTTTCCACCACGCTGGCCG
CCAGGCACAGATCGCCGAATAGCGGCGGCCGGTGTGGGGAAATCCATGGgTCTgg
gtcggcatggcatctccacctcctcgcggtccgacctgggctacttcggtaggctaagggagaagaatcgatgctgtgccttc
tagttgccagccatctgttgtttgcccctcccccgtgccttccttgaccctggaaggtgccactcccactgtcctttcctaat
aaaatgaggaaattgcatcgcattgtctgagtaggtgtcattctattctggggggtggggtggggcaggacagcaagggggag
gattgggaagacaatagcaggcatgctggggatgcggtgggctctatgggcccggggccgtcgaccaattctcatgtttgacag
cttatcatcgaatttctgccattcatccgcttattatcacttattcaggcgtagcaaccaggcgtttaagggcaccaataact
gccttaaaaaaattacgccccgccctgccactcatcgcagtactgttgtaattcattaagcattctgccgacatggaagccat
cacaaacggcatgatgaacctgaatcgccagcggcatcagcaccttgtcgccttgcgtataatatttgcccatggtgaaaacg
ggggcgaagaagttgtccatattggccacgtttaaatcaaaactggtgaaactcacccagggattggctgagacgaaaaacat
attctcaataaacccctttagggaaataggccaggttttcaccgtaacacgccacatcttgcgaatatatgtgtagaaactgcc
ggaaatcgtcgtggtattcactccagagcgatgaaaacgtttcagtttgctcatggaaaacggtgtaacaagggtgaacacta
tcccatatcaccagacaccgtctttcattgccatacgaaattccggatgagcattcatcaggcgggcaagaatgtgaataaag
gccgataaaacttgtgcttatttttcttttacggtctttaaaaaggccgtaatatccagctgaacggtctggttataggtaca
ttgagcaactgactgaaatgcctcaaaatgttctttacgatgccattgggatatatcaacggtggtatatccagtgattttt
tctccattttagcttccttagctcctgaaaatctcgataactcaaaaaatacgcccggtagtgatcttatttcattatggtga
aagttggaacctcttacgtgccgatcaacgtctcattttcgccaaaagttggcccagggcttcccggtatcaacagggacacc
aggatttatttattctgcgaagtgatcttccgtcacaggtatttattcgcgataagctcatggagcggcgtaaccgtcgcaca
ggaaggacagagaaagcgcggatctgggaagtgacggacagaacggtcaggacctggattggggaggcggttgccgccgctgc
tgctgacggtgtgacgttctctgttccggtcacaccacatacgttccgccattcctatgcgatgcacatgctgtatgccggta
taccgctgaaagttctgcaaagcctgatgggacataagtccatcagttcaacggaagtctacacgaaggtttttgcgctggat
gtggctgcccggcaccgggtgcagtttgcgatgccggagtctgatgcggttgcgatgctgaaacaattatcctgagaataaat
gccttggcctttatatggaaatgtggaactgagtggatatgctgtttttgtctgttaaacagagaagctggctgttatccact
gagaagcgaacgaaacagtcgggaaaatctcccattatcgtagagatccgcattattaatctcaggagcctgtgtagcgttta
taggaagtagtgttctgtcatgatgcctgcaagcggtaacgaaaacgatttgaatatgccttcaggaacaatagaaatcttcg
tgcggtgttacgttgaagtggagcggattatgtcagcaatggacagaacaacctaatgaacacagaaccatgatgtggtctgt
ccttttacagccagtagtgctcgccgcagtcgagcgacagggcgaagccctcggctggttgccctcgccgctgggctggcggc
cgtctatggccctgcaaacgcgccagaaacgccgtcgaagccgtgtgcgagacaccgcggccggccgccggcgttgtggatac
ctcgcggaaaacttggccctcactgacagatgaggggcggacgttgacacttgaggggccgactcacccggcgcggcgttgac
agatgaggggcaggctcgatttcggccggcgacgtggagctggccagcctcgcaaatcggcgaaaacgcctgattttacgcga
gtttcccacagatgatgtggacaagcctgggataagtgccctgcggtattgacacttgaggggcgcgactactgacagatga
ggggcgcgatccttgacacttgaggggcagagtgctgacagatgaggggcgcacctattgacatttgaggggctgtccacagg
cagaaaatccagcatttgcaagggtttccgcccgttttcggccaccgctaacctgtcttttaacctgcttttaaaccaatat
ttataaaccttgtttttaaccagggctgcgccctgtgcgcgtgaccgcgcacgccgaagggggtgcccccccttctcgaacc
ctcccggtcgagtgagcgaggaagcaccagggaacagcacttatatattctgcttacacacgatgcctgaaaaaacttcccctt
ggggttatccacttatccacggggatattttataattattttttttatagttttagatcttctttttttagagcgccttgta
ggcctttatccatgctggttctagagaaggtgttgtgacaaattgccctttcagtgtgacaaatcaccctcaaatgacagtcc
tgtctgtgacaaattgcccttaaccctgtgacaaattgccctcagaagaagctgttttttcacaaagttatccctgcttattg
actcttttttatttagtgtgacaatctaaaaacttgtcacacttcacatggatctgtcatggcggaaacagcggttatcaatc
acaagaaacgtaaaaatagcccgcgaatcgtccagtcaaacgacctcactgaggcggcatatagtctctcccgggatcaaaaa
```

-continued cgtatgctgtatctgttcgttgaccagatcagaaaatctgatggcaccctacaggaacatgacggtatctgcgagatccatgt tgctaaatatgctgaaatattcggattgacctctgcggaagccagtaaggatatacggcaggcattgaagagtttcgcgggga aggaagtggttttttatcgccctgaagaggatgccggcgatgaaaaaggctatgaatcttttccttggtttatcaaacgtgcg cacagtccatccagagggctttacagtgtacatatcaacccatatctcattcccttctttatcgggttacagaaccggtttac gcagtttcggcttagtgaaacaaaagaaatcaccaatccgtatgccatgcgtttatacgaatccctgtgtcagtatcgtaagc cggatggctcaggcatcgtctctctgaaaatcgactggatcatagagcgttaccagctgcctcaaagttaccagcgtatgcct gacttccgccgccgcttcctgcaggtctgtgttaatgagatcaacagcagaactccaatgcgcctctcatacattgagaaaaa gaaaggccgccagacgactcatatcgtattttccttccgcgatatcacttccatgacgacaggatagtctgagggttatctgt cacagatttgagggtggttcgtcacatttgttctgacctactgagggtaatttgtcacagttttgctgtttccttcagcctgc atggattttctcatactttttgaactgtaattttttaaggaagccaaatttgagggcagtttgtcacagttgatttccttctct ttcccttcgtcatgtgacctgatatcggggggttagttcgtcatcattgatgagggttgattatcacagtttattactctgaat tggctatccgcgtgtgtacctctacctggagttttttcccacggtggatatttcttcttgcgctgagcgtaagagctatctgac agaacagttcttctttgcttcctcgccagttcgctcgctatgctcggttacacggctgcggcgagcgctagtgataataagtg actgaggtatgtgctcttcttatctccttttgtagtgttgctcttattttaaacaactttgcggttttttgatgactttgcga ttttgttgttgctttgcagtaaattgcaagatttaataaaaaaacgcaaagcaatgattaaaggatgttcagaatgaaactca tggaaacacttaaccagtgcataaacgctggtcatgaaatgacgaaggctatcgccattgcacagtttaatgatgacagcccg gaagcgaggaaaataacccggcgctggagaataggtgaagcagcggatttagttggggtttcttctcaggctatcagagatgc cgagaaagcagggcgactaccgcacccggatatggaaattcgaggacgggttgagcaacgtgttggttatacaattgaacaaa ttaatcatatgcgtgatgtgtttggtacgcgattgcgacgtgctgaagacgtatttccaccggtgatcggggttgctgcccat aaaggtggcgtttacaaaacctcagtttctgttcatcttgctcaggatctggctctgaaggggctacgtgttttgctcgtgga aggtaacgaccccagggaacagcctcaatgtatcacggatgggtaccagatcttcatattcatgcagaagacactctcctgc ctttctatcttggggaaaaggacgatgtcacttatgcaataaagcccacttgctggccggggcttgacattattccttcctgt ctggctctgcaccgtattgaaactgagttaatgggcaaatttgatgaaggtaaactgcccaccgatccacacctgatgctccg actggccattgaaactgttgctcatgactatgatgtcatagttattgacagcgcgcctaacctgggtatcggcacgattaatg tcgtatgtgctgctgatgtgctgattgttcccacgcctgctgagttgtttgactacacctccgcactgcagttttttcgatatg cttcgtgatctgctcaagaacgttgatcttaaagggttcgagcctgatgtacgtattttgcttaccaaatacagcaatagtaa tggctctcagtccccgtggatggaggagcaaattcggatgcctggggaagcatggttctaaaaaatgttgtacgtgaaacgg atgaagttggtaaaggtcagatccggatgagaactgttttttgaacaggccattgatcaacgctcttcaactggtgcctggaga aatgctctttctatttgggaacctgtctgcaatgaaattttcgatcgtctgattaaaccacgctgggagattagataatgaag cgtgcgcctgttattccaaaacatacgctcaatactcaaccggttgaagatacttcgttatcgacaccagctgccccgatggt ggattcgttaattgcgcgcgtaggagtaatggctcgcggtaatgccattactttgcctgtatgtggtcgggatgtgaagtttta ctcttgaagtgctccggggtgatagtgttgagaagacctctcgggtatggtcaggtaatgaacgtgaccaggagctgcttact gaggacgcactggatgatctcatcccttcttttctactgactggtcaacagacaccggcgttcggtcgaagagtatctggtgt catagaaattgccgatgggagtcgccgtcgtaaagctgctgcacttaccgaaagtgattatcgtgttctggttggcgagctgg atgatgagcagatggctgcattatccagattgggtaacgattatcgcccaacaagtgcttatgaacgtggtcagcgttatgca agccgattgcagaatgaatttgctggaaatatttctgcgctggctgatgcggaaaatatttcacgtaagattattacccgctg tatcaacaccgccaaattgcctaaatcagttgttgctctttttctcaccccggtgaactatctgcccggtcaggtgatgcac ttcaaaaagcctttacagataaagaggaattacttaagcagcaggcatctaaccttcatgagcagaaaaagctggggtgata tttgaagctgaagaagttatcactcttttaacttctgtgcttaaaacgtcatctgcatcaagaactagtttaagctcacgaca tcagtttgctcctggagcgacagtattgtataagggcgataaaatggtgcttaacctggacaggtctcgtgttccaactgagt gtatagagaaaattgaggccattcttaaggaacttgaaaagccagcaccctgatgcgaccacgttttagtctacgtttatctg -continued tctttacttaatgtcctttgttacaggccagaaagcataactggcctgaatattctctctgggcccactgttccacttgtatc gtcggtctgataatcagactgggaccacggtcccactcgtatcgtcggtctgattattagtctgggaccacggtcccactcgt atcgtcggtctgattattagtctgggaccacggtcccactcgtatcgtcggtctgataatcagactgggaccacggtcccact cgtatcgtcggtctgattattagtctgggaccatggtcccactcgtatcgtcggtctgattattagtctgggaccacggtccc actcgtatcgtcggtctgattattagtctggaaccacggtcccactcgtatcgtcggtctgattattagtctgggaccacggt cccactcgtatcgtcggtctgattattagtctgggaccacgatcccactcgtgttgtcggtctgattatcggtctgggaccac ggtcccacttgtattgtcgatcagactatcagcgtgagactacgattccatcaatgcctgtcaagggcaagtattgacatgtc gtcgtaacctgtagaacggagtaacctcggtgtgcggttgtatgcctgctgtggattgctgctgtgtcctgcttatccacaac attttgcgcacggttatgtggacaaaatacctggttacccaggccgtgccggcacgttaacCGTTACATAACTTACGGTAAAT

GGCCCGCCTGGCTGACCGC

CCAACGACCCCCGCCCATTGACGTCAATAATGACGTATGTTCCCATAGTAACGCC

AATAGGGACTTTCCATTGACGTCAATGGGTGGAGTATTTACGGTAAACTGCCCAC

TTGGCAGTACATCAAGTGTATCATATGCCAAGTACGCCCCCTATTGACGTCAATG

ACGGTAAATGGCCCGCCTGGCATTATGCCCAGTACATGACCTTATGGGACTTTCC

TACTTGGCAGTACATCTACGTATTAGTCATCGCTATTACCATGGTGATGCGGTTTT

GGCAGTACATCAATGGGCGTGGATAGCGGTTTGACTCACGGGGATTTCCAAGTCT

CCACCCCATTGACGTCAATGGGAGTTTGTTTTGGCACCAAAATCAACGGGACTTT

CCAAAATGTCGTAACAACTCCGCCCCATTGACGCAAATGGGCGGTAGGCGTGTA

CGGTGGGAGGTCTATATAAGCAGAGCTCTCTGGCTAAC

SV40 ZIKV FL sequence:

SEQ ID NO: 7 agttgttgatctgtgtgaatcagactgcgacagttcgagtttgaagcgaaagctagcaacagtatcaacaggttttattttgg atttggaaacgagagtttctggtcatgaaaaacccaaagaagaaatccggaggattccggattgtcaatatgctaaaacgcgg agtagcccgtgtgagcccctttgggggcttgaagaggctgccagccggacttctgctgggtcatgggcccatcaggatggtct tggcgattctagcctttttgagattcacggcaatcaagccatcactgggtctcatcaatagatggggttcagtggggaaaaaa gaggctatggaaataataaagaagtttaagaaagatctggctgccatgctgagaataatcaatgctaggaaggagaagaagag acgaggcacagatactagtgtcggaattgttggcctcctgctgaccacagccatggcagtggaggtcactagacgtgggaatg catactatatgtacttggacagaagcgatgctggggaggccatatcttttccaaccacaatggggatgaataagtgttatata cagatcatggatcttggacacatgtgtgatgccaccatgagctatgaatgccctatgctggatgagggggtagaaccagatga cgtcgattgttggtgcaacacgacgtcaacttgggttgtgtacggaacctgccaccacaaaaaggtgaagcacggagatcta gaagagctgtgacgctcccctcccattccactaggaagctgcaaacgcggtcgcagacctggttggaatcaagagaatacaca aagcacctgattagagtcgaaaattggatattcaggaaccctggcttcgcgttagcagcagctgccatcgcttggcttttggg aagctcaacgagccaaaaagtcatatacttggtcatgatactgctgattgccccggcatacagcatcaggtgcataggagtca gcaatagggactttgtggaaggtatgtcaggtgggacttgggttgatgttgtcttggaacatggaggttgtgttaccgtaatg gcacaggacaaaccgactgtcgacatagagctggttacaacaacagtcagcaacatggcggaggtaagatcctactgctatga ggcatcaatatcggacatggcttcggacagccgctgcccaacacaaggtgaagcctaccttgacaagcaatcagacactcaat atgtctgcaaaagaacgttagtggacagaggctggggaaatggatgtggactttttggcaaagggagcctggtgacatgcgct aagtttgcttgctctaagaaaatgaccgggaagagcatccagccagagaatctggagtaccggataatgctgtcagttcatgg ctcccagcacagtgggatgatcgttaatgatacaggacatgaaactgatgagaatagagcgaaggttgagataacgcccaatt caccaagagccgaagccaccctgggggttttggaagcctaggacttgattgtgaaccgaggacaggccttgacttttcagat ttgtattacttgactatgaataacaagcactggttggttcacaaggagtggttccacgacattccattaccttggcacgctgg -continued

```
ggcagacaccggaactccacactggaacaacaaagaagcactggtagagttcaaggacgcacatgccaaaaggcagactgtcg tggttctagggagtcaagaaggagcagttcacacggcccttgctggagctctggaggctgagatggatggtgcaaagggaagg ctgtcctctggccacttgaaatgtcgcctgaaaatggacaaacttagattgaagggcgtgtcatactccttgtgtaccgcagc gttcacattcactaagatcccggctgaaacactgcacgggacagtcacagtggaggtacagtacgcagggacagatggacctt gcaaggttccagctcagatggcggtggacatgcaaactctgaccccagttgggaggttgataaccgctaaccctgtaatcact gaaagcactgagaactccaagatgatgctggaactggatccaccatttggggactcttacattgtcataggagtcggggaaaa gaagatcacccaccactggcacaggagtggcagcaccattggaaaagcatttgaagccactgtgagaggtgccaagagaatgg cagtcttgggagacacagcctgggactttggatcagttgggggtgctctcaactcactgggcaagggcatccatcaaatttt ggagcagctttcaaatcattgtttggaggaatgtcctggttctcacaaattctcattggaacgttgctggtgtggttgggtct gaatacaaagaatggatctatttcccttatgtgcttggccttagggggagtgttgatcttcttatccacagccgtctctgctg atgtggggtgctcggtggacttctcaaagaaggaaacgagatgcggtacaggggtgttcgtctataacgacgttgaagcttgg agggacaggtacaagtaccatcctgactcccctcgtagattggcagcagcagtcaagcaagcctgggaagatgggatctgtgg gatctcctctgtttcaagaatggaaaacatcatgtggagatcagtagaagggagctcaacgcaatcctggaagagaatggag ttcaactgacggtcgttgtgggatctgtaaaaaacccccatgtggagaggtccacagagattgcccgtgcctgtgaacgagctg ccccatggctggaaggcttgggggaaatcgtacttcgtcagggcagcaaagacaaataacagctttgtcgtggatggtgacac actgaaggaatgcccactcaaacatagagcatggaacagcttcttgtggaggatcatgggttcggggtatttcacactagtg tctggctcaaggttagagaagattattcactcgagtgtgatccagccgtcattggaacagccgctaagggaaaggaggctgtg cacagtgatctaggctactggattgagagtgagaagaacgacacatggaggctgaagagggcccacctgatcgagatgaaaac atgtgaatggccaaagtcccacacattgtggacagatggaatagaagaaagtgatctgatcatacccaagtctttagctgggc cactcagccatcacaacaccagagagggctacaggacccaaatgaaagggccatggcatagtgaagagcttgaaattcggttt gaggaatgcccaggcactaaggtccacgtggaggaaacatgtggaacaagaggaccatctctgagatcaaccactgcaagcgg aagggtgatcgaggaatggtgctgcagggagtgcacaatgcccccactgtcgttccgggctaaagatggttgttggtatggaa tggagataaggcccaggaaagaaccagaaagtaacttagtaaggtcaatggtgactgcaggatcaactgatcacatggatcac ttctcccttggagtgcttgtgattctgctcatggtacaggaagggctaaagaagagaatgaccacaaagatcatcataagcac atcaatggcagtgctggtagctatgatcctgggaggattttcaatgagtgacctggctaagcttgcaattttgatgggtgcca ccttcgcggaaatgaacactggaggagatgttgctcatctggcgctgatagcggcattcaaagtcagacctgcgttgctggta tctttcattttcagagctaattggacaccccgtgagagcatgctgctggccttggctcgtgtcttctgcaaactgcgatctc cgccttggaaggcgacctgatggttcccatcaatggttttgctttggcctggttggcaatacgagcgatggttgttccacgca ctgacaacatcaccttggcaatcctggctgctctgacaccactggcccggggcacactgcttgtggcgtggagagcaggcctt gctacttgcgggggggttcatgctcctttctctgaaggggaaaggcagtgtgaagaagaacttaccatttgtcatggccctggg actaaccgctgtgaggctggtcgaccccatcaacgtggtgggactgctgttgctcacaaggagtgggaagcggagctggcccc ctagtgaagtactcacagctgttggcctgatatgcgcattggctggagggttcgccaaggcggatatagagatggctgggccc atggccgcggtcggtctgctaattgtcagttacgtggtctcaggaaagagtgtggacatgtacattgaaagagcaggtgacat cacatgggaaaagatgcggaagtcactggaaacagtccccggctcgatgtggcactagatgagagtggtgatttctccctag tggaggatgatggtcccccatgagagagatcatactcaaagtggtcctgatggccatctgtggcatgaacccaatagccata cccttgcagctggagcgtggtacgtgtatgtgaagactggaaaaaggagtggtgctctatgggatgtgcctgctcccaagga agtaaaaaggggggagaccacagatggagtgtacagagtaatgactcgtagactgctaggttcaacacaagttggagtgggag tcatgcaagaggggtcttccacactatgtggcacgtcacaaaaggatccgcgctgagaagcggtgaagggagacttgatcca tactggggagatgtcaaggcaggatctggtgtcatactgtggtccatggaagctagatgccgcctgggacgggcacagcgaggt gcagctcttggccgtgccccccggagagagagcgaggaacatccagactctgcccggaatatttaagacaaaggatggggaca ttggagcagttgcgctggactacccagcaggtacctcaggatctccaatcctagataagtgtgggagagtgatagactctat
```

-continued

```
ggtaatggggtcgtgatcaaaaatgggagttacgttagtgccatcacccaagggaggagggaggaagagactcctgttgagtg cttcgagccttcgatgctgaagaagaagcagctaactgtcttagacttgcatcctggagctgggaaaaccaggagagttcttc ctgaaatagtccgtgaagccataaaaacaagactccgcactgtgatcttagctccaaccagggttgtcgctgctgaaatggag gaagcccttagagggcttccagtgcgttatatgacaacagcagtcaatgtcacccattctgggacagaaatcgttgacttaat gtgccatgccaccttcacttcacgtctactacagccaatcagagtccccaactataatctgtatattatggatgaggcccact tcacagatccctcaagtatagcagcaagaggatacatttcaacaaggggttgagatgggcgaggcggctgccatcttcatgact gccacgccaccaggaacccgtgacgcattcccggactccaactcaccaattatggacaccgaagtggaagtcccagagagagc ctggagctcaggctttgattgggtgacggatcattctggaaaaacagtttggtttgttccaagcgtgaggaatggcaatgaga tcgcagcttgtctgacaaaggctggaaaacgggtcatacagctcagcagaaagacttttgagacagagttccagaaaacaaaa catcaagagtgggacttcgtcgtgacaactgacatttcagagatgggcgccaactttaaagctgaccgtgtcatagattccag gagatgcctaaagccggtcatacttgatggcgagagagtcattctggctggacccatgcctgtcacacatgccagcgctgccc agaggagggggcgcataggcaggaaccccaacaaacctggagatgagtatctgtatggaggtgggtgcgcagagactgatgaa gaccatgcacactggcttgaagcaagaatgcttcttgacaacatttacctccaagatggcctcatagcctcgctctatcgacc tgaggccgacaaagtagcagctattgagggagagttcaagcttaggacggagcaaaggaagacctttgtggaactcatgaaaa gaggagatcttcctgtttggctggcctatcaggttgcatctgccggaataacctacacagatagaagatggtgctttgatggc acgaccaacaacaccataatggaagacagtgtgccggcagaggtgtggaccagatacggagagaaaagagtgctcaaaccgag gtggatggacgccagagtttgttcagatcatgcggccctgaagtcattcaaagagtttgccgctgggaaaagaggagcggcct ttggagtgatggaagccctgggaacactgccaggacatatgacagagagattccaggaggccattgacaacctcgctgtgctc atgcgggcagagactggaagcaggccctacaaagccgcggcggcccaattaccggagaccctagagactatcatgcttttggg gttgctgggaacagtctcgctgggaatcttttcgtcttgatgcggaacaagggcatagggaagatgggctttggaatggtga ctcttggggccagcgcatggcttatgtggctctcggaaattgagccagccagaattgcatgtgtcctcattgttgtgttccta ttgctggtggtgctcatacctgagccagaaaagcaaagatctccccaggacaaccaaatggcaatcatcatcatggtagcagt gggtcttctgggcttgattaccgccaatgaactcggatggttggagagaacaaagagtgacctaagccatctaatgggaagga gagaggaggggcaactataggattctcaatggacattgacctgcggccagcctcagcttgggctatctatgctgctctgaca actttcattaccccagccgtccaacatgcagtgaccacttcatacaacaactactccttaatggcgatggccacgcaagctgg agtgttgttcggtatgggtaaagggatgccattctatgcatgggactttggagtcccgctgctaatgataggttgctactcac aattaacacccctgaccctaatagtggccatcattttgctcgtggcgcactacatgtacttgatcccagggctgcaggcagca gctgcgcgtgctgcccagaagagaacggcagctggcatcatgaagaaccctgttgtggatggaatagtggtgactgacattga cacaatgacaattgaccccaagtggagaaaaagatgggacaggtgctactcatagcagtagctgtctccagcgccatactgt cgcggaccgcctgggggtggggtgaggctggggccctgatcacagctgcaacttccactttgtgggagggctctccgaacaag tactggaactcctccacagccacctcactgtgtaacatttttaggggaagctacttggctggagcttctctaatctacacagt aacaagaaacgctggcttggtcaagagacgtgggggtggaacgggagagaccctgggagagaaatggaaggcccgcctgaacc agatgtcggccctggagttctactcctacaaaaagtcaggcatcaccgaggtgtgcagagaagaggcccgccgcgccctcaag gacggtgtggcaacgggaggccacgctgtgtcccgaggaagtgcaaagctgagatggttggtggagaggggatacctgcagcc acttggaaaggtcattgatcttggatgtggcagaggggctggagttactatgccgccaccatccgcaaagttcaagaagtga aaggatacacaaaaggaggccctggtcatgaagaacccatgttggtgcaaagctatgggtggaacatagtccgtcttaagagt ggggtggacgtctttcatatggcggctgagccgtgtgacacgttgctgtgtgatataggtgagtcatcatctagtcctgaagt ggaagaagcacggacgctcagagtcctctccatggtgggggattggcttgaaaaaagaccaggagccttttgtataaaagtgt tgtgcccatacaccagcactatgatggaaaccctggagcgactgcagcgtaggtatggggggaggactggtcagagtgccactc tcccgcaactctacacatgagatgtactgggtctctggagcgaaaagcaacaccataaaaagtgtgtccaccacgagccagct
```

-continued

```
ccttttggggcgcatggacgggcccaggaggccagtgaaatatgaagaggatgtgaatctcggctctggcacgcgggctgtgg taagctgcgctgaagctcccaacatgaagatcattggtaaccgcattgagaggatccgcagtgagcacgcgggaaacgtggttc tttgacgagaaccacccatataggacatgggcttaccatggaagctacgaggcccccacacaagggtcagcgtcctctctaat aaacggggttgtcaggctcctgtcaaaaccctgggatgtggtgactggagtcacaggaatagccatgaccgacaccacaccgt atggtcagcaaagagttttcaaggaaaaagtggacactagggtgccagaccccccaagaaggcactcgtcaggttatgagcatg gtctcttcctggttgtggaaagagttaggcaaacacaaacgccacgagtctgtaccaaagaagagttcatcaacaaggttcg tagcaacgcagcattaggggcaatatttgaagaggaaaaagagtggaagactgcagtggaagctgtgaacgatccaaggttct gggctctagtggacaaggaaagagagcaccacctgagaggagagtgccagagctgtgtgtacaacatgatgggaaaaagagaa aagaaacaagggggaatttggaaaggccaagggcagccgcgccatctggtacatgtggctaggggctagatttctagagttcga agcccttggattcttgaacgaggatcactggatggggagagagaattcaggaggtggtgttgaagggctaggattacaaagac tcggatatgtcttagaagagatgagtcgcataccaggaggaaggatgtatgcagatgatactgctggctgggacacccgcatc agcaggtttgatctggagaatgaagctctaatcaccaaccaaatggagaaagggcacagggccttggcattggccataatcaa gtacacataccaaaacaaagtggtaaaggtccttagaccagctgaaaaagggaagacagttatggacattatttcaagacaag accaaggggggagcggacaagttgtcacttacgctcttaatacatttaccaacctagtggtgcagctcattcggaatatggag gctgaggaagttctagagatgcaagacttgtggctgctgcggaggtcagagaaagtgaccaactggttgcagagcaatggatg ggataggctcaaacgaatggcagtcagtggagatgattgcgttgtgaaaccaattgatgataggtttgcacatgctctcaggt tcttgaatgatatgggaaaagttaggaaggacacacaagagtggaagccctcaactggatgggacaactgggaagaagttccg ttttgctcccaccacttcaacaagctccatctcaaggacgggaggtccattgtggttccctgccgccaccaagatgaactgat tggccgagctcgcgtctcaccggggcgggatggagcatccgggagactgcttgcctagcaaaatcatatgcgcaaatgtggc agctcctttatttccacagaagggacctccgactgatggccaatgccatttgttcatctgtgccagttgactgggttccaact gggagaactacctggtcaatccatggaaagggagaatggatgaccactgaagacatgcttgtggtgtggaacagagtgtggat tgaggagaacgaccacatggaagacaagacccagttacgaaatggacagacattccctatttgggaaaaagggaagacttgt ggtgtgggtctctcataggcacagaccgcgcaccacctgggctgagaacattaaaaacacagtcaacatgatgcgtaggatc ataggtgatgaagaaaagtacgtggactacctatccacccaagttcgctacttgggcgaagaagggtccacacctggagtgct ataagcaccaatcttagtgttgtcaggcctgctagtcagccacagcttggggaaagctgtgcagcctgtgaccccccaggag aagctgggaaaccaagcccatagtcaggccgagaacgccatggcacggaagaagccatgctgcctgtgagcccctcagaggac actgagtcaaaaaaccccacgcgcttggaggcgcaggatgggaaaagaaggtggcgaccttccccaccctttaatctggggcc tgaactggagatcagctgtggatctccagaagagggactagtggttagaggagaccccccggaaaacgcaaaacagcatattg acgctgggaaagaccagagactccatgagtttccaccacgctggccgccaggcacagatcgccgaatagcggcggccggtgtg gggaaatccatgggtctgggtcggcatggcatctccacctcctcgcggtccgacctgggctacttcggtaggctaagggagaa gaatcgatgaacttgtttattgcagcttataatggttacaaataaagcaatagcatcacaaatttcacaaataaagcattttt ttcactgcattctagttgtggtttgtccaaactcatcaatgtatcttatgcccgggccgtcgaccaattctcatgtttgacag cttatcatcgaatttctgccattcatccgcttattatcacttattcaggcgtagcaaccaggcgtttaagggcaccaataact gccttaaaaaaattacgccccgccctgccactcatcgcagtactgttgtaattcattaagcattctgccgacatggaagccat cacaaacggcatgatgaacctgaatcgccagcggcatcagcaccttgtcgccttgcgtataatatttgcccatggtgaaaacg ggggcgaagaagttgtccatattggccacgtttaaatcaaaactggtgaaactcacccagggattggctgagacgaaaaacat attctcaataaaccctttagggaaataggccaggttttcaccgtaacacgccacatcttgcgaatatatgtgtagaaactgcc ggaaatcgtcgtggtattcactccagagcgatgaaaacgtttcagtttgctcatggaaaacggtgtaacaagggtgaacacta tcccatatcaccagctcaccgtctttcattgccatacgaaattccggatgagcattcatcaggcgggcaagaatgtgaataaa ggccggataaaacttgtgcttattttctttacggtctttaaaaaggccgtaatatccagctgaacggtctggttataggtac attgagcaactgactgaaatgcctcaaaatgttctttacgatgccattgggatatatcaacggtggtatatccagtgatttt
```

-continued

```
ttctccatttttagcttccttagctcctgaaaatctcgataactcaaaaaatacgcccggtagtgatcttatttcattatggtg aaagttggaacctcttacgtgccgatcaacgtctcattttcgccaaaagttggcccagggcttcccggtatcaacagggacac caggatttatttattctgcgaagtgatcttccgtcacaggtatttattcgcgataagctcatggagcggcgtaaccgtcgcac aggaaggacagagaaagcgcggatctgggaagtgacggacagaacggtcaggacctggattggggaggcggttgccgccgctg ctgctgacggtgtgacgttctctgttccggtcacaccacatacgttccgccattcctatgcgatgcacatgctgtatgccggt ataccgctgaaagttctgcaaagcctgatgggacataagtccatcagttcaacggaagtctacacgaaggttttttgcgctgga tgtggctgcccggcaccgggtgcagtttgcgatgccggagtctgatgcggttgcgatgctgaaacaattatcctgagaataaa tgccttggcctttatatggaaatgtgaactgagtggatatgctgttttttgtctgttaaacagagaagctggctgttatccac tgagaagcgaacgaaacagtcgggaaaatctcccattatcgtagagatccgcattattaatctcaggagcctgtgtagcgttt ataggaagtagtgttctgtcatgatgcctgcaagcggtaacgaaaacgatttgaatatgccttcaggaacaatagaaatcttc gtgcggtgttacgttgaagtggagcggattatgtcagcaatggacagaacaacctaatgaacacagaaccatgatgtggtctg tccttttacagccagtagtgctcgccgcagtcgagcgacagggcgaagccctcggctggttgccctcgccgctgggctggcgg ccgtctatggccctgcaaacgcgccagaaacgccgtcgaagccgtgtgcgagacaccgcggccggccgccggcgttgtggata cctcgcggaaaacttggccctcactgacagatgaggggcggacgttgacacttgaggggccgactcaccggcgcggcgttga cagatgaggggcaggctcgatttcggccggcgacgtggagctggccagcctcgcaaatcggcgaaaacgcctgattttacgcg agtttcccacagatgatgtggacaagcctggggataagtgccctgcggtattgacacttgaggggcgcgactactgacagatg aggggcgcgatccttgacacttgaggggcagagtgctgacagatgaggggcgcacctattgacatttgagggctgtccacag gcagaaaatccagcatttgcaaggggttccgcccgttttcggccaccgctaacctgtcttttaacctgcttttaaaccaata tttataaaccttgttttaaccagggctgcgccctgtgcgcgtgaccgcgcacgccgaagggggtgcccccccttctcgaac cctcccggtcgagtgagcgaggaagcaccagggaacagcacttatatattctgcttacacacgatgcctgaaaaaacttccct tggggttatccacttatccacggggatattttataattatttttttttatagttttagatcttctttttagagcgccttgt aggcctttatccatgctggttctagagaaggtgttgtgacaaattgccctttcagtgtgacaaatcaccctcaaatgacagtc ctgtctgtgacaaattgcccttaaccctgtgacaaattgccctcagaagaagctgttttttcacaaagttatccctgcttatt gactcttttttatttagtgtgacaatctaaaaacttgtcacacttcacatggatctgtcatggcggaaacagcggttatcaat cacaagaaacgtaaaaatagcccgcgaatcgtccagtcaaacgacctcactgaggcggcatatagtctctcccgggatcaaaa acgtatgctgtatctgttcgttgaccagatcagaaaatctgatggcaccctacaggaacatgacggtatctgcgagatccatg ttgctaaatatgctgaaatattcggattgacctctgcggaagccagtaaggatatacggcaggcattgaagagtttcgcgggg aaggaagtggttttttatcgccctgaagaggatgccggcgatgaaaaaggctatgaatcttttccttggtttatcaaacgtgc gcacagtccatccagagggctttacagtgtacatatcaacccatatctcattcccttctttatcgggttacagaaccggttta cgcagtttcggcttagtgaaacaaaagaaatcaccaatccgtatgccatgcgtttatacgaatccctgtgtcagtatcgtaag ccggatggctcaggcatcgtctctctgaaaatcgactggatcatagagcgttaccagctgcctcaaagttaccagcgtatgcc tgacttccgccgccgcttcctgcaggtctgtgttaatgagatcaacagcagaactccaatgcgcctctcatacattgagaaaa agaaaggccgccagacgactcatatcgtatttttccttccgcgatatcacttccatgacgacaggatagtctgagggttatctg tcacagatttgagggtggttcgtcacatttgttctgacctactgagggtaatttgtcacagttttgctgtttccttcagcctg catggattttctcatactattgaactgtaattttaaggaagccaaatttgagggcagtttgtcacagttgatttccttctct ttcccttcgtcatgtgacctgatatcgggggttagttcgtcatcattgatgagggttgattatcacagtttattactctgaat tggctatccgcgtgtgtacctctacctggagttttttcccacggtggatatttcttcttgcgctgagcgtaagagctatctgac agaacagttcttcttttgcttcctcgccagttcgctcgctatgctcggttacacggctgcggcgagcgctagtgataataagtg actgaggtatgtgctcttcttatctccttttgtagtgttgctcttattttaaacaactttgcggttttttgatgactttgcga ttttgttgttgctttgcagtaaattgcaagatttaataaaaaaacgcaaagcaatgattaaaggatgttcagaatgaaactca
```

-continued

```
tggaaacacttaaccagtgcataaacgctggtcatgaaatgacgaaggctatcgccattgcacagtttaatgatgacagcccg gaagcgaggaaaataacccggcgctggagaataggtgaagcagcggatttagttggggtttcttctcaggctatcagagatgc cgagaaagcagggcgactaccgcacccggatatgaaattcgaggacgggttgagcaacgtgttggttatacaattgaacaaa ttaatcatatgcgtgatgtgtttggtacgcgattgcgacgtgctgaagacgtatttccaccggtgatcggggttgctgcccat aaaggtggcgtttacaaaacctcagtttctgttcatcttgctcaggatctggctctgaaggggctacgtgttttgctcgtgga aggtaacgaccccagggaacagcctcaatgtatcacggatgggtaccagatcttcatattcatgcagaagacactctcctgc ctttctatcttggggaaaaggacgatgtcacttatgcaataaagcccacttgctggccggggcttgacattattccttcctgt ctggctctgcaccgtattgaaactgagttaatgggcaaatttgatgaaggtaaactgcccaccgatccacacctgatgctccg actggccattgaaactgttgctcatgactatgatgtcatagttattgacagcgcgcctaacctgggtatcggcacgattaatg tcgtatgtgctgctgatgtgctgattgttcccacgcctgctgagttgtttgactacacctccgcactgcagttttcgatatg cttcgtgatctgctcaagaacgttgatcttaaagggttcgagcctgatgtacgtattttgcttaccaaatacagcaatagtaa tggctctcagtccccgtggatggaggagcaaattcgggatgcctggggaagcatggttctaaaaaatgttgtacgtgaaacgg atgaagttggtaaaggtcagatccggatgagaactgtttttgaacaggccattgatcaacgctcttcaactggtgcctggaga aatgctctttctatttgggaacctgtctgcaatgaaattttcgatcgtctgattaaaccacgctgggagattagataatgaag cgtgcgcctgttattccaaaacatacgctcaatactcaaccggttgaagatacttcgttatcgacaccagctgccccgatggt ggattcgttaattgcgcgcgtaggagtaatggctcgcggtaatgccattactttgcctgtatgtggtcgggatgtgaagttta ctcttgaagtgctccggggtgatagtgttgagaagacctctcgggtatggtcaggtaatgaacgtgaccaggagctgcttact gaggacgcactggatgatctcatcccttcttttctactgactggtcaacagacaccggcgttcggtcgaagagtatctggtgt catagaaattgccgatgggagtcgccgtcgtaaagctgctgcacttaccgaaagtgattatcgtgttctggttggcgagctgg atgatgagcagatggctgcattatccagattgggtaacgattatcgcccaacaagtgcttatgaacgtggtcagcgttatgca agccgattgcagaatgaatttgctggaaatatttctgcgctggctgatgcggaaaatatttcacgtaagattattacccgctg tatcaacaccgccaaattgcctaaatcagttgttgctcttttttctcaccccggtgaactatctgcccggtcaggtgatgcac ttcaaaaagcctttacagataaagaggaattacttaagcagcaggcatctaaccttcatgagcagaaaaaagctggggtgata tttgaagctgaagaagttatcactcttttaacttctgtgataaaacgtcatctgcatcaagaactagtttaagctcacgacat cagtttgctcctggagcgacagtattgtataagggcgataaaatggtgcttaacctggacaggtctcgtgttccaactgagtg tatagagaaaattgaggccattcttaaggaacttgaaaagccagcaccctgatgcgaccacgttttagtctacgtttatctgt ctttacttaatgtcctttgttacaggccagaaagcataactggcctgaatattctctctgggcccactgttccacttgtatcg tcggtctgataatcagactgggaccacggtcccactcgtatcgtcggtctgattattagtctgggaccacggtcccactcgta tcgtcggtctgattattagtctgggaccacggtcccactcgtatcgtcggtctgataatcagactgggaccacggtcccactc gtatcgtcggtctgattattagtctgggaccatggtcccactcgtatcgtcggtctgattattagtctgggaccacggtccca ctcgtatcgtcggtctgattattagtctggaaccacggtcccactcgtatcgtcggtctgattattagtctgggaccacggtc ccactcgtatcgtcggtctgattattagtctgggaccacgatcccactcgtgttgtcggtctgattatcggtctgggaccacg gtcccacttgtattgtcgatcagactatcagcgtgagactacgattccatcaatgcctgtcaagggcaagtattgacatgtcg tcgtaacctgtagaacggagtaacctcggtgtgcggttgtatgcctgctgtggattgctgctgtgtcctgcttatccacaaca ttttgcgcacggttatgtggacaaaatacctggttacccaggccgtgccggcacgttaactgtgtcagttagggtgtggaaag tccccaggctccccagcaggcagaagtatgcaaagcatgcatctcaattagtcagcaaccaggtgtggaaagtccccaggctc cccagcaggcagaagtatgcaaagcatgcatctcaattagtcagcaaccatagtcccgcccctaactccgcccatcccgcccc taactccgcccagttccgcccattctccgccccatggctgactaatttttttatttatgcagaggccgaggccgcctc
```

3' UTR Zika 10 Nucleotide Deletion

SEQ ID NO: 8

CCAGAAGAGG

3' UTR Zika 20 Nucleotide Deletion

SEQ ID NO: 9

CTGTGGATCTCCAGAAGAGG

The contents of the following references and all other references which are cited in this application are incorporated by reference in their entirety.

REFERENCES

1 Costello, A. et al. Defining the syndrome associated with congenital Zika virus infection. *Bull World Health Organ* 94, 406-406A, doi:10.2471/BLT.16.176990 (2016).

2 Weaver, S. C. et al. Zika virus: History, emergence, biology, and prospects for control. *Antiviral Res* 130, 69-80, doi:10.1016/j.antiviral.2016.03.010 (2016).

3 Shan, C. et al. Zika Virus: Diagnosis, Therapeutics, and Vaccine *ACS Infectious Diseases* 2, 170-172 (2016).

4 Dawes, B. E. et al. Research and development of Zika virus vaccines. *NPJ Vaccines* 1, 16007, doi:10.1038/npjvaccines.2016.7 (2016).

5 Barrett, A. D. T. Zika vaccine candidates progress through nonclinical development and enter clinical trials. *Npj Vaccines* 1, 16023, doi:10.1038/npjvaccines.2016.23 (2016).

6 Larocca, R. A. et al. Vaccine protection against Zika virus from Brazil. *Nature* 536, 474-478, doi:10.1038/nature18952 (2016).

7 Dowd, K. A. et al. Rapid development of a DNA vaccine for Zika virus. *Science* 354, 237-240, doi:10.1126/science.aai9137 (2016).

8 Abbink, P. et al. Protective efficacy of multiple vaccine platforms against Zika virus challenge in rhesus monkeys. *Science* 353, 1129-1132, doi:10.1126/science.aah6157 (2016).

9 Whitehead, S. S. Development of TV003/TV005, a single dose, highly immunogenic live attenuated dengue vaccine; what makes this vaccine different from the Sanofi-Pasteur CYD vaccine? *Expert review of vaccines* 15, 509-517, doi:10.1586/14760584.2016.1115727 (2016).

10 Shan, C. et al. An Infectious cDNA Clone of Zika Virus to Study Viral Virulence, Mosquito Transmission, and Antiviral Inhibitors. *Cell Host Microbe* 19, 891-900, doi:10.1016/j.chom.2016.05.004 (2016).

11 Xie, X. et al. Zika Virus Replicons for Drug Discovery. *EBioMedicine* 12, 156-160, doi:10.1016/j.ebiom.2016.09.013 (2016).

12 Lo, L., Tilgner, M., Bernard, K. & Shi, P.-Y. Functional analysis of mosquito-borne flavivirus conserved sequence elements within 3' untranslated region of West Nile virus using a reporting replicon that differentiates between viral translation and RNA replication. *J. Virol.* 77, 10004-10014 (2003).

13 Pijlman, G. P. et al. A highly structured, nuclease-resistant, noncoding RNA produced by flaviviruses is required for pathogenicity. *Cell Host Microbe* 4, 579-591, doi:10.1016/j.chom.2008.10.007 (2008).

14 Manokaran, G. et al. Dengue subgenomic RNA binds TRIM25 to inhibit interferon expression for epidemiological fitness. *Science* 350, 217-221, doi:10.1126/science.aab3369 (2015).

15 Acceptability of cell substrates for production of biologicals. Report of a WHO Study Group on Biologicals. World Health Organ Tech Rep Ser 747, 1-29 (1987).

16 Rossi, S. L. et al. Characterization of a Novel Murine Model to Study Zika Virus. *Am J Trop Med Hyg* 94, 1362-1369, doi:10.4269/ajtmh.16-0111 (2016).

17 Govero, J. et al. Zika virus infection damages the testes in mice. *Nature* 540, 438-442, doi:10.1038/nature20556 (2016).

18 Ma, W. et al. Zika Virus Causes Testis Damage and Leads to Male Infertility in Mice. *Cell* 167, 1511-1524 e1510, doi:10.1016/j.cell.2016.11.016 (2016).

19 Guerbois, M. et al. Outbreak of Zika Virus Infection, Chiapas State, Mexico, 2015, and First Confirmed Transmission by *Aedes aegypti* Mosquitoes in the Americas. *J Infect Dis*, doi:10.1093/infdis/jiw302 (2016).

20 Ferreira-de-Brito, A. et al. First detection of natural infection of *Aedes aegypti* with Zika virus in Brazil and throughout South America. *Mem Inst Oswaldo Cruz* 111, 655-658, doi:10.1590/0074-02760160332 (2016).

21 Yun, S. I. et al. Comparison of the live-attenuated Japanese Encephalitis vaccine SA14-14-2 strain with Its pre-attenuated virulent parent SA14 strain: Similarities and differences in vitro and in vivo. *J Gen Virol, doi:* 10.1099/jgv.0.000574 (2016).

22 Barrett, A. D. & Gould, E. A. Comparison of neurovirulence of different strains of yellow fever virus in mice. *J Gen Virol* 67 (Pt 4), 631-637, doi:10.1099/0022-1317-67-4-631 (1986).

23 Khromykh, A. A., Sedlak, P. L. & Westaway, E. G. Trans-Complementation analysis of the flavivirus Kunjin ns5 gene reveals an essential role for translation of its N-terminal half in RNA replication. *J. Virol.* 73, 9247-9255 (1999).

24 Khromykh, A., Kenney, M. & Westaway, E. trans-Complementation of flavivirus RNA polymerase gene NS5 by using Kunjin virus replicon-expressing BHK cells. *J. Virol.* 72, 7270-7279 (1998).

Qing, M., Liu, W., Yuan, Z., Gu, F. & Shi, P. Y. A high-throughput assay using dengue-1 virus-like particles for drug discovery. *Antiviral Res* 86, 163-171 (2010).

26 Xie, X., Zou, J., Puttikhunt, C., Yuan, Z. & Shi, P. Y. Two distinct sets of NS2A molecules are responsible for dengue virus RNA synthesis and virion assembly. *J Virol* 89, 1298-1313, doi:10.1128/JVI.02882-14 (2015).

27 Pugachev, K. et al. High fidelity of yellow fever virus RNA polymerase. *J. Virol.* 78, 1032-1038 (2004).

28 Xie, X. et al. Understanding Zika Virus Stability and Developing a Chimeric Vaccine through Functional Analysis. *MBio* 8, doi:10.1128/mBio.02134-16 (2017).

29 Yauch, L. E. et al. A protective role for dengue virus-specific $CD8^+$ T cells. *J Immunol* 182, 4865-4873, doi:10.4049/jimmunol.0801974 (2009).

30 Weiskopf, D. et al. Comprehensive analysis of dengue virus-specific responses supports an HLA-linked protective role for $CD8^+$ T cells. *Proc Natl Acad Sci USA* 110, E2046-2053, doi:10.1073/pnas.1305227110 (2013).

31 Shi, P. Y., Tilgner, M., Lo, M. K., Kent, K. A. & Bernard, K. A. Infectious cDNA clone of the epidemic West Nile virus from New York City. *J. Virol.* 76, 5847-5856 (2002).

32 Hansen, D. A., Esakky, P., Drury, A., Lamb, L. & Moley, K. H. The aryl hydrocarbon receptor is important for proper seminiferous tubule architecture and sperm development in mice. *Biol Reprod* 90, 8, doi:10.1095/biolreprod.113.108845 (2014).

33 Ye, Q. et al. Genomic characterization and phylogenetic analysis of Zika virus circulating in the Americas. *Infect Genet Evol* 43, 43-49, doi:10.1016/j.meegid.2016.05.004 (2016).

34 Akiyama, B. M. et al. Zika virus produces noncoding RNAs using a multi-pseudoknot structure that confounds a cellular exonuclease. *Science* 354, 1148-1152, doi: 10.1126/science.aah3963 (2016).

35 Taglietti et al. *Skin Ther. Lett.* 13:6-8 (2008)

36 Shan, C. et al. A live-attenuated Zika virus vaccine candidate induces sterilizing immunity in mouse models. *Nat Med*, doi:10.1038/nm.4322 (2017).

37 Xie, X. et al. Understanding Zika Virus Stability and Developing a Chimeric Vaccine through Functional Analysis. *MBio* 8, doi:10.1128/mBio.02134-16 (2017).

38 Shan, C. et al. A Rapid Zika Diagnostic Assay to Measure Neutralizing Antibodies in Patients. *EBioMedicine* 17, 157-162, doi:10.1016/j.ebiom.2017.03.006 (2017).

39 Lazear, H. M. et al. A Mouse Model of Zika Virus Pathogenesis. *Cell Host Microbe* 19, 720-730, doi: 10.1016/j.chom.2016.03.010 (2016).

Grant, A. et al. Zika Virus Targets Human STAT2 to Inhibit Type I Interferon Signaling. *Cell Host Microbe* 19, 882-890, doi:10.1016/j.chom.2016.05.009 (2016).

41 Miner, J. J. et al. Zika Virus Infection during Pregnancy in Mice Causes Placental Damage and Fetal Demise. *Cell* 165, 1081-1091, doi:10.1016/j.cell.2016.05.008 (2016)

42 Sapparapu, G. et al. Neutralizing human antibodies prevent Zika virus replication and fetal disease in mice. *Nature* 540, 443-447, doi:10.1038/nature20564 (2016).

43 Richner, J. et al. Vaccine mediated protection against Zika virus induced congenital disease. *Cell* 170, 273-283 (2017).

44 Acceptability of cell substrates for production of biologicals. Report of a WHO Study Group on Biologicals. World Health Organ Tech Rep Ser 747, 1-29 (1987).

45 Organization, W. H. WHO/UNICEF Zika virus vaccine target product profile: Vaccine to protect congenital Zika syndrome for use during an emergence. (2017).

46 Pardi, N. et al. Zika virus protection by a single low-dose nucleoside-modified mRNA vaccination. *Nature*, doi: 10.1038/nature21428 (2017).

47 Ong, E. Z. et al. Preclinical evaluation of VIS513, a therapeutic antibody against dengue virus, in non-human primates. *Antiviral Res* 144, 44-47, doi:10.1016/j.antiviral.2017.05.007 (2017).

48 Shan C, et al. A single-dose live-attenuated vaccine prevents Zika virus pregnancy transmission and testis damage. *Nature Communications: in press* (2017).

---

What is claimed is:

1. A live attenuated Zika virus (ZIKV) strain, comprising a deletion in the 3' untranslated region (3'UTR) of the ZIKV viral genome, the deletion comprising a deletion of sequence CCAGAAGAGG (SEQ ID NO:8).

2. The live attenuated ZIKV strain of claim 1, comprising a 3'UTR having a nucleic acid sequence that is at least 80% to 100% identical to the nucleic acid sequence of SEQ ID NO: 2, 3, 4, or 5.

3. The live attenuated ZIKV strain of claim 1, wherein the ZIKV strain is a mCherry ZIKV strain.

4. An immunogenic composition comprising a live attenuated ZIKV strain according to claim 1, which further comprises at least one pharmaceutically acceptable carrier or excipient.

5. The immunogenic composition of claim 4, wherein the composition is formulated for parenteral or enteral administration.

6. A method for eliciting an immune response in a subject in need thereof comprising administering a live attenuated ZIKV strain according to claim 1 in a subject in need thereof.

7. A method for eliciting an immune response in a subject in need thereof comprising administering a live attenuated ZIKV strain according to claim 2, in a subject in need thereof.

8. A method for eliciting an immune response in a subject in need thereof comprising administering a live attenuated ZIKV strain according to claim 3, in a subject in need thereof.

9. The method of claim 6, wherein the immune response comprises a CD8$^+$ T cell response, an antibody response, and/or a cellular immune response against ZIKV and/or the immune response comprises a neutralizing antibody titer equivalent to that of wildtype ZIKV infection.

10. The method of claim 6, wherein the subject is a pregnant female.

11. The method of claim 6, wherein the live attenuated ZIKV strain is administered as a dose of at least $1.0\times10^1$, $1.0\times10^2$, $1.0\times10^3$, $1.0\times10^4$, $1.0\times10^5$, or $1.0\times10^6$ IFUs.

12. The method of claim 6, wherein the subject treated is a human.

13. A live attenuated Zika virus (ZIKV) strain having a nucleic acid sequence that is at least 80% identical to SEQ ID NO:7 and comprises a 3' untranslated region (3'UTR) deletion of CCAGAAGAGG (SEQ ID NO:8).

14. The ZIKV strain of claim 13, having a nucleic acid sequence that is at least 90% to 100% identical to the nucleic acid sequence of SEQ ID NO:7 having a 3' untranslated region (3'UTR) deletion of CCAGAAGAGG (SEQ ID NO:8).

15. The live attenuated ZIKV strain of claim 1, wherein the nucleic acid sequence of the ZIKV viral genome is at least 80% to 100% identical to the nucleic acid sequence of SEQ ID NO:6 having a 3' untranslated region (3'UTR) deletion of CCAGAAGAGG (SEQ ID NO:8) or SEQ ID NO:7 having a 3' untranslated region (3'UTR) deletion of CCAGAAGAGG (SEQ ID NO:8).

16. The live attenuated ZIKV strain of claim 1, wherein the deletion comprises a deletion of nucleotide sequence CTGTGGATCTCCAGAAGAGG (3'UTR 20-nucleotide deletion) (SEQ ID NO:9).

* * * * *